United States Patent [19]

Konig et al.

[11] 4,147,693

[45] Apr. 3, 1979

[54] LACTAM ANTIBIOTICS AND PROCESS FOR THEIR USE

[75] Inventors: Hans-Bödo Konig; Karl G. Metzger; Michael Preiss; Wilfried Schröck, all of Wuppertal, Fed. Rep. of Germany

[73] Assignee: Bayer Aktiengesellschaft, Leverkusen, Fed. Rep. of Germany

[21] Appl. No.: 631,515

[22] Filed: Nov. 13, 1975

[30] Foreign Application Priority Data

Nov. 28, 1974 [DE] Fed. Rep. of Germany ....... 2456307
Mar. 25, 1975 [DE] Fed. Rep. of Germany ....... 2512998
Jun. 7, 1975 [DE] Fed. Rep. of Germany ....... 2525541

[51] Int. Cl.$^2$ .................. A61K 31/54; A61K 31/545; C07D 501/34; C07D 499/46
[52] U.S. Cl. .................................... 424/246; 424/271; 542/420; 260/239.1; 544/17
[58] Field of Search ............ 260/240 G, 239.1, 243 C, 260/243, 239.1 A, 239.1 TB; 424/246, 271; 542/420

[56] References Cited

U.S. PATENT DOCUMENTS

| | | | |
|---|---|---|---|
| 3,939,149 | 2/1976 | Konig et al. | 260/239.1 |
| 3,966,709 | 6/1976 | Konig et al. | 260/239.1 |
| 3,972,870 | 8/1976 | Konig et al. | 260/239.1 |
| 3,974,140 | 8/1976 | Konig et al. | 260/239.1 |
| 3,974,141 | 8/1976 | Konig et al. | 260/239.1 |
| 3,974,142 | 8/1976 | Konig et al. | 260/239.1 |
| 3,975,375 | 8/1976 | Konig et al. | 260/239.1 |
| 3,978,056 | 8/1976 | Konig et al. | 260/239.1 |
| 3,980,792 | 9/1976 | Konig et al. | 424/271 |
| 3,983,105 | 9/1976 | Konig et al. | 260/239.1 |

FOREIGN PATENT DOCUMENTS

| | | | |
|---|---|---|---|
| 767647 | 11/1971 | Belgium | 260/239.1 |
| 767648 | 11/1971 | Belgium | 260/239.1 |
| 2152968 | 4/1973 | Fed. Rep. of Germany | 260/239.1 |
| 7114254 | 11/1972 | Netherlands | 260/239.1 |

OTHER PUBLICATIONS

Chemical Abstracts, vol. 79, abst. no. 18697y, (1973), (Abst. of German Offen. 2,152,968).

Primary Examiner—John M. Ford
Attorney, Agent, or Firm—Sprung, Felfe, Horn, Lynch & Kramer

[57] ABSTRACT

6-[α-(Imidazolidin-2-on-1-ylcarbonylamino)-substututed acetamido]penicillanic acids, and the correspondingly 7-substituted ceph-3-em-4-carboxylic acids, characterized by the presence of a methyleneamino or substituted methyleneamino group on the 3-nitrogen atom of the imidazolidine ring are antibacterial agents. The compounds, of which 6-[α-(3-benzaliminoimidazolidin-2-on-1-ylcarbonylamino)cyclohexa-1,4-dien-1-ylacetamido]-penicillanic acid and 7-[α-(3-furylideneaminoimidazolidin-2-on-1-ylcarbonylamino)phenylacetamido]-3-(3-methylthiadiazol-5-ylthiomethyl)ceph-3-em-4-carboxylic acid are typical examples, are prepared through acylation of an 6-[α-(amino)substituted acetamido]-penicillanic acid or the corresponding 7-[α-(amino)substituted acetamido]ceph-3-em-4-carboxylic acid with a reactive nucleofugic derivative of a 3-methyleneaminoimidazolidin-2-on-1-carboxylic acid.

46 Claims, No Drawings

LACTAM ANTIBIOTICS AND PROCESS FOR THEIR USE

The present invention relates to new β-lactam antibiotics, to processes for their preparation and use, especially as anti-bacterial and growth promoting agents, and to compositions for such uses.

It is known that certain α-(imidazolidin-2-on-1-yl-carbonylamino)-benzylpenicillins are antibacterially active, see e.g. Belgian Pat. Nos. 767,647 and 767,648; Netherlands Patent Spec. No. 7,114,254 and German Published Specification No. 2,152,968.

The present invention pertains to β-lactams of the formula:

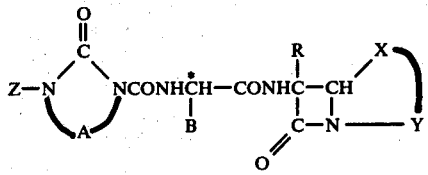

and the pharmaceutically acceptable salts thereof wherein the carbon atoms designated C constitutes a center of chirality and R is hydrogen or methoxy;
A is ethylene, trimethylene or benzo;
B is phenyl, hydroxyphenyl, halophenyl, lower alkylphenyl, cyanophenyl, methylsulfonylphenyl, cyclohexenyl or cyclohexadienyl;
X is S, O, SO, SO₂ or CH₂;
Y is

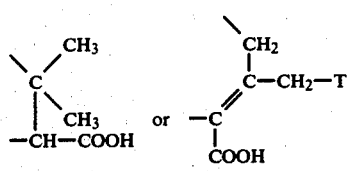

in which T is hydrogen, hydroxy, lower alkanoyloxy, pyridinium, carbamoyloxy, azido, cyano, phenylthio or Het-S- in which Het is a 5- to 6-membered heterocyclic ring; and
Z is

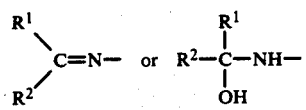

in which each of R¹ and R², independent of the other, is hydrogen; lower alkyl; lower alkenyl; cycloalkyl of 3 to 10 carbon atoms; cycloalkenyl of 3 to 10 carbon atoms; cycloalkenyl of 3 to 10 carbon atoms; a pyridyl, styryl, pyronyl or phenyl group unsubstituted or substituted by one or two substituents selected from the group consisting of fluoro, chloro, bromo, lower alkyl, lower alkoxy, nitro, cyano, lower alkylsulfonyl or carbo(lower alkoxy); a thienyl or furyl group unsubstituted or substituted by one or two substituents selected from the group consisting of fluoro, chloro, bromo, lower alkyl, carbo(lower alkoxy), lower alkanoyloxy and lower alkanoyloxymethyl; or isoxazolyl unsubstituted or substituted by methyl; or R¹ and R² taken together with the carbon atoms to which they are attached are a saturated or unsaturated ring of 3 to 7 ring members, said ring being carbocyclic or heterocyclic, said heterocyclic ring containing 1 or 2 hetero groups selected from the group consisting of oxygen, sulfur, imino and lower alkylimino.

The foregoing compounds possess several centers of chirality [see Cahn et al., Angew. Chem. internat. Edit., 5 (1966) No. 4, 385 et seq.]. With respect to those in the β-lactam nuclei itself (corresponding to penicillanic acid nucleus and cephalosporanic acid nucleus and derivatives thereof), the configuration about each chirality center corresponds to that of the naturally occurring molecule. With respect to the carbon atom designated C, the configuration can be either R (also known as the D-form) or S (also known as the L-form). Moreover, a further center of chirality can be present in the hydrated forms of the iminogroup when R¹ and R² are different. Additionally there are the syn and anti forms with respect to the imino group of Z. All of the individual diastereomers and isomers as well as mixtures thereof are within the scope of the present invention.

The term alkyl denotes a univalent saturated branched or straight hydrocarbon chain containing from 1 to 18 carbon atoms. Representative of such alkyl groups are thus methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkenyl denotes a univalent branched or straight hydrocarbon chain containing from 2 to 6 carbon atoms and nonterminal ethylenic unsaturation as, for example, vinyl, allyl, isopropenyl, 2-butenyl, 3-methyl-2-butenyl, 2-pentenyl, 3-pentenyl, 2-hexenyl, 4-hexenyl, and the like.

The term cycloalkyl denotes a univalent saturated monocyclic hydrocarbon of from 3 to 7 carbon atoms as, for example, cyclopropyl, cyclobutyl, cyclopentyl, cyclohexyl, and cycloheptyl.

The term bicycloalkyl denotes a univalent saturated ring system of two alicyclic rings having a total of 4 to 12 carbon atoms, two or more atoms of which are common to both rings, as for example bicyclo[2.2.1]heptyl, bicyclo[2.2.2]octyl and adamantyl.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term lower alkylthio denotes a branched or straight hydrocarbon chain of 1 to 6 carbon atoms bound to the remainder of the molecule through a divalent sulfur as, for example, methylthio, ethylthio, propylthio, isopropylthio, butylthio, and the like. Fluoro, chloro and bromo are preferred.

Halo (lower alkyl) refers to a lower alkyl group which is monohalogenated or polyhalogenated (including perhalogenated) particularly with chloro or fluoro as for example trifluoromethyl, chlorodifluoromethyl, bromomethyl, 2,2,2-trifluoroethyl and pentafluoroethyl.

In the compounds of the present invention, the group Y corresponds to the residues of the penicillanic acid nucleus and ceph-3-em-4-carboxylic acid nucleus. The groups defined by T represent known cephalosporanic acid substituents and the groups or substituents defined by X, R and B similarly represent known molecular variations in penicillin and cephalosporin chemistry. Thus, when Y is the residue of the ceph-3-em-4-carboxylic acid residue, T can be hydrogen, hydroxy, lower alkanoyloxy of 2 to 5 carbon atoms, especially acetoxy or propionyloxy, pyridinium (in which case an inner salt is formed with the carboxylic acid group being anionic), or S-Het in which Het contains 5 or 6 ring members and 1 to 4, preferably 1 to 3 like or different hetero-atoms which can be oxygen, sulfur and/or nitrogen. The heterocyclic ring can be saturated but preferably is unsaturated, particularly with two double bonds. The heterocyclic ring can be unsubstituted or substituted by one or two substituents, as for example halo, preferably chloro or bromo, amino, lower alkylamino, di-lower alkylamino, lower alkyl, cycloalkyl, lower alkoxy, trifluoromethyl, phenyl, benzyl and lower alkanoylamido. The following are typical -S-Het groups:

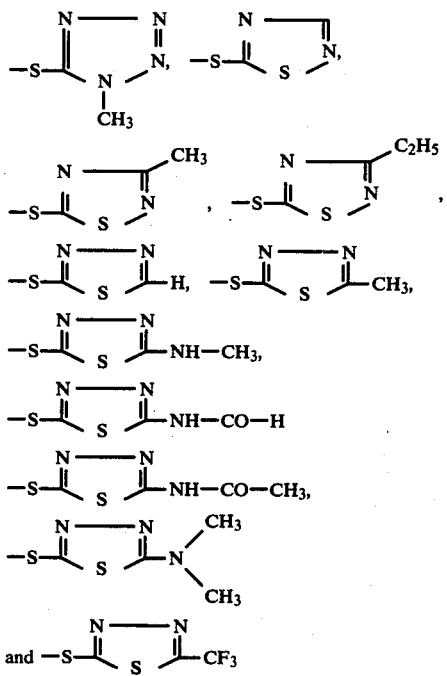

Particularly preferred among the S-Het groups are the tetrazolylthio and thiadiazolylthio groups unsubstituted or substituted by methyl, ethyl or trifluoromethyl.

When B is phenyl, it can be unsubstituted or substituted by one to three, especially one or two, like or different substituents, which can be in the o-, m- and/or p-position. Preferably there is at most one substituent which is in the p- or m-position. Examples of such substituents include hydroxy, halo, preferably fluoro, chloro or bromo, lower alkyl, preferably of 1 to 4 and especially of 1 to 2 carbon atoms; cyano; and methylsulfonyl. Substituted phenyl groups which can be mentioned in particular are the hydroxyphenyl radical, preferably p-hydroxyphenyl, methylphenyl, preferably p-methylphenyl, cyanophenyl, preferably m-cyanophenyl and p-cyanophenyl, methylsulfonylphenyl, preferably p-methylsulfonylphenyl, and fluorophenyl, preferably o-fluorophenyl and m-fluorophenyl.

R is preferably hydrogen and X is preferably S.

The substituents $R^1$ and $R^2$ can be like or different and include lower alkyl which can be optionally substituted. Preferably these alkyl groups will contain 1 to 4 carbon atoms as for example methyl, ethyl, n-propyl, isopropyl, n-butyl, isobutyl, sec-butyl and tert.-butyl.

$R^1$ and $R^2$ can also be straight-chain or branched alkenyl of 2 to 6, especially 2 to 4 carbon atoms, such as optionally substituted ethenyl, propen-1-yl, propen-2-yl and buten-3-yl.

$R^1$ and $R^2$ can also be optionally substituted cycloalkyl, cycloalkenyl and cycloalkadienyl, either monocyclic, bicyclic or tricyclic of 3 to 10, especially 3, 5 or 6 carbon atoms. Examples which can be mentioned are cyclopropyl, cyclobutyl, cyclopentyl, cyclopentenyl, cyclohexyl, cyclohexenyl, cyclohexadienyl, cycloheptyl, bicyclo[2.2.1]heptyl, bicyclo[2.2.2]octyl and adamantyl.

$R^1$ and $R^2$ can also be aryl of 6 to 10 carbon atoms in the aryl part, as for example optionally substituted phenyl, naphthyl, quinol-4-yl, benzothiazol-2-yl, and the like.

$R^1$ and $R^2$ can also be optionally substituted aralkyl of 6 or 10, especially 6, carbon atoms in the aryl portion and preferably 1 to 4, especially 1 or 2, carbon atoms in the alkyl portion, which may be straight-chain or branched. Optionally substituted benzyl and phenylethyl can be mentioned as examples.

When either or both of $R^1$ and $R^2$ is alkyl, alkenyl, cycloalkyl, cycloalkenyl, cycloalkadienyl, aryl or aralkyl, the group can carry one to three, especially one or two, identical or different substituents (hereinafter defined as $R^3$). It is preferred however that $R^1$ and $R^2$ are unsubstituted or at most contain one substituent.

$R^1$ and $R^2$ can also be optionally substituted heterocyclyl, namely a heteroparaffinic, heteroaromatic or heteroolefinic 5- to 7-membered ring, preferably 5- or 6-membered, with 1 to 3, especially 1 or 2, identical or different hetero-atoms. Hetero-atoms are oxygen, sulfur or nitrogen. Optionally substituted thienyl, furyl, oxazolyl, isoxazolyl, thiazolyl, isothiazolyl, pyrrolyl, imidazolyl, pyrazolyl, oxadiazolyl, thiadiazolyl, triazolyl, oxatriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2yl and pyron-4-yl are examples.

These heterocyclyl groups can carry one to three, especially one or two, identical or different substituents (hereinafter defined as $R^4$). It is preferred however that the heterocyclyl group is unsubstituted or at most contain one substituent.

The substituent $R^3$ can be halo, preferably fluoro, chloro or bromo; amino; lower alkylamino, methylamino or ethylamino, especially methylamino; di(-lower alkyl)amino, preferably dimethylamino or diethylamino; pyrrolidyl; piperidyl; formamido; lower alkanoylamido such as acetamido; H—CO—N—(lower alkyl)-, preferably H—CO—N(CH$_3$)— or H—CO—N(C$_2$H$_5$)—; lower alkyl—CO—N—(lower alkyl)—, preferably CH$_3$—CO—N(CH$_3$)—; (lower alkyl)$_2$C—N—; lower alkyl—SO$_2$—NH—, preferably CH$_3$—SO$_2$—NH—to and C$_2$H$_5$—SO$_2$—NH—, and especially CH$_3$—SO$_2$—NH—; lower alkyl—SO$_2$—N—(lower alkyl)—, preferably CH$_3$—SO$_2$—N(CH$_3$)—; HO—SO$_2$—NH—; HO—SO$_2$—N(lower alkyl)-, preferably HO—SO$_2$—N(CH$_3$)— and HO—SO₂—N(C₂H₅)—; amidino; (lower alkyl)-₂—N—CH=N—, especially (CH₃)₂N—CH=N—; pyrrolidino—CH=N—, guanido, nitro, azido, hydroxyl, lower alkyloxy, preferably CH₃—O— and C₂H₅—O—, especially CH₃O—; H—CO—O; lower alkyl—CO—O—, preferably CH₃—CO—O, C₂H₅—CO—O— and (CH₃)₃C—CO—O—; lower alkyl—O—CO—O—, preferably CH₃—O—CO—O—, C₂H₅—O—CO—O— and (CH₃)₃C—O—CO—O; H₂N—CO—O—; lower alkyl—NH—CO—O—, preferably CH₃NH—CO—O and C₂H₅—NH—CO—O—; (lower alkyl)₂N—CO—O—, preferably (CH₃)₂N—CO—O—, (C₂H₅)₂N—CO—O—, pyrrolidino—COO— and H₂N—SO₂—O—; lower alkyl—NH—SO₂—O—, preferably CH₃—NH—SO₂—O— and C₂H₅—NH—SO₂—O—; (lower alkyl)₂N—SO₂—O—, preferably (CH₃)₂N—SO₂—O— and (C₂H₅)₂N—SO₂—O—; HOOC— and H₂N—CO—; (lower alkyl)₂N—CO—, especially (CH₃)₂N—CO— and (C₂H₅)₂N—CO—; OHC—; HO—SO₂—O—and HS—; lower alkyl—S—, preferably CH₃—S—, CF₃—S—, C₂H₅—S—and (CH₃)₂CH—S—;

lower alkyl—S(=O)—, preferably CH₃—S(=O)— and C₂H₅—S(=O)—;

lower alkyl—SO₂—, preferably CH₃—SO₂—, CF₃SO₂— and C₂H₅—SO₂—; the group H₂N—SO₂—; lower alkyl—NH—SO₂—, preferably CH₃—NH—SO₂— and C₂H₅—NH—SO₂—; (lower alkyl)₂N—SO₂—, preferably (CH₃)₂N—SO₂— and (C₂H₅)₂N—SO₂—; pyrrolidinosulfonyl, the HO—SO₂—S— group; straight-chain or branched alkyl with 1 to 6 carbon atoms, especially methyl, ethyl, propyl, isopropyl, n-butyl, sec.-butyl or tert.-butyl, preferably methyl; furyl-2, and phenyl or phenoxy.

The substituent R⁴ can be lower alkyl, preferably methyl, ethyl and isopropyl and especially methyl; cycloalkyl with 3 to 7, preferably 3 to 6, carbon atoms, especially cyclopropyl; trifluoromethyl, halo, preferably fluoro, chloro or bromo; nitro; amino; lower alkylamino, preferably CH₃—NH— and C₂H₅—NH—; di-lower alkylamino, preferably (CH₃)₂N— and (C₂H₅)₂N—; formylamino; acetylamino; CH₃—O—CO—NH— and C₂H₅O—CO—NH—; CH₃—SO₂—NH—; hydroxyl, methoxy and ethoxy; methylthio and ethylthio; CH₃—SO₂—; CH₃—SO—; lower alkyl—NH—SO₂—, preferably CH₃—NH—SO₂—; lower alkoxy—CH₂—, especially CH₃O—CH₂— and C₂H₅O—CH₂—; heterocyclyl-aldimino, especially furyl-2-aldimino; alkenyl, sespecially allyl; and 2-fur-1-ylethylene; HOOC—; HO₃S—; lower alkyl-NHSO₂—, especially CH₃—NH—SO₂—; (lower alkyl)₂NSO₂—, especially (CH₃)₂NSO₂; HCO—; lower alkyl—CO—, preferably CH₃—CO—; lower alkyl—O—CO—, preferably CH₃—O—CO— and C₂H₅O—CO—; and —CN; lower alkyl—O—CO—CH₂—, preferably CH₃—O—COCH₂O or C₂H₅OCOCH₂—; (lower alkyl—O)₂-CH—, preferably (C₂H₅O)₂CH—; HO—lower alkyl—, preferably HO—CH₂—, (CH₃)₂C(OH)— and CH₃—CH(OH)—;

thienyl, furyl, oxazolyl, isoxazolyl, thiazolyl, isothiazolyl, pyrrolyl, imidazolyl, pyrazolyl, oxadiazolyl, thiadiazolyl, triazolyl, oxatriazolyl, thiatriazolyl, tetrazolyl, pyridyl, pyrazinyl, pyrimidinyl, tetrahydrofuranyl, dioxanyl, pyrrolidinyl, piperidinyl and morpholinyl, preferably furyl.

When R⁴ is present as a substituent on one or more nitrogen atoms in a nitrogen-containing heterocyclyl radical R¹ and R², it is lower alkyl, preferably methyl, ethyl, propyl and isopropyl, especially methyl and ethyl; the —C≡N group; —CHO; —COO—lower alkyl, preferably —COO—CH₃, —COOC₂H₅, —COOCH(CH₃)₂ and —COO—C(CH₃)₃; —CO—NH₂; —CO—NH—lower alkyl, preferably —CO—NH—CH₃, —CO—NH—C₂H₅ and —CO—NH—CH(CH₃)₂; and —CO—lower alkyl, preferably —CO—CH₃, —CO—C₂H₅ and —CO—CH(CH₃)₂.

R¹ and R² together with the carbon atom to which they are bonded can also be a saturated or unsaturated ring of 3 to 7 ring members. Unsaturated rings preferably contain 1 or 2 double bonds. The rings can contain one or two, preferably one hetero-atom such as oxygen, sulfur and/or nitrogen or hetero-groups such as sulfoxide and lower alkylimino. In the case of 6-membered rings, preferably one hetero-atom or one hetero-group is in the 4-position, relative to the carbon atom to which R¹ and R² are bonded. The following can be mentioned as particularly preferred rings:

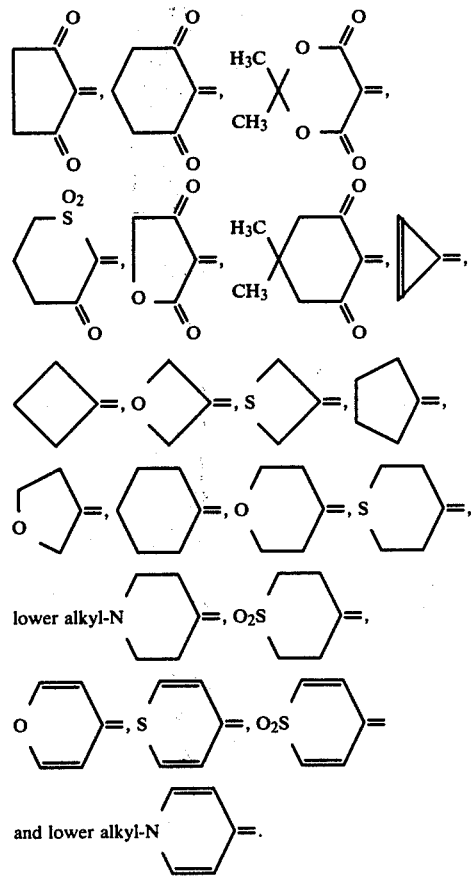

The foregoing rings in which R¹ and R² are taken conjointly with the carbon atom to which are bound can contain one to three, especially one or two, like or different substituents (hereinafter designated as R⁵). R⁵ can be halo, preferably fluoro, chloro or bromo; hydroxyl; lower alkoxy, preferably methoxy or ethoxy; lower alkylthio, preferably methylthio or ethylthio;

amino; lower alkylamino, preferably CH₃—NH— or C₂H₅—NH—; di(lower alkyl)amino, preferably dimethylamino or diethylamino; cyano; carboxy, carbo(lower alkoxy) such as carbomethoxy and carbethoxy, or lower alkyl, preferably methyl or ethyl.

In a first embodiment, the present invention pertains to compounds of Formula I, and their salts in which
R is hydrogen;
A is ethylene;
B is phenyl, hydroxyphenyl, chlorophenyl, fluorophenyl, methylphenyl, cyanophenyl, methylsulfonylphenyl, or cyclohexa-1,4-dien-1-yl;
X is S; and
Y is

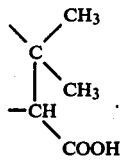

In a second embodiment, the invention pertains to compounds of Formula I, and their salts in which
R is hydrogen;
A is ethylene;
B is phenyl, hydroxyphenyl, chlorophenyl, fluorophenyl, methylphenyl, cyanophenyl, methylsulfonylphenyl or cyclohexa-1,4-dien-1-yl;
X is S; and
Y is

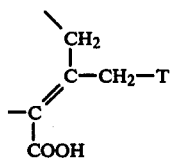

in which T is hydrogen, hydroxy, lower alkanoyloxy, pyridinium or a tetrazolylthio or thiadiazolylthio group unsubstituted or substituted by methyl, ethyl or trifluoromethyl.

Particularly preferred within this second embodiment in which T is hydrogen, hydroxy, acetoxy, 3-methyl-1,2,4-thiadiazol-5-ylthio, 1-methyltetrazol-5-ylthio or 5-trifluoromethyl-1,3,5-thiadiazol-2-ylthio.

In a further embodiment, the invention pertains to the compounds of the above recited first and second embodiment in which Z is R¹—CH=N— in which R¹ is a pyridyl, pyronyl, styryl or phenyl group unsubstituted or substituted by one or two substituents selected from the group consisting of fluoro, chloro, bromo, lower alkyl, lower alkoxy, nitro, cyano, lower alkylsulfonyl or carbo(lower alkoxy).

In still a further embodiment, the invention pertains to the compounds of the above recited first and second embodiments in which Z is R¹—CH=N— in which R¹ is a thienyl or furyl group unsubstituted or substituted by one or two substituents selected from the group consisting of fluoro, chloro, bromo, lower alkyl, lower alkylsulfonyl, lower alkylthio, carbo(lower alkoxy), lower alkanoyloxy and lower alkanoyloxymethyl.

In still a further embodiment, the invention pertains to the compounds of the above recited first and second embodiments in which Z is R¹—CH=N— in which R¹ is methylisoxazolyl.

The compounds of the present invention are prepared by allowing a compound of the formula:

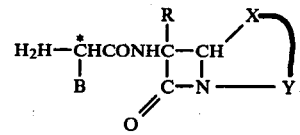
II in which R, B, X and Y are as herein defined, or a salt thereof to react in the presence of a solvent and at a temperature of from about −20° C. to about +50° C. with a reactive nucleofugic derivative of an acid of the formula:

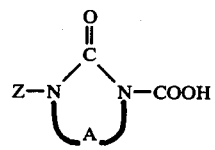
III wherein Z and A are as herein defined.

When the by-product of this reaction is acid, the reaction is conducted in the presence of an acid binding agent, as is more fully described below.

It will be recognized that the compounds of Formula II represent a known class of compounds. Many of these are commercially available or are obtainable according to known methods. Examples include α-aminobenzylpenicillin, α-amino-p-hydroxybenzylpenicillin, α-amino-p-methylbenzylpenicillin, α-amino-p-chlorobenzylpenicillin, 6-[2-amino-2-(1,4-cyclohexadien-1-yl)-acetamido]-penicillanic acid, 7-(α-aminophenylacetamido)-3-methylceph-3-em-4-carboxylic acid and 7-(α-aminophenylacetamido)-3-acetoxymethylceph-3-em-4-carboxylic acid. All the various crystal forms, hydrate forms and salts of the compounds of Formula II are suitable for use as starting materials. It is preferable when salts are used to employ those in which the cation is one which is among those suitable for the final β-lactam. Sodium salts are particularly preferred.

The reactive nucleofugic derivatives of the acids of Formula III can be readily prepared according to known methods [see e.g. JACS, 78 (1956) p 5349 et seq.]. These methods, which are described below in greater detail, involve introduction of an amino group in a known 1,3-diazacycloalkan-2-one such as imidazolidin-2-one, 1,3-diazacycloheptan-2-one or benzimidazolin-2-one, formation of a Schiff base and introduction of a nucleofugic carboxylic acid group such as chlorocarbonyl. The overall route can be exemplified by the following:

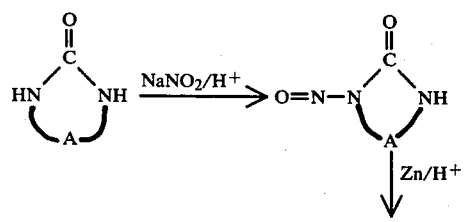

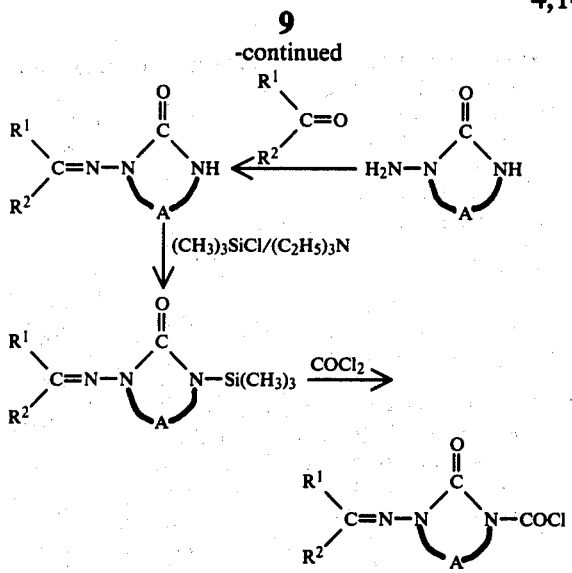

In addition to halo of halocarbonyl, other nucleofugic groups, such as are described for example in Angew. Chem., 81 (1969) 543 et seq., can be employed. For example, the azido compound can be obtained through treatment of the acid chloride with an alkali metal azide to yield the azidocarbonyl compound. Typical of the reactive nucleofugic derivatives of the acids of Formula III are 1-chlorocarbonyl-2-oxo-3-benzaliminoimidazolidine, 1-azidocarbonyl-2-oxo-3-benzalimino-imidazolidine, 1-chlorocarbonyl-2-oxo-3-(4-chloro)-benzalimino-imidazolidine, 1-chlorocarbonyl-2-oxo-3-(4-methoxy)-benzalimino-imidazolidine, 1-chlorocarbonyl-2-oxo-3-(4-nitro)-benzalimino-imidazolidine, 1-chlorocarbonyl-2-oxo-3-(4-cyano)-benzalimino-imidazolidine, 1-chlorocarbonyl-2-oxo-3-(4-methylsulphonyl)-benzalimino-imidazolidine, 1-chlorocarbonyl-2-oxo-3-(thiophen-2-aldimino)-imidazolidine, 1-azidocarbonyl-2-oxo-3-(thiophen-2-aldimino)-imidazolidine, 1-chlorocarbonyl-2-oxo-3-(furan-2-aldimino)-imidazolidine and 1-azidocarbonyl-2-oxo-3-(furan-2-aldimino)-imidazolidine.

Diluents which can be used in the process according to the invention are water and all inert organic solvents, preferably those which are water-miscible. These include, lower alkanones, for example acetone and methyl ethyl ketone; cyclic ethers, for example tetrahydrofuran and dioxane; nitriles, for example acetonitrile; lower dialkylformamides, for example dimethylformamide; lower alkyl alcohols, for example ethanol and isopropanol; dimethylsulfoxide and the like. These solvents can also be used as mixtures with one another and also as any desired mixtures of one or more of these solvents with water. The process according to the invention can thus be carried out in the presence of (a) exclusively water, (b) exclusively one or more organic solvents or (c) water and one or more organic solvents. If, because of the presence of water, it is possible to measure the pH during the reaction according to the invention, the pH of the reaction mixture is preferably kept at between 6.5 and 7.5 by adding bases or by using buffer mixtures. The process according to the invention can, however, also be carried out very readily in a different pH range, for example between 4.5 and 9.0, or at pH 2.0 to 4.5. Furthermore it is possible to carry out the reaction in water-immiscible solvents, for example halogenated hydrocarbons, such as chloroform or methylene chloride, with addition of organic bases, preferably lower alkylamines, for example triethylamine or diethylamine, or cyclic bases, for example N-ethylpiperidine. The reaction can also be carried out in a mixture of water and a water-immiscible solvent such as, for example, lower alkyl ethers, such as diethyl ether; halogenated hydrocarbons, such as chloroform and methylene chloride; carbon disulphide; isobutyl methyl ketone; esters, such as ethyl acetate; and aromatic hydrocarbons, such as benzene; in these cases it is advisable to stir the mixture vigorously and to keep the pH value between 4.5 and 9.0 or, for example, 2.0 and 4.5, by adding bases or by using customary buffer solutions, for example phosphate, acetate or citrate buffers. The reaction can, however, also be carried out in water alone, in the absence of organic solvents, in the presence of an organic or inorganic base, or with addition of customary buffer substances.

All acid-binders usually employed in the chemistry of the antibiotics can be used as the acid-binding agents. These include inorganic bases and organic bases which are difficult to acylate, for example as a result of steric hindrance. Sodium hydroxide and potassium hydroxide are examples of inorganic bases. Organic bases include practically all open-chain or cyclic amines and heteroaromatic bases, which cannot be acylated or at least are difficult to acylate. Examples of organic bases include tertiary amines, preferably lower alkylamines such as triethylamine, heteroaromatic bases, such as pyridine, and dicyclohexylamine, secondary amines which are difficult to acylate.

The addition of a base in the process is only necessary if acid compounds are produced during the reaction, for example if the reactive nucleofugic group is halo or azido.

The reaction temperatures can be varied within a substantial range and generally are between from about $-20°$ C. to about $+50°$ C., preferably between $0°$ C. and $+20°$ C. However, as with most chemical reactions, higher or lower temperatures can also be used in principle. The reaction is normally carried out under normal pressure but reduced pressure or elevated pressure can also be employed. The proportions of the reactants can be varied within wide limits without adversely influencing the result. For example, the starting materials can be reacted with one another in equimolecular amounts. However, it can be expedient to use one of the two reactants in excess in order to facilitate the purification, or preparation in a pure form, of the desired penicillin, and to increase the yield. For example, the reactants of Formula II can be employed in an excess of 0.1 to 0.3 mol equivalents and diminished decomposition of the reactants of Formula III in an aqueous solvent mixture can thereby be achieved. The excess of the reactants of Formula II can easily be removed on working up the reaction mixture, because of the ready solubility in aqueous mineral acids. On the other hand, however, it is also possible to advantageously employ the reactants of Formula III in an excess of, for example, 0.1 to 1.0 mol equivalents. This results in better utilization of the reactants of Formula II and compensates for the decomposition of the reactants of Formula III which takes place as a side-reaction in aqueous solvents. Since the excess of the compounds of Formula III is rapidly converted in water to neutral nitrogen-containing heterocyclic compounds, which can easily be removed, the purity of the final antibiotics remains intact. The amount of base to be used can be decided, for example, by the desired maintenance of a particular pH value.

Where a pH measurement and adjustment is not carried out, not possible, nor meaningful, as for example due to the absence of sufficient amounts of water in the diluent, 2 mol equivalents of base are preferably added.

The processing and purification of the reaction batches to yield the final compounds and/or their salts is carried out in the manner generally known for these compounds. Isolation and purification of the compounds according to the invention, and the liberation of the free acids from salts or the conversion of the free acids into salts are also carried out in accordance with generally customary methods of organic chemistry which are familiar to the art.

Compounds whih contain the group

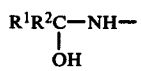

as Z, are produced when this radical is already contained in the compounds of Formula III, or can be produced if the reaction is carried out in aqueous solvents.

Non-toxic, pharmaceutically acceptable salts of the compounds of Formula I are those formed between inorganic and organic bases and the acid carboxyl group or at the acid carboxyl and sulfonic acid groups. Bases which can be employed for this purpose include all bases usually employed in pharmaceutical chemistry, especially in the chemistry of the antibiotics. Examples of inorganic bases which may be mentioned are alkali metal and alkaline earth hydroxides, alkali metal and alkaline earth metal carbonates and alkali metal bicarbonates, such as sodium hydroxide and potassium hydroxide, calcium hydroxide and magnesium hydroxide, sodium carbonate and potassium carbonate, calcium carbonate, sodium bicarbonate and potassium bicarbonate; aluminium hydroxide and ammonium hydroxide. Organic amines include primary, secondary and tertiary aliphatic amines as well as heterocyclic amines. Examples which may be mentioned are: di- and tri-(lower alkyl)amines, for example diethylamine, triethylamine, tri-$\beta$-hydroxyethylamine, procaine, dibenzylamine, N,N'-dibenzylethylenediamine, N-benzyl-$\beta$-phenylethylamine, N-methylmorpholine and N-ethylmorpholine, l-ephenamine, dehydroabietylamine, N,N'-bis-dehydroabietylethylenediamine, and N-lower alkyl-piperidine. So-called basic aminoacids such as lysine or arginine can also be used advantageously as bases. A particularly preferred salt is the sodium salt.

The $\beta$-lactams of Formula I, in the form of the free acid, have the same type of antibacterial action whether they are crystalline or amorphous and whether they are anhydrous or in various hydrated forms. Equally, these compounds have the same type of antibacterial action in the form of their salts, for example the sodium salts, whether they are crystalline or amorphous and whether they are anhydrous or contain water, for example through being in the form of a hydrate. Different forms may be more desirable from the standpoint of formulation but are nevertheless antibacterially equivalent.

Typical species of the present invention, as the $\beta$-lactam free acid, are presented in the following tables.

Table No. 1

| | | |
|---|---|---|
| IA. $R^1 =$ (phenyl with $R^5$), $R^2 = H$, $B =$ (phenyl with $R^6$) | | |
| $R^5$ | | $R^6$ |
| H | | H |
| 4-Cl | | 4-HO— |
| 4-CH$_3$O | | H |
| 4-NO$_2$ | | H |
| 4-CN | | H |
| 4-CH$_3$SO$_2$ | | H |
| 4-CH$_3$SO$_2$ | | 4-HO— |

| | | |
|---|---|---|
| IB. $R^1 =$ (furyl with $R^7$, $R^8$), $R^2 = H$, $B =$ (phenyl with $R^6$) | | |
| $R^7$ | $R^8$ | $R^6$ |
| H | H | H |
| H | H | 4-OH |
| H | CH$_3$ | H |
| H | C$_2$H$_5$ | H |
| H | i-C$_3$H$_7$ | H |
| H | cyclopropyl | H |
| H | CH$_3$OCH$_2$ | H |
| H | C$_2$H$_5$OCH$_2$ | H |
| H | (C$_2$H$_5$O)$_2$CH | H |
| H | CH$_3$S | H |
| H | CH$_3$O | H |
| H | C$_2$H$_5$O | H |
| H | OHC— | H |

Table No. 1-continued
| | | |
|---|---|---|
| H | O₂N | H |
| H | CH₃SO₂ | H |
| H | CH₃CO | H |
| H | CH₃OCOCH₂ | H |
| H | CH₃OCO | H |
| H | C₂H₅OCO | H |
| H | F | H |
| H | Cl | H |
| H | Br | H |
| H | CH₃SO₂NH | H |
| i-C₃H₇ | H | H |
| H | HOCH₂ | H |
| H | CH₃NHSO₂ | H |
| H |  | H |
IC. R¹ = as below, R² = H, B = 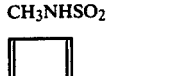
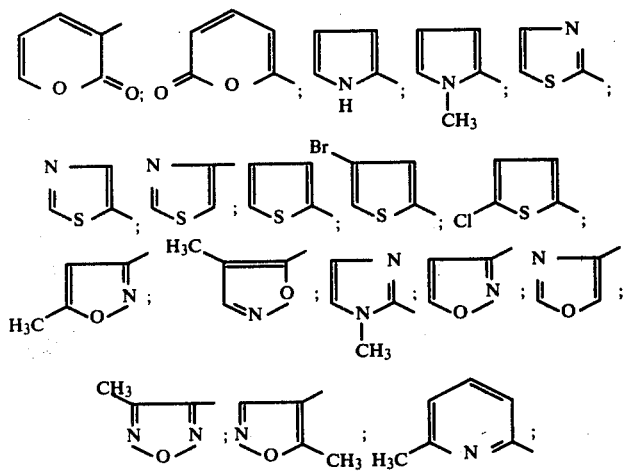
CH₃; C₂H₅; i-C₃H₇; —; CH₃—CH=CH; (CH₃)₂NCO—;
II  R¹, R² = as below; B = 
| R¹ | R² |
|---|---|
| CH₃ | CH₃ |
| CH₃ |  |
|  |  |
| CF₃ | C₂H₅ |
| Cyclohexyl | H |
| | H |
|  | |
III  R¹ = see below, R² = H, B = 
| R¹ |
|---|
| C₆H₅ |
| 4-CH₃OC₆H₅ |

Table No. 1-continued

4-CH₃SO₂C₆H₅

IV  R¹ + R² = see below, B = (phenyl)

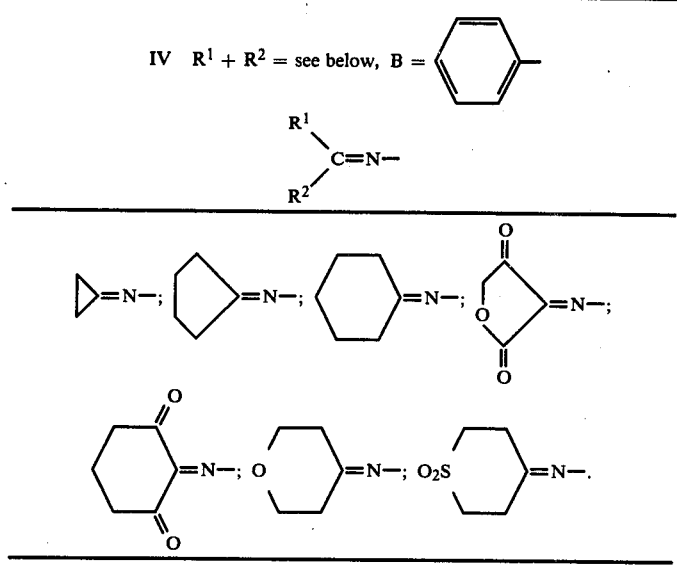

Table No. 2

(structure shown)

IA. R¹ = (phenyl with R⁵), R² = H, B = (phenyl with R⁶), T = OCOCH₃

| R⁵ | R⁶ |
|---|---|
| H | H |
| 4-Cl | 4-HO— |
| 4-CH₃O | H |
| 4-NO₂ | H |
| 4-CN | H |
| 4-CH₃SO₂ | H |
| 4-CH₃SO₂ | 4-HO— |

IB. R¹ = (furan with R⁷, R⁸), R² = H, B = (phenyl with R⁶), T = OCOCH₃

| R⁷ | R⁸ | R⁶ |
|---|---|---|
| H | H | H |
| H | H | 4-OH |
| H | CH₃ | H |
| H | C₂H₅ | H |
| H | i-C₃H₇ | H |
| H | (cyclopropyl) | H |
| H | CH₃OCH₂ | H |
| H | C₂H₅OCH₂ | H |
| H | (C₂H₅O)₂CH | H |
| H | CH₃S | H |
| H | CH₃O | H |
| H | C₂H₅O | H |
| H | OHC— | H |
| H | O₂N | H |
| H | CH₃SO₂ | H |
| H | CH₃CO | H |
| H | CH₃OCOCH₂ | H |
| H | CH₃OCO | H |

Table No. 2-continued
| | | |
|---|---|---|
| H | C₂H₅OCO | H |
| H | F | H |
| H | Cl | H |
| H | Br | H |
| H | CH₃SO₂NH | H |
| i-C₃H₇ | H | H |
| H | HOCH₂ | H |
| H | CH₃NHSO₂ | H |
| H |  | H |
IC. R¹ = as below, R² = H, B = 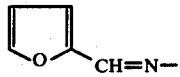, T = OCOCH₃
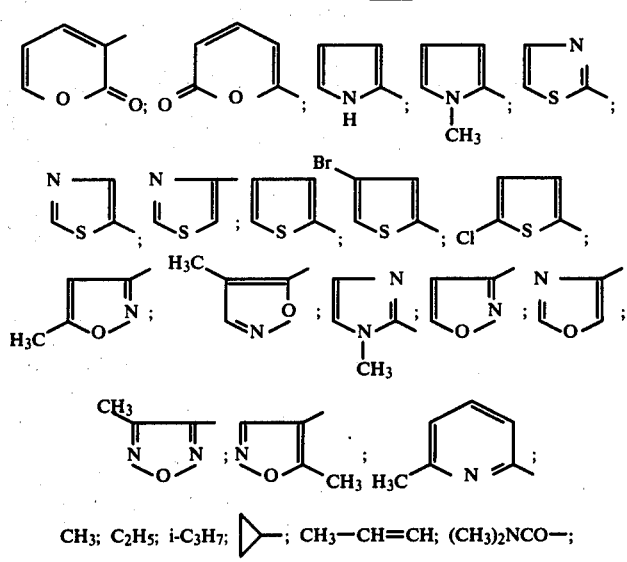
CH₃; C₂H₅; i-C₃H₇; —; CH₃—CH=CH; (CH₃)₂NCO—;
II  R¹, R² = as below; B = , T = OCOCH₃
| R¹ | R² |
|---|---|
| CH₃ | CH₃ |
| CH₃ |  |
|  | 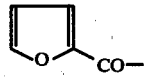 |
| CF₃ | C₂H₅ |
| Cyclohexyl | H |
| | H |
|  | |
III  R¹ = see below, R² = H, B = , T OCOCH₃
| R¹ |
|---|
| C₆H₅ |
| 4-CH₃OC₆H₅ |
| 4-CH₃SO₂C₆H₅ |

Table No. 2-continued

IV R$^1$ + R$^2$ = see below, B = 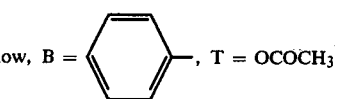, T = OCOCH$_3$

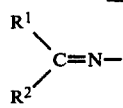

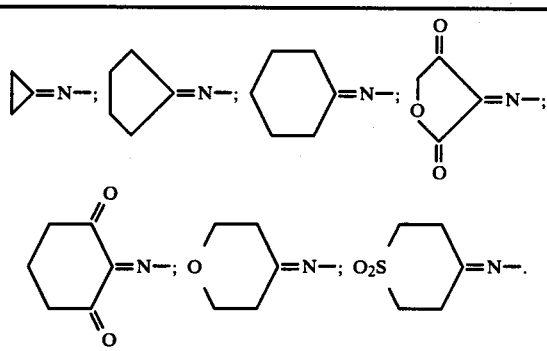

| V. R$^1$ = see below, R$^2$ = H, B = see below, T = see below | | |
|---|---|---|
| R$^1$ | B | T |
| fur-2-yl | phenyl | OH |
| 5-hydroxymethylfur-2-yl | phenyl | OH |
| 5-methylthiofur-2-yl | phenyl | OH |
| fur-2-yl | cyclohexa-1,4-dien-1-yl | OH |
| fur-2-yl | phenyl | H |

VI. R$^1$ + R$^2$ = see below, B = phenyl, T = OCOCH$_3$

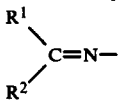

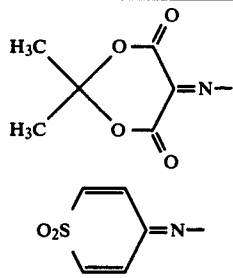

Preferred compounds of the present invention are those having the R-configuration (corresponding to the D-form) about the carbon atom designated C̽.

The active compounds according to the invention couple a strong and broad antimicrobial activity with a low toxicity. These properties permit their use as chemotherapeutic agents in medicine and as compounds for preserving inorganic and organic materials, in particular organic materials normally subject to bacterial infestation or growth such as polymers, lubricants, paints, fibres, leather, paper and timber, foodstuffs and water. The compounds are active against a broad spectrum of micro-organisms, including Gram negative and Gram positive bacteria and bacteria-like micro-organisms. They are therefore particularly suitable for the prophylaxis and chemotherapy of local and systemic infections, caused by these pathogens, in human medicine and veterinary medicine. Typical of such pathogens are the following:

Micrococcaceae, such as Staphylococci, for example *Staphylococcus aureus, Staph. epidermidis, Staph. aerogenes* and *Gaffkya tetragena* (Staph.=Staphylococcus);

Lactobacteriaceae, such as Streptococci, for example Streptococcus pyogenes, α- or β-haemolytic Streptococci, non-(γ)-haemolytic Streptococci, *Str. viridan, Str. faecalis (Enterococci), Str. agalactiae, Str. lactis, Str. equi, Str. anaerobis* and *Diplococcus pneumoniae* (Pneumococci) (Str.=Streptococcus);

Neisseriaceae, such as Neisseriae, for example *Neisseria gonorrhoeae* (Gonococci), *N. meningitidis* (Meningococci), *N. catarrhalis* and *N. flava* (N=Neisseria);

Corynebacteriaceae, such as Corynebacteria, for example *Corynebacterium diphtheriae, C. pyogenes, C. diphtheroides, C. acnes, C. parvum, C. bovis, C. renale, C. ovis* and *C. murisepticum, Listeria* bacteria, for example *Listeria monocytogenes, Erysipelothrix* bacteria, for example Erysipelothrix insidiosa and Kurthia bacteria, for example *Kurthia zopfil* (C.=Corynebacterium);

Mycobacteriaceae, such as pathogens of mycobacterioses, for example Mycobacterium tuberculosis, *M. bovis, M. avium,* and so-called atypical mycobacteria of the Runyon groups I, II, III and IV, and *M. leprae* (M. = Mycobacterium);

Enterobacteriaceae, such as Escherichiae bacteria of the Coli group: Escherichia bacteria, for example *Escherichia coli,* Enterobacter bacteria, for example *E. aerogenes* and *E. cloacae,* Klebsiella bacteria, for example *K. pneumoniae, K. pneumoniae* and *K. oxaenae,* Erwiniae, for example Erwinia spec., Serratia, for example *Serratia marcescens* (E. = Enterobacter) (K. = Klebsiella), *Proteae bacteria* of the Proteus group: Proteus, for example *Proteus vulgaris, Pr. morganli, Pr. rettgeri* and *Pr. mirabilis,* Providencia, for example Providencia sp. (Pr. = Proteus), Salmonelleae: Salmonella bacteria, for example *Salmonella paratyphi* A and *B, S. typhi, S. enteritidis, S. cholerae suis* and *S. typhi murium* (S. = Salmonella, and Shigella bacteria, for example *Shigella dysenteriae, Sh. ambigua, Sh. flexneri, Sh. boydii* and *Sh. sonnei* (Sh. = Shigella):

Pseudomonadaceae, such as Pseudomonas bacteria, for example *Pseudomonas aeruginosa* and *Ps. psuedomallei* (Ps. = Psuedomonas), and Aeromonas bacteria, for example *Aeromonas liquefaciens* and *A. hydrophila* (A.- = Aeromonas);

Spirillaceae, such as Vibrio bacteria, for example *Vibrio cholerae, V. proteus* and *V. fetus* (V. = Vibrio), and Spirillum bacteria, for example *Spirillum minus;*

Parvobacteriaceae or Brucellaceae, such as Pasteurella bacteria, for example *Pasteurella multocida, Past. pestis (Yersinia), Past. pseudotuberculosis* and *Past. tularensis* (Past. = Pasteurella), Brucella bacteria, for example *Brucella abortus, Br. melitensis* and *Br. suis* (Br. = Brucella), Haemophilus bacteria, for example *Haemophilus influenzae, H. ducreyi, H. suis, H. canis* and *H. aegypitcus* (H. = Haemophilus), Bordetella bacteria, for example *Bordetella pertussis and B. Bronchiseptica* (B. = Bordetella) and *Moraxella bacteria,* for example *Moraxella lacunata;*

Bacteroidaceae, such as Bacteroides bacteria, for example *Bacteroides fragilis* and *B. serpens* (B. = Bacteroides), Fusiforme bacteria, for example *Fusobacterium fusiforme,* and Sphaerophorus bacteria, for example *Sphaerophorus necrophorus, Sph. necroticus* and *Sph. pyrogenes* (Sph. = Sphaerophorus);

Bacillaceae, such as aerobic spore-forming organisms, for example *Bacillus anthracis* (*B. subtilis* and *B. cereus*) (B. = Bacillus) and anaerobic spore-forming Clostrdia, for example *Clostridium perfringens, Cl. specticium, Cl. oedematien, Cl. histolyticum, Cl. tetani* and *Cl. botulinum* (Cl. = Clostridium);

Spirochaetaceae, such as Borrelia bacteria, for example *Borrelia recurrentia* and *B. vincentii* (B. = Borrelia), Treponema bacteria, for example *Treponema pallidum, Tr. pertinue* and *Tr. carateum* (Tr. = Treponema) and Leptospira bacteria—*Leptospira interrogans,* for example *Leptospira icterohaemorrhagiae, L. canicola, L. grippotyphosa, L. pomona, L. mitis* and L. bovis (L. = Leptospira).

The compounds according to the invention can thus be used in the treatment of infectious conditions of the respiratory passages and of the pharyngeal cavity; otitis; pharyngitis; pneumonia; peritonitis; pyelonephritis; cystitis; endocarditis; systemic infections; bronchitis; arthritis; and various other local infections.

The compound of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refer to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle in which it is insoluble.

Fluid unit dosage forms for parenteral administration can be prepared by suspending or dissolving a measured amount of the compound in a non-toxic liquid vehicle suitable for injection such as an aqueous or oleaginous medium and sterilizing the suspension or solution. Alternatively a measured amount of the compound is placed in a vial and the vial and its contents are sterilized and sealed. An accompanying vial or vehicle can be provided for mixing prior to administration.

This invention further provides a method of combating (including prevention, relief and cure of) infections in human and non-human animals, which comprises administering thereto an antibacterially effective amount of a compound of the invention, along or in admixture with a diluent or in the form of a pharamaceutical composition according to the invention.

The β-lactam or a salt can be administered perorally, parenterally (for example intramuscularly, intraperitoneally or intravenously), rectally or locally, but preferably orally or parenterally. Preferred pharmaceutical compositions and medicaments are therefore those adapted for oral and parenteral administration.

The invention also includes, for use in veterinary medicine, medicated fodder comprising a compound according to the invention and a consumable carrier which can also be nutritious. Examples of suitable nutritious materials are oil cake, grains, such as barely, fish meal, soya bean meal, exhausted sugar beet chips, silage, hay and skimmed milk.

In general a suitable antibacterial effect both in human medicine and in veterinary medicine is observed upon administration of these compounds in total daily doses of from about 5 to about 1,000, preferably 20 to 300 mg/kg of body weight. Optionally, this can be in the form of several individual administrations, in order to achieve more consistent blood levels. An individual administration contains the active compound in amounts of from about 1 to about 250, especially of 10 to 100, mg/kg of body weight. However, it can be necessary to deviate from these guidelines and in particular to do so as a function of the nature and body weight of the subject to be treated, the nature and the severity of the illness, the nature of the preparation and of the administration of the medicine, and the time or interval over which the administration take place. Thus in some cases less than 5 mg/kg of active compound will give a suitable response while in other cases more than 1,000 mg/kg of active compound may be indicated. The particular optimum dosage should be in each case titrated to the particular individual and the type of administration determined by sound professional judgement.

When used as additives to feedstuffs, the new compounds, in the usual concentrations and preparations, can be administered together with the feedstuff or the feedstuff preparations, or in the drinking water. By these means, subchronic infections of Gram negative or Gram positive bacteria can be reduced, thereby promoting growth and improving feedstuff utilization.

In order to broaden the spectrum of action and enhance antibacterial activity, especially in the case of β-lactamase forming bacteria, the compounds can be combined with other antimicrobial active compounds, as for example penicillins such as oxacillin or dicloxacillin which are penicillinase-resistant. Similarly, the compounds of the invention can also be combined with aminoglycoside antibiotics, such as for example gentamicin, sisomicin, kanamicin, amikacin or tobramicin.

The activity of the β-lactam antibiotics according to the invention can be conveniently observed in recognized in vitro and in vivo models of which the following are typical.

1. In vitro experiments

Examples 1.3., 2.3. and 2.4., which can be regarded as typical representatives of the compounds according to the invention, were diluted with Muller-Hinton nutrient broth, with addition of 0.1% of glucose, to a content of 100 μg/ml. In each case, the nutrient solution contained $1 \times 10^5$ to $2 \times 10^5$ bacteria per milliliter. The tubes containing this mixture were in each case incubated for 24 hours and the turbidity was then determined. Freedom from turbidity indicates that the compound is active. At a dosage of 100 μg/ml the following bacterial cultures were free from turbidity (sp. = species):

*Klebsiella pneumoniae; Enterobacter aerogenes* sp.; Providencia; *Serratia marcescens; E. coli BE;* Salmonella sp.; Shigella sp.; Proteus, indole-negative and indole-positive; *Pasteurella pseudotuberculosis;* Brucella sp.; *Haemophilus influenzae; Bordetella bronchiseptica; Staphylococcus aureus* 133; *Neiserria catarrhalis* sp.; *Diplococcus pneumoniae* sp.; *Streptococcus pyogenes W.;* Enterococcus sp.; Lactobacillus sp.; *Corynebacterium diphteriae gravis; Corynebacterium pyogenes M; Clostridium tetani; Pseudomonas aeruginosa* sp.; *Bacteroides fragilis* sp.;

2. In vivo experiments

Table 1 which follows shows the action of one of the compounds according to the invention against a range of bacteria in animal experiments with white mice. The white mice, of the $CF_1$ strain, were infected intraperitoneally with the species of bacteria stated in each case.

Table 1

| Animal experiments with white mice | |
|---|---|
| Determination of the $ED_{100}$ after 24 hours | |
| Microorganism | Dose in mg of the β-lactam antibiotic from Examples 1.3., 2.3. and 2.4. per kg of body weight (administered subcutaneously) |
| *Escherichia coli* C 165 | 2 × 150 |
| *Klebsiella* 63 | 2 × 150 |

Therapy: administered twice, 30 and 90 minuts after infection. The $ED_{100}$ is the dose at which 100% of the infected animals still survive after 24 hours.

The process according to the invention is illustrated by the examples which follow.

The α-aminobenzyl-penicillin used in the examples which follow contained about 14% of water but anhydrous α-aminobenzyl-penicillin [compare U.S. Pat. No. 3,144,445] can be used equally well.

The α-amino-p-hydroxybenzylpenicillin used in the examples contained about 13% of water but anhydous α-amino-p-hydroxybenzylpenicillin can be used equally well.

The 6-[2-amino-2-(1,4-cyclohexadien-1-yl)-acetamido-]penicillanic acid used in the examples was substantially anhydrous.

The 7-(α-amino-phenylacetamido)-3-methyl-ceph-3-em-4-carboxylic acid used in the examples contained about 5% of water but anhydrous 7-(α-amino-phenylacetamido)-3-methyl-ceph-3-em-4-carboxylic acid can be used equally well.

The 7-(α-amino-phenylacetamido)-3-acetoxymethyl-ceph-3-em-4-carboxylic acid used in the examples contained 8% of water but anhydrous 7-(α-aminophenylacetamido)-3-acetoxymethyl-ceph-3-em-4-carboxylic acid can be used equally well.

The water content of the starting compounds is immaterial with regard to carrying out the process according to the invention.

"AMpicillin" denotes the particular α-aminobenzyl-penicillin which has the D=R-configuration in the side chain, "amoxicillin" denotes the particular α-amino-p-hydroxy-benzylpenicillin which has the D=R-configuration in the side chain, and "epicillin" denotes the particular α-amino-α-(1,4-cyclohexadien-1-yl)-methyl-penicillin which has the D=R-configuration in the side chain.

"Cefalexin" denotes the particular 7-(α-amino-phenylacetamido)-3-methyl-ceph-3-em-4-carboxylic acid with the D=R-configuration in the side chain and "cephaloglycine" denotes the particular 7-(α-amino-phenylacetamido)-3-acetoxymethyl-ceph-3-em-4-carboxylic acid with the D=R-configuration in the side chain.

The NMR spectra of the compounds according to the invention were recorded in CD₃OD solution, unless stated otherwise. The designation in brackets denote the following:

| s = singlet | q = quartet |
| d = doublet | m = multiplet |
| t = triplet | AB = AB system |

The IR spectra of the compounds accordind to the invention were recorded in paraffin oil suspensions, unless stated otherwise.

Explanation of the abbreviations used in the examples:

| vol. | = volume |
| pts. by wt. | = parts by weight |
| pts. by vol. | = parts by volume |
| hrs. | = hours |
| hr. | = hour |
| THF | = tetrahydrofurane |
| DMF | = dimethylformamide |
| ether | = diethyl ether |
| ethyl acetate | = acetic acid ethyl ester |
| room temperature | = approx. 20° C. |
| abs. | = absolute |

Part 1.3.

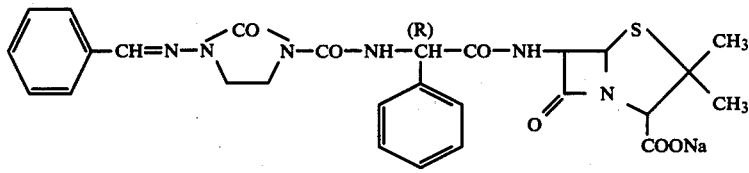

| dec. pt. | = decomposition point |

The yields quoted in % denote yields in % of theory.

EXAMPLE 1

Part 1.1.

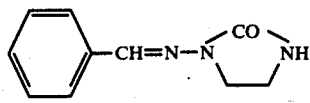

2-Oxo-imidazolidine (31.5 pts. by wt.) is dissolved in 2 N sulphuric acid (1,000 pts. by vol.), the solution is cooled to 3°-6° C., a solution of sodium nitrite (25.25 pts. by wt.) in water (50 pts. by vol.) is added dropwise over the course of 13 minutes while stirring, and continuing to cool, the mixture is then stirred for a further 1.5 hrs. in an ice bath and purified zinc dust (55 pts. by wt.) is then introduced in the course of one hour. The mixture is stirred for a further 0.5 hr. while cooling with ice and then for a further hr. at room temperature. The unconverted zinc is then filtered off and washed with a little water, benzaldehyde (35 pts. by wt.) is added to the combined filtrates and the mixture is stirred vigorously for 0.5 hr. The 1-benzalimino-2-oxo-imidazolidine which has precipitated is then filtered off and recrystallised, after drying (49.2 pts. by wt.; melting point=194°-200° C.) from ethanol.

Yield 41.4 pts. by wt., melting point=202° C.

IR spectrum: 1,720 cm⁻¹(C=O).

calculated: C 63.5; H 5.9; N 22.2; found: C 64.1; H 5.7; N 22.7.

Part 1.2.

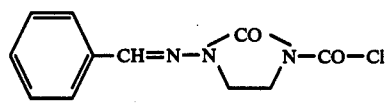

A mixture of 1-benzalimino-2-oxo-imidazolidine (11.7 pts. by wt.) (see 1.1.), benzene (120 pts. by vol.) and triethylamine (13.8 pts. by vol.) is heated to the boil and a solution of trimethylchlorosilane (10 pts. by wt.) in benzene (50 pts. by vol.) is then added dropwise over the course of 1 hr., while stirring. The mixture is then kept at the boil for a further 5.5 hrs., and the triethylammonium hydrochloride which has separated out is filtered off hot and washed with hot benzene. A solution of phosgene (6.2 pts. by wt.) in benzene (30 pts. by vol.) is added to the cooled, combined benzene filtrates. The mixture is left standing well-sealed overnight at room temperature. Excess phosgene present is then very largely removed by means of a dry stream of air. The 1-chlorocarbonyl-2-oxo-3-benzalimino-imidazolidine is filtered off and dried.

Yield 8.9 pts. by wt., melting point=250°-252°, with decomposition.

IR spectrum: 1,800 cm⁻¹ (—CO—Cl)

calculated: C 52.5; H 4.0; Cl 14.1; N 16.7; found: C 51.8; H 5.6; Cl 14.6; N 16.8.

Ampicillin (14 pts. by wt.) is suspended in 80% strength aqueous tetrahydrofurane (140 pts. by vol.) and dissolved by means of the minimum amount of triethylamine required (the pH is then 8.0); 1-chlorocarbonyl-2-oxo-3-benzalimino-imidazolidine (7.8 pts. by wt.) (see 1.2.) is introduced slowly, while stirring, and at the same time the pH is kept at 7.0-7.5 by appropriate addition of triethylamine. The mixture is then stirred further for as long as triethylamine still has to be added in order to maintain the stated pH range (about 1-2 hrs.). The mixture is diluted with water (200 pts. by vol.), the pH was adjusted to 6.5, the the tetrahydrofurane is largely evaporated off in vacuo, the aqueous solution which remains is washed once with ether in a separating funnel, then covered with ethyl acetate, and acidified to pH 2 with dilute HCl, while stirring. The organic phase is then separated off, washed with saturated NaCl solution, dried over MgSO₄, diluted with an equal volume of ether, and treated with an approx. 1-molar sodium 2-ethylhexanoate solution in ether containing methanol, until precipitation ceases. The sodium 6-{D-α-[(2-oxo-3-benzalimino-imidazolidin-1-yl)-carbonylamino]-phenylacetamido}-penicillanate is filtered off, washed with ether and then with a mixture of ether and methanol (5–10%) and isopropanol, and dried.

Yield 6.2 pts. by wt., β-lactam content 91%.

According to the NMR spectrum, the substance still contains 2.5 mols of H₂O, 0.1 mol of isopropanol and 0.04 mol of sodium 2-ethyl-hexanoate. This was taken into account in the calculated analytical data.

calculated: C 51.5; H 5.3; N 13.0; S 5.0; found: C 50.9; H 5.2; N 12.9; S 5.1.

NMR signals at τ (in CD₃OD)=2.1–2.8 (11H); 4.3–4.65 (3H); 5.8 (1H); 6.1–6.35 (4H) and 8.3–8.6 ppm (6H).

IR spectrum (in paraffin oil) (carbonyl region): 1,770, 1,730, 1,665, 1,610 and 1,540 cm⁻¹.

NMR signals at τ (in CD₃OD)=2.2–3.3 (10H); 4.3–4.65 (3H); 5.7 (1H); 6.15–6.4 (4H) and 8.35–8.6 ppm (6H).

IR spectrum (in paraffin oil) (carbonyl region): 1,780, 1,740 (shoulder), 1,725, 1,645 and 1,520 cm⁻¹.

Sodium 6-{D-α-[(2-oxo-3-benzalamino-imidazolidin-1-yl)-carbonylamino]-4-hydroxyphenylacetamido}-penicillanate Yield: 1.4 pts. by wt.

β-lactam content (determined iodometrically): 96% (from the NMR spectrum): 87%

According to the NMR spectrum, the substance contains 2.5 mols of H₂O and 0.25 mol of sodium 2-ethylhexanoate per mol of substance (in addition to an unknown impurity, originating from the Amoxil used, and present in unknown amount). If the identified admixtures are taken into account in the calculated analytical data, the following is found:

calculated: C 50.6; H 5.2; N 12.2; S 4.6; found: C 51.2; H 6.0; N 11.7; S 4.5.

NMR signals at τ (in CD₃OD)=2.1–3.3 (10H);

Part 1.4.

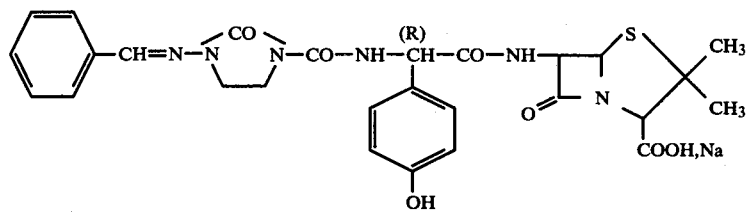

This penicillin is prepared in the manner described under 1.3. from amoxicillin trihydrate (6.0 pts. by wt.) and 1-chlorocarbonyl-2-oxo-3-benzalimino-imidazolidine (3.6 pts. by wt.) (see 1.2.). On acidifying the aqueous reaction solution with dilute hydrochloric acid (about 20% by weight) to pH 1.5, a part of the penicillin-acid liberated is not taken up by the ethyl acetate. This part is filtered off, washed with water and dried (yield: 5.2 pts. by wt.). Thereafter, some sodium salt of the penicillin can still be precipitated from the ethyl acetate phase by means of sodium 2-ethyl-hexanoate (yield: 1.4 pts. by wt.).

6-{D-α-[(2-Oxo-3-benzalimino-imidazolidin-1-yl)-carbonylamino]-4-hydroxyphenylacetamino}-penicillanic acid Yield: 5.2 pts. by wt.

β-Lactam content (determined iodometrically): 81% (from the NMR spectrum): 89%

According to the NMR spectrum the substance contains 3.4 mols of H₂O and 0.5 mol of ether per mol of substance. If this is taken into account in the calculated analytical data, the following is found:

calculated: C 51.2; H 5.9; N 12.4; S 4.7; found: C 50.7; H 5.5; N 12.8; S 4.8.

4.4–4.7 (3H); 5.8 (1H); 6.1–6.4 (4H) and 8.3–8.6 ppm (6H).

IR spectrum (in paraffin oil) (carbonyl region): 1,770, 1,735, 1,670, 1,600 and 1,560–1,520 cm⁻¹.

Part 1.5.

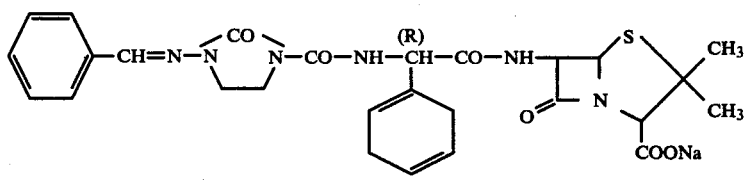

This penicillin is prepared in the manner described under 1.3. from epicillin (1.5 pts. by wt.) and 1-chlorocarbonyl-2-oxo-3-benzalimino-imidazolidine (1.1 pts. by wt.).

Yield: 1.7 pts. by wt., of sodium 6-{D-α-[(2-oxo-3-benzalimino-imidazolidin-1-yl)-carbonylamino]-cyclohex-1,4-dienyl(1)-acetamido}-penicillanate having a β-lactam content (determined iodometrically) of 90%. (Content calculated from the NMR spectrum: 91%).

According to the NMR spectrum, the substance contains 2.5 mols of H₂O and 0.072 mol of sodium 2-ethylhexanoate.

This was taken into account in the following analytical data:

calculated: C 51.2; H 5.4; N 13.0; S 4.9; found: C 50.9; H 5.7; N 13.6; S 4.6.

NMR signals at τ (in CD₃OD)=2.0–2.65(5H); 4.0(1H); 4.25(2H); 4.45(2H); 4.95(1H); 5.75(1H); 6.0–6.3(4H); 7.1–7.4(4H) and 8.25–8.5 ppm (6H).

IR spectrum (in paraffin oil) (carbonyl region): 1,765, 1,730, 1,660, 1,600 and 1,530 cm⁻¹. 13. 110:1

Part 1.6.

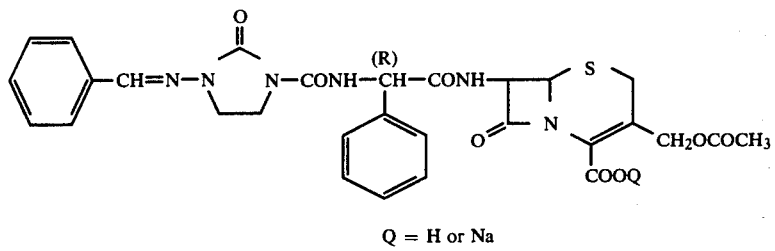

Q = H or Na 2.25 pts. by wt. of cephaloglycine dihydrate are suspended in 50 ml of 80 percent strength aqueous THF and reacted with 12.6 pts. by wt. of 1-chlorocarbonyl-2-oxo-3-benzalimino-imidazolidine, and worked up, as in Example 13. On acidifying with dilute hydrochloric acid (for example 2 N HCl), 7-{D-α-[(2-oxo-3-benzalimino-imidazolidin-11-yl)-carbonylamino]-phenylacetamido}-3-acetoxymethyl-ceph-3-em-4-carboxylic acid precipitates (1.9 pts. by wt., corresponding to 61.4%). This material is dissolved in 5 pts. by vol. of dimethylacetamide, 3 pts. by vol. of a methanolic 1 M sodium 2-ethylhexanoate solution are added and the mixture is added, while stirring, to 30 pts. by vol. of a 10 : 1 mixture of ether and methanol, whereupon 1.7 pts. by wt. of sodium 7-{D-α-[(2-oxo-3-benzalimino-imidazolidin-1-yl)-carbonylamino]-phenylacetamido}-3-acetoxymethyl-ceph-3-em-4-carboxylate of dec. pt. 180°-185° C. precipitate.

The ethyl acetate phase is worked up as in Example 1.3, whereby further 0.9 pt. by vol. (corresponding to 28.0%) of the sodium salt are obtained.

$C_{29}H_{27}N_6NaO_8S \cdot H_2O$: calculated: C 52.72; H 4.42; N 12.71; S 4.85; found: 52.5; 4.9; 12.2; 4.6.

IR (KBr): 1,760, 1,725, 1,670, 1,605 and 1,520 cm$^{-1}$.
NMR(CD$_3$OD/D$_2$O): 7.75 and 7.40 (m,11H), 5.75 (d,1H), 5.57 (s,1H), 5.00 (d,1H), 4.87 (on which is superposed the signal of the exchangeable protons), 3.82 (m,4H) and 2.08 (s,3H) δ.

The CD$_3$OD solvent peak is superposed on the signals of the C-2-protons.

The β-lactam content is between 80 and 85%.

EXAMPLE 2

Part 2.1.

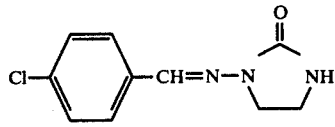

15.8 pts. by wt. of 2-oxo-imidazolidine, 12.6 pts. by wt. of sodium nitrite and 27.5 pts. by wt. of zinc dust are processed as in Example 1.1. and stirred with 23.2 pts. by wt. of 4-chlorobenzaldehyde overnight.

20.5 pts. by wt. of 1-(4-chloro)-benzalimino-2-oxoimidazolidine of melting point 233°-235° C.

$C_{10}H_{10}ClN_3O$ calculated: C 53.70; H 4.51; N 18.79; Cl 15.85; found: 53.9; 4.5; 18.7; 16.0.

IR (KBr): 3,250, 3,130, 1,735, 1,705 and 1,595 cm$^{-1}$.
NMR(d$_6$-DMSO): 7.66 and 7.45 (AB,4H), 7.60 (s,1H), 7.15 (s,broad,1H), m, centred at 3.6 (4H)δ.

Part 2.2.

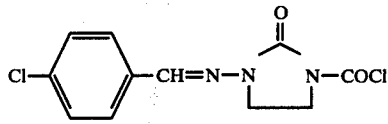

A solution of 31.0 pts. by wt. of trimethylchlorosilane in 100 pts. by vol. of absolute dioxane is added dropwise over the course of 1 hr., while stirring, to a boiling solution of 21.4 pts. by wt. of 1-(4-chloro)-benzalimino-2-oxo-imidazolidine and 31.0 pts. by wt. of triethylamine in 240 pts. by vol. of absolute dioxane. The mixture is then heated overnight under reflux, the triethylammonium hydrochloride which has separated out is filtered off hot and washed with hot dioxane, and after cooling a solution of 9.9 pts. by wt. of phosgene in 60 pts. by vol. of abs. dioxane is added. After standing for 12 hrs. at room temperature, excess phosgene is flushed out by means of dry air. The precipitate is filtered off, the filtrate is concentrated and the residue is recrystallised from abs. acetonitrile. 8.9 pts. by wt. of 1-chlorocarbonyl-2-oxo-3-(4-chloro)-benzalimino-imidazolidine of dec. pt. 188°-192° C.

IR (paraffin oil): 1,800 and 1,700 cm$^{-1}$.

Part 2.3.

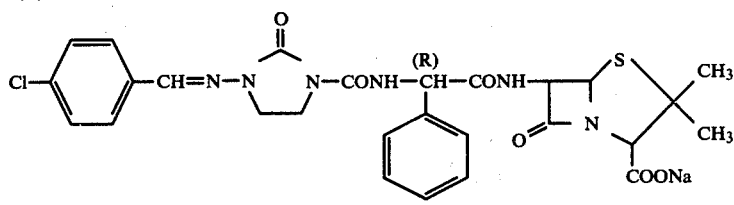

7.9 pts. by wt. of ampicillin trihydrate in 80 pts. by vol. of 80% strength by volume aqueous THF are reacted with 2.8 pts. by wt. of 1-chlorocarbonyl-2-oxo-3-(4-chloro)-benzalimino-imidazolidine as in Example 1.3. 1.4 pts. by wt. of sodium 6-{D-α-[(2-oxo-3-{4-chloro}-benzalimino-imidazolidin-1-yl)-carbonylamino]-phenylacetamido}-penicillanate of dec. pt. 210°-5° C., and having a β-lactam content of 87%, are obtained.

IR(KBr): 1,760, 1,725, 1,665 and 1,595 cm$^{-1}$.
NMR (CD$_3$OD): 7.6–7.2 (m,10H), 5.60 (s,1H), 5.45 (q,2H), 4.15 (s,1H), 3.80 (broad s,4H), 1.57 (s,3H), and 1.48 (s,3H)δ.

Part 2.4.

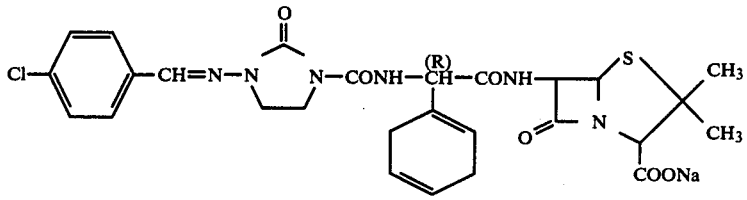

2.0 pts. by wt. of sodium epicillin in 40 pts. by vol. of 80% strength by volume THF are reacted with 3.5 pts. by wt. of 1-chlorocarbonyl-2-oxo-3(4-chloro)-benzaliminoimidazolidine as in Example 1.5. 0.4 pt. by wt. of sodium 6-{D-α-[(2-oxo-3-{4-chloro}-benzalimino-imidazolidin-1-yl)carbonylamino]-cyclohex-1,4-dienyl(1)-acetamido}-penicillanate of 92% β-lactam content is obtained.

IR(KBr): 1,700, 1,730, 1,670 and 1,605 cm$^{-1}$.

NMR(CD$_3$OD): 7.78 (s,1H), 7.76 and 7.36 (AB,4H), 5.95 (m,1H), 5.72 (s,2H), 5.50 (s,2H), 5.00 (s,1H), 4.20 (s,1H), 3.95 (s,broad,4H), 2.75 (s,broad,4H), 1.65 (s,3H) and 1.58 (s,3H)δ.

Part 2.5.

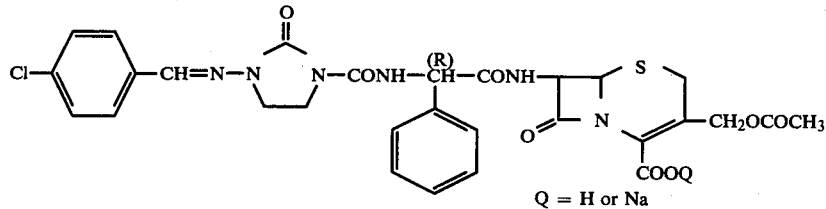
Q = H or Na 2.25 pts. by wt. of cephaloglycine dihydrate in 40 pts. by vol. of 80% strength by volume THF are reacted with 3.5 pts. by wt. of 1-chlorocarbonyl-2-oxo-3(4-chloro)-benzalimino-imidazolidine as in Example 1.6. 0.6 pt. by wt. of sodium 7-{D-α[(2-oxo-3-{4-chloro}-benzalimino-imidazolidin-1-yl)-carbonylamino]-phenylacetamido}-3-acetoxymethyl-ceph-3-em-4-carboxylate of β-lactam content 80–85% is obtained.

IR(KBr): 1,760, 1,720, 1,660 and 1,595 cm$^{-1}$.

NMR(CD$_3$OD): 7.7 and 7.4 (m,10H), 5.65 (d,1H), 5.60 (s,1H), 5.0–4.8 m (on which is superposed the signal of the exchangeable protons) 3.88 and 3.70 (superposed multiplets), 2.03 (s,3H) δ.

C$_{29}$H$_{26}$ClN$_6$NaO$_8$S.1½ H$_2$O.¼ dimethylacetamide: calculated: C 50.25; H 4.22; N 11.72; S 4.48; found: 50.1; 4.5; 11.1; 5.4.

Part 2.6.

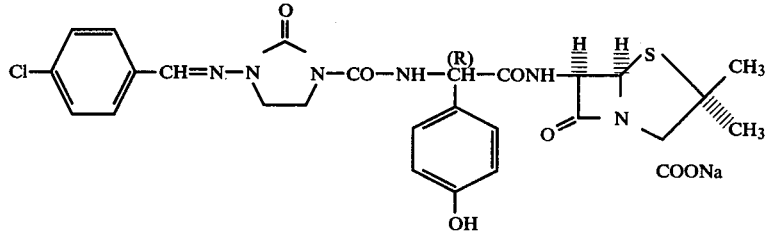

6.3 pts. by wt. of amoxicillin trihydrate in 80 pts. by vol. of 80 percent strength aqueous THF are reacted with 2.9 pts. by wt. of 1-chlorocarbonyl-2-oxo-3-(4-chloro)-benzalimino-imidazolidine as in Example 1.4. 4.6 pts. by wt. of sodium 6-{D-α-[(2-oxo-3-{4-chloro}-benzaliminoimidazolidin-1-yl)-carbonylamino]-4-hydroxyphenyl-acetamido}-penicillanate of dec. pt. 220°–4° C. are obtained.

IR (KBr): 1,775, 1,730, 1,670 and 1,615 cm$^{-1}$.

NMR (CD$_3$OD): 6.7–8.0 (9 H), 5.4–5.6 (3 H), 4.95 (3 exchangeable H), 4.15 (1 H), 3.80 (4 H), 1.58 (3 H), 1.52 (3 H)δ.

C$_{27}$H$_{26}$ClN$_6$NaO$_7$S.2H$_2$O: calculated: C 48.18; H 4.49; N 12.49; S 4.77; found: C 48.7; H 5.1; N 12.6; S 4.5.

EXAMPLE 3

Part 3.1.

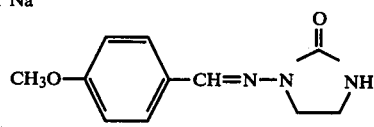

15.8 pts. by wt. of 2-oxo-imidazolidine, 12.6 pts. by wt. of sodium nitrite and 27.5 pts. by wt. of zinc dust are processed as in Example 2.1. and reacted with 22.4 pts. by wt. of 4-methoxybenzaldehyde. 15.8 pts. by wt. of 1-(4-methoxy)-benzalimino-2-oxo-imidazolidine of melting point 179°–181° C. are obtained.

IR(KBr): 3,250, 3,130, 1,725, 1,700 and 1,605 cm$^{-1}$.

NMR(d$_6$-DMSO): 7.56 and 6.92 (AB,4H), 7.52 (s,1H), 7.04 (s,1H), 3.72 (s,3H), m centred at 3.52 (4H)δ.

C$_{11}$H$_{13}$N$_3$O$_2$: Calculated: C 60.27; H 5.97; N 19.17; found: 60.3; 5.9; 18.9.

Part 3.2.

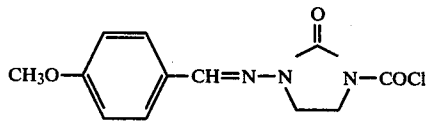

A solution of 20.0 pts. by wt. of trimethylchlorosilane in 50 pts. by vol. of abs. benzene is added dropwise to a boiling solution of 13.6 pts. by wt. of 1-(4-methoxy)-benzalimino-2-oxo-imidazolidine and 27.6 pts. by vol. of triethylamine in 120 pts. by vol. of abs. benzene, and the mixture is reacted and worked up as in Example 1.2. 6.2 pts. by wt. of 1-chlorocarbonyl-2-oxo-3(4-methoxy)-benzalimino-imidazolidine of melting point 204°–208° C. are obtained.

IR (paraffin oil): 1,800 cm$^{-1}$.

2.25 pts. by wt. of cephaloglycine dihydrate suspended in 40 pts. by vol. of 80% strength by volume THF, and worked up, as in Example 1.6.

On acidification, 7-{D-α-[(2-oxo-3-{4-methoxy}-benzalimino-imidazolidin-1-yl)-carbonylamino]-phenylacetamido}-3-acetoxymethyl-ceph-3-em-4-carboxylic acid precipitates (1.2 pts. by wt.) and is reacted, as in Example 1.4., with 1.9 pts. by vol. of a 1 M sodium 2-ethyl-hexanoate solution to give sodium 7-{D-α-[(2-oxo-3-{4-methoxy}-benzalimino-imidazolidin-1-yl)-car- Part 3.3.

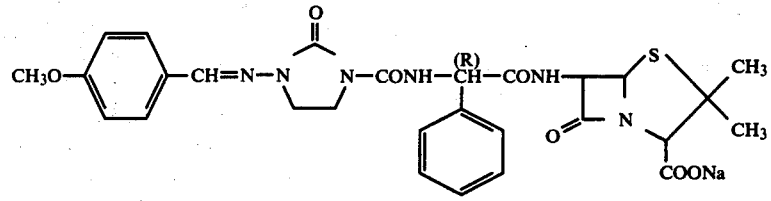

6.9 pts. by wt. of ampicillin trihydrate in 70 pts. by vol. of 80% strength by volume THF and 2.4 pts. by wt. of 1-chlorocarbonyl-2-oxo-3-(4-methoxy)-benzalimino-imidazolidine are reacted as in Example 1.3. 4.5 pts. by wt. of sodium 6-{D-α-[(2-oxo-3-{4-methoxy}-benzalimino-imidazolidin-1-yl)carbonylamino]-phenylacetamido}-penicillanate of dec. pt. 213°–223° C. and of 87% β-lactam content are obtained.

IR(KBr): 1,770, 1,730, 1,675 and 1,605 cm$^{-1}$.

NMR(CD$_3$OD): 7.60 and 6.85 (AB,4H), 7.4 (m,5+1H), 5.60 (s,1H), 5.45 (q,2H), 4.15 (s,1H), 3.72 (s,3H), 3.63 (broad s,4H), 1.55 (s,3H), 1.50 (s,3H)δ.

bonylamino]-phenylacetamido}-3-acetoxymethyl-ceph-3-em-4-carboxylate (0.7 pts. by wt.).

The ethyl acetate phase is worked up as in Example 1.3, whereby a further 1.6 pts. by wt. of the sodium salt of dec. pt. 220°–230° and of 80% β-lactam content are obtained.

IR(KBr): 1,770, 1,730, 1,660 and 1,610 cm$^{-1}$.

NMR(CD$_3$OD/D$_2$O): 7.55 and 6.85 (AB,4H), 7.40 (s, superposed on the AB system, 1H), 5.67 (d,1H), 5.47 (s,1H), 5.15–4.85 (m, on which is superposed the signal of the exchangeable protons), 3.76 (broad s,4H), 2.05 (s,3H)δ.

Part 3.4.

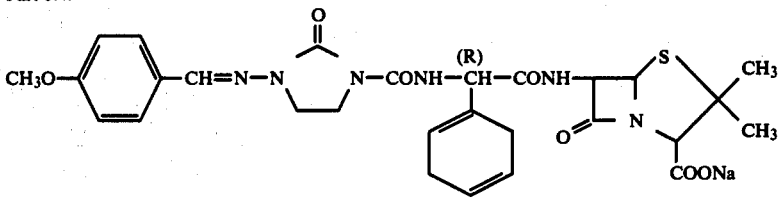

2.0 pts. by wt. of sodium-epicillin in 40 pts. by vol. of 80% strength by volume THF are reacted with 2.1 pts. by wt. of 1-chlorocarbonyl-2-oxo-3(4-methoxy)-benzalimino-imidazolidine as in Example 1.5. 3.5 pts. by wt. of sodium 6-{D-α-[(2-oxo-3-{4-methoxy}-benzalimino-imidazolidin-1-yl)-carbonylamino]-cyclohex-1,4-dienyl(1)-acetamido}-penicillanate of 68% β-lactam content are obtained.

IR(KBr): 1,760, 1,720, 1,655 and 1,600 cm$^{-1}$.

NMR(CD$_3$OD): 7.60 and 6.85 (AB,4H), 7.40 (s, superposed on the AB system, 1H), 5.90 (broad s,1H), 5.67 (s,2H), 5.50 (s,2H), 5.00 (s,1H), 4.20 (s,1H), 3.77 (broad s,4H), 2.72 (broad s,4H), 1.65 (s,3H), 1.57 (s,3H)δ.

$C_{30}H_{29}N_6NaO_9S.H_2O$ 690.6; calculated: C 52.18; H 4.52; N 12.17; S 4.65; found: 51.9; 4.4; 11.8; 5.1.

EXAMPLE 4

Part 4.1.

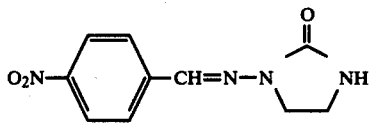

15.8 pts. by wt. of 2-oxo-imidazolidine, 12.6 pts. by wt. of sodium nitrite and 27.5 pts. by wt. of zinc dust, as Part 3.5.

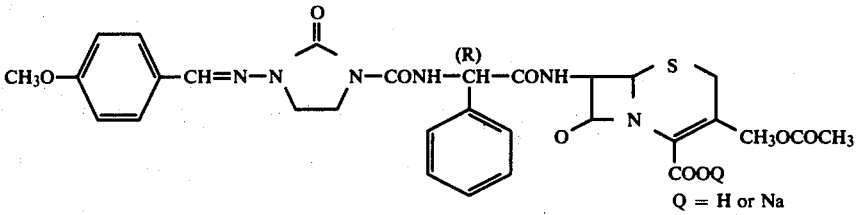

Q = H or Na 1.41 pts. by wt. of 1-chlorocarbonyl-2-oxo-3-(4-methoxy)-benzalimino-imidazolidine are reacted with well as 24.9 pts. by wt. of 4-nitrobenzaldehyde are reacted as in Example 2.1. The resulting 1-(4-nitro)-benzalimino-2-oxo-imidazolidine is freed from impurities by boiling with ethanol; 37.6 pts. by wt. of melting point 265°–267° C.

IR(KBr): 3,430, 3,260, 1,720, 1,595 and 1,570 cm$^{-1}$.
NMR(D$_6$-DMSO): 8.20 and 7.88 (AB,4H), 7.68 (s,1H), 7.37 (broad s,1h), m, centred at 3.65 (4H)δ.

calculated: C 51.28; H 4.31; N 23.92; found: 51.2; 4.3; 223.9.

Part 4.2.

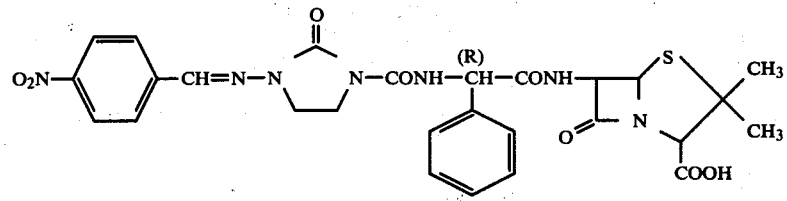

8.8 pts. by wt. of 1-(4-nitro)-benzalimino-2-oxo-imidazolidine, 12.1 pts. by wt. of triethylamine, 12.0 pts. by wt. of trimethylchlorosilane and 3.9 pts. by wt. of phosgene are reacted as in Example 2.2. The 1-chlorocarbonyl2-oxo-3-(4-nitro)-benzalimino-imidazolidine is recrystallized fro abs. acetonitrile; 2.6 pts. by wt. of dec. pt. 188°–192° C. result.

IR (paraffin oil): 1,800, 1,760 and 1,700 cm$^{-1}$.

Part 4.3.

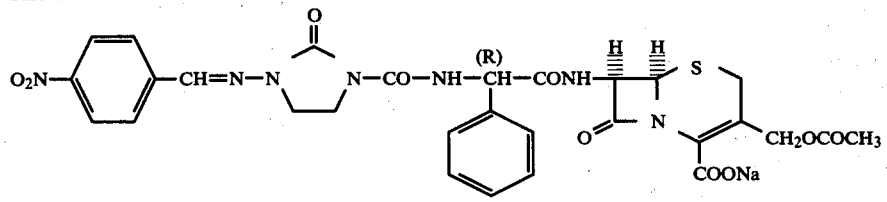

6.8 pts. by wt. of ampicillin trihydrate in 70 pts. by vol. of 80% strength by volume aqueous THF are reacted wtih 2.5 pts. by wt. of 1-chlorocarbonyl-2-oxo-3-(4-nitro)-benzalimino-imidazolidine as in Example 1.3. 3.0 pts. by wt. of sodium 6-{D-α-[(2-oxo-3-{4-nitro}-benzalimino-imidazolidin-1-yl)-carbonylamino]-phenylacetamido}-penicillanate of dec. pt. 220°–5° C. and of 98% β-lactam content are obtained.

IR(KBr): 1,765, 1,730, 1,670 and 1,600 cm$^{-1}$.
NMR(CD$_3$OD): 8.30 and 7.96 (AB-system, 4H), 7.81 (s,1H), m centred at 7.45 (5H), 5.64 (s,1H), 5.57 (q,2H), 4.20 (s,1H), 3.88 (broad s, 4H), 1.58 (s,3H), 1.50 (s,3H)δ.

C$_{27}$H$_{26}$N$_7$NaO$_8$S. 2.5 H$_2$O: calculated: C 47.93; H 4.62; N 14.50; S 4.74; found: 47.7; 4.3; 14.4; 4.8.

Part 4.4.

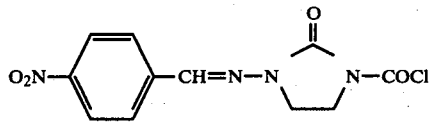

6.5 pts. by wt. of cephaloglycine dihydrate in 80 pts. by vol. of 80 percent strength aqueous THF are reacted with 4.4 pts. by wt. of 1-chlorocarbonyl-2-oxo-3-(4-nitro)-benzalimino-imidazolidine as in Example 3.5. 9.3 pts. by wt. of sodium 7-{D-α-[(2-oxo-3-{4-nitro}-benzalimino-imidazolidin-1-yl)-carbonylamino]-phenylacetamido}-3-acetoxymethyl-ceph-3-em-4-carboxylate of dec. pt. 220°–5° C. are obtained.

IR (KBr): 1,760, 1,730, 1,660 and 1,605 cm$^{-1}$.
C$_{29}$H$_{26}$N$_7$NaO$_{10}$.2H$_2$O: calculated: C 48.13; H 4.19; N 13.56; S 4.42; found: C 48.0; H 4.1; N 13.4; S 4.4.

EXAMPLE 5

Part 5.1.

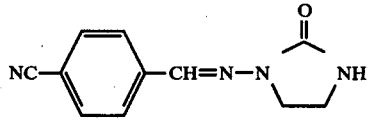

12.6 pts. by wt. of 2-oxo-imidazolidine, 10.1 pts. by wt. of sodium nitrite and 21.8 pts. by wt. of zinc dust are processed as in Example 2.1. and reacted with 17.3 pts. by wt. of 4-cyanobenzaldehyde. 26.2 pts. by wt. of 1-(4-cyano)-benzalimino-2-oxo-imidazolidinee are obtained and are freed from impurities by successive washing with water, ethanol and ether. Melting point 265°–267° C.

IR(KBr): 3,210, 3,120, 2,220, 1,720 and 1,590 cm$^{-1}$.
NMR(d$_6$-DMSO): 7.88 (s,4H), 7.66 (s,1H), 7.30 (broad s, 1H), m centred at 3.7 (4H)δ.

calculated: C 61.68; H 4.71; N 26,15; found: 59,8; 4.6; 25.9.

Part 5.2.

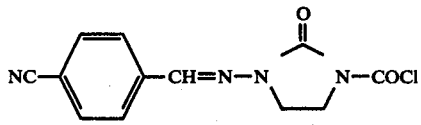

7.5 pts. by wt. of 1-(4-cyano)-benzalimino-2-oxoimidazolidine and 12.1 pts. by wt. of triethylamine in 60 pts. by vol. of abs. dioxane, 12.0 pts. by wt. of trimethylchlorosilane in 25 pts. by vol. of abs. dioxane and 3.9 pts. by wt. of phosgene are reacted as in Example 2.2. The 1-chlorocarbonyl-2-oxo-3-(4-benzalimino-imidazolidine is recrystallised from abs. acetonitrile; 4.7 pts. by wt. of melting point 260°–264° C. are obtained.

IR (prarffin oil): 1,800 cm$^{-1}$.
calculated: C 52.09; H 3.28; N 20.25; Cl 12.82; found: 52.0; 3.3; 20.3; 12.5.

Part 5.3.

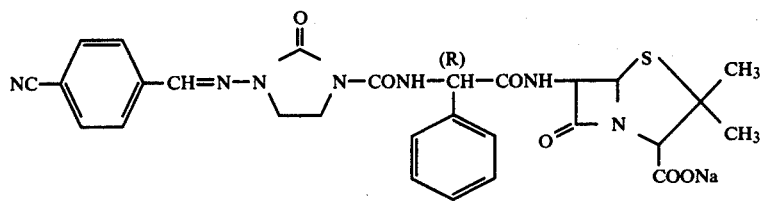

7.9 pts. by wt. of ampicillin trihydrate in 80 pts. by vol. of 80% strength by volume aqueous THF are reacted with 2.7 pts. by wt. of 1-chlorocarbonyl-2-oxo-3-(4-cyano)benzalimino-imidazolidine as in Example 1.3 2.3 pts. by wt. of sodium 6{D-α-[(2-oxo-3-{4-cyano}-benzalimino-imidazolidin-1-yl)-carbonylamino]-phenylacetamido}-penicillanate of dec. pt. 225°–230 C. and of 88% β-lactam content are obtained.

IR(KBr): 2,220, 1,770, 1,730, 1,665 and 1,600 cm$^{-1}$.
NMR(CD$_3$OD):7.95–7.20 (10H), 5.56 (s,1H), 5:42 (q,2H), 4.12 (s,1H), 3.87 (broad s, 4H), 1.57 (s,3H), 1.48 (s,3H)δ

$C_{28}H_{26}N_7NaO_6S$.2.5 H$_2$O: calculated: C 51.21; H 4.76; N 14,93; found: 51.6; 4.9; 14.4.

EXAMPLE 6

Part 6.1.

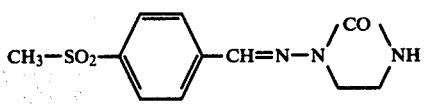

This substance is prepared in the manner described in Example 1.1. except that the reaction is carried out in a 1:1 (by volume) mixture of water and dichloromethane, from 15.8 pts. by wt. of imidazolidone and 31.0 pts. by wt. of 4-methylsulphonylbenzaldehyde. The crude product is recrystallised from nitromethane.

Yield: 9.2 pts. by wt. of 1-(4-methylsulphonyl)-benzalimino-2-oxo-imidazolidine, melting point = 264° C.

NMR signals at τ=2.0 (4H), 2.2 (1H), 5.9–6.65 (4H) and 6.7 ppm (3H).

calculated: C 49.4; H 4.9; N 15.7; O 18.0; S 12.0; found: 48.6; 5.0; 15.7; 18.3; 12.1.

Part 6.2.

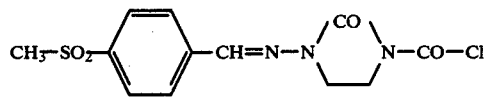

This substance is prepared in the manner described in Example 1.2. from 9.2 pts. by wt. of 1-(4-methylsulphonyl)-benzalimino-2-oxo-imidazolidine. The crude product is recrystallised from nitromethane and acetonitrole. Yield 5.4 pts. by wt. of 1-chlorocarbonyl-2-oxo-3-(4-methylsulphonyl)-benzalimino-imidazolidine.

Melting point=208°–213° C.

calculated: C 43.7; H 3.6; Cl 10.8 N 12.8; S 9.7; found: 43.8; 4.9; 10.2; 12.5; 9.5.

Part 6.3.

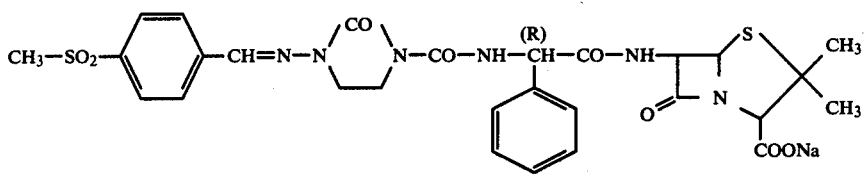

This penicillin is prepared in the manner described in Example 1.3. from ampicillin trihydrate (2.0 pts. by wt.) and 1-chlorocarbonyl-2-oxo-3-(4-methylsulphonyl)benzaliminoimidazolidine (1.6 pts. by wt.). The penicillin-acid separates out as a crystalline precipitate which is insoluble in water and ethyl acetate (1.6 pts. by wt.). This penicillin-acid is dissolved in a little dimethylformamide, the calculated quantity of sodium 2-ethylhexanoate solution (in ether containing methanol) is added and the sodium salt of the penicillin is precipitated by pouring the mixture into a large amount of ether.

Yield: 0.85 pts. by wt. of sodium D-α-{[2-oxo-3-(4-methyl-sulphonyl)-benzalimino-imidazolidin-1yl]-carbonylamino}-benzylpenicillin.

β-Lactam content: 90%.

According to the NMR spectrum, the penicillin contains about 1.5 mols of water, 0.2 mol of ethyl acetate, 0.25 mol of dimethylformamide and 0.15 mol of sodium 2-ethylhexanoate. this was taken into account in the calculated analytical data:

calculated: C 49.1; H 5.1; N 11.6; S 8.5; found: 48.5; 4.8; 11.8; 8.4;

NMR signals at τ=2.05 (4H), 2.2 (1H), 2.2–2.8 (5H), 4.3–4.65 (3H), 5.8 (1H), 5.9–6.4 (4H), 6.85 (3H) and 8.2–8.7 ppm (6H).

Part 6.4.

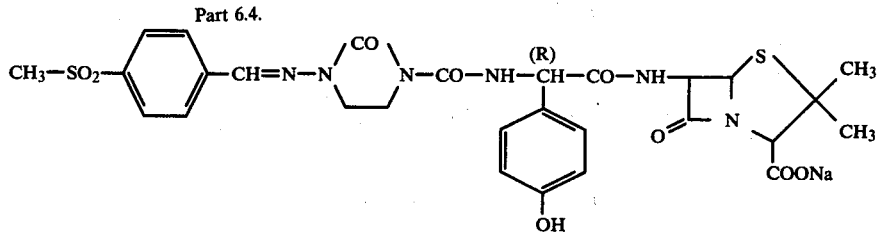

This penicillin is obtained in the manner described in Example 1.3. and 6.3 from amoxicillin (1.5 pts. by wt.) and 1-chlorocarbonyl-2-oxo-3-(4-methylsulphonyl)benzaliminoimidazolidine (1.18 pts. by wt.), initially as crystalline penicillin-acid (1.8 pts. by wt.) and then as the sodium salt. Yield: 2.0 pts. by wt. of sodium D-α-{[2-oxo-3-(4-methylsulphonyl)benzalimino-imidazolidin-1-yl)]-p-hydroxybenzylpenicillin. -p-hydroxybenzylenicillin.

β-Lactam content: 85%.

According to the NMR spectrum, this penicillin contains about 2.0 mols of water, 0.25 mol of ethyl acetate, 0.7 mol of dimethylformamide and 0.08 mol of sodium 2-ethylhexanoate. This was taken into account in the calculated analytical data.

calculated: C 47.4; H 5.1; N 11.7; S 8.0 found: 47.2; 5.0; 11.1; 7.9.

NMR signals at τ=2.1 (4H), 2.2 (1H), 2.5–3.3 (4H), 4.35–4.65 (3H), 5.8 (1H), 5.9–6.4 (4H), 6.85 (3H) and 8.2–8.7 ppm (6H).

Part 6.5.

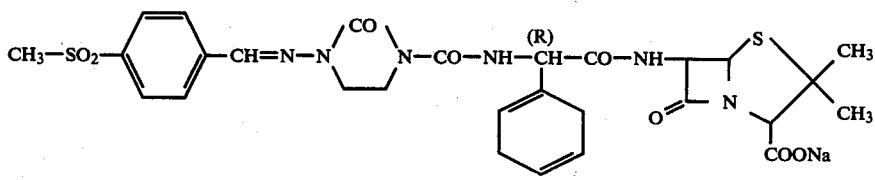

This penicillin is obtained in the manner described in Example 1.3. and 6.3. from epicillin (1.0 pts. by wt.) and 1-chlorocarbonyl-2-oxo-3-(4-methylsulphonyl)benzaliminoimidazolidine (0.94 pts. by wt.), initially as crystalline penicillin-acid (1.8 pts. by wt.) and then as the sodium salt.

Yield: 1.6 pts. by wt.

Sodium D-α-{[2-oxo-3-(4-methylsulphonyl)benzaliminoimidazolidin-1-yl]-carbonylamino}-α-(1,4-cyclohexadien-1-yl)-methylpenicillin.

β-Lactam content: 81%.

According to the NMR spectrum, this penicillin contains about 3.0 mols of water, 0.3 mol of ethyl acetate, 0.4 mol of dimethylformamide and 0.12 mol of sodium 2-ethylhexanoate. This was taken into account in the calculated analytical data:

calculated: C 47.3; H 5.5; N 11.3; S 8.1; found: 46.9; 5.5; 11.3; 8.1. NMR signals at τ=2.0(4H), 2.15 (1H), 4.0 (1H), 4.25 (2H), 4.45 (2H, 5.0 (1H), 5.8 (1H), 5.8-6.3 (4H), 6.8 (3H), 7.0-7.4 (4H) and 8.2–8.7 ppm (6H).

Part 6.6.

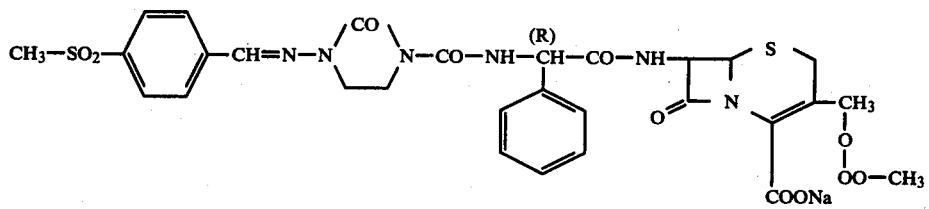

This cephalosporin is obtained in the manner described in Example 1.3. and 6.3 from cephaloglycine (1.5 pts. by wt.) and 1-chlorocarbonyl-2-oxo-3-(4-methylsulphonyl)-benzalimino-imidazolidine 1.0 pts. by wt.), in part initially as the crystalline acid (the portion which is insoluble in ethyl acetate and water) (1.0 pts. by wt.) and in part immediately as the sodium salt (the portion dissolved in ethyl acetate, from which is is precipitated as the sodium salt) (0.75 pts. by wt.). Further sodium salt is then prepared from the penicillin-acid as described in Example 6.3. Total yield: 1.85 pts. by wt. of sodium 7-D-α-/{[2-oxo-3-(4-methylsulphonyl)-benzalimino-imidazolidin-1-yl]-carbonylamino}-phenylacetamido/-3-acetoxymethyl-ceph-3-em-4-carboxylate.

β-Lactam content: 84%.

According to the NMR spectrum, this cephalosporin contains about 1.7 mols of water, 0.4 mol of dimethylformamide, 0.4 mol of ethyl acetate and 0.16 mol of sodium 2-ethylhexanoate. This was taken into account in the calculated analytical data:

calculated: C 47.4; H 4.6; N 10.5; S 7.5; found: 47.3; 4.2; 10.8; 8.1.

NMR signals at τ = 2.1 (4H), 2.25 (1H), 2.5–2.9 (5H), 4.3–4.6 (2H), 5.05–5.3 (3H), 6.0–6.3 (4H), 6.7 (2H), 6.9 (3H) and 8.0 ppm (3H).

EXAMPLE 7

Part 7.1.

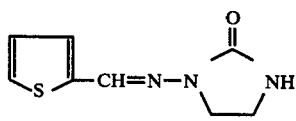

15.8 pts. by wt. of 2-oxo-imidazolidine, 12.6 pts. by wt. of sodium nitrite and 27.5 pts. by wt. of zinc dust, and 18.5 pts. by wt. of thiophen-2-aldehyde are reacted as in Example 1.1. The resulting 1-(thiophen-2-aldimino)-2-oxo-imidazolidine is freed from impurities by boiling with ethanol, or is recrystallised from dimethylformamide. 22.4 pts. by wt. of melting point 263°–265° C. IR(KBr);3,240 and 1,705 (broad) cm⁻¹.

NMR(d₆-DMSO): 7.88 (s,1H), 7.3-7.0 (heteroaromatic protons, as well as NH,4H), m, centred at 3.6 (4H).

calculated: C 49.22; H 4.65; N 21.52; S 16.42; found: 49.4; 4.6; 21.4; 16.1.

Part 7.2.

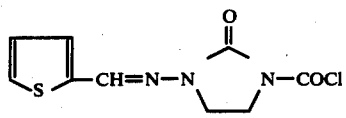

9.8 pts. by wt. of 1-thiophen-2-aldimino)-2-oxoimidazolidine, 16.2 pts. by wt. of triethylamine, 16.1 pts. by wt. of trimethylchlorosilane and 5.1 pts. by wt. of phosgene are reacted as in Example 1.2. 7.7 pts. by wt. of 1-chlorocarbonyl-2-oxo-3-(thiophen-2-aldimino)-imidazolidine of dec. pt. 184°–188° C. are obtained.

IR (paraffin oil): 1,830 and 1,720 cm⁻¹.

The chlorocarbonyl compound still contais starting material which was not removed, since it does not interfere with the subsequent reactions.

Part 7.3.

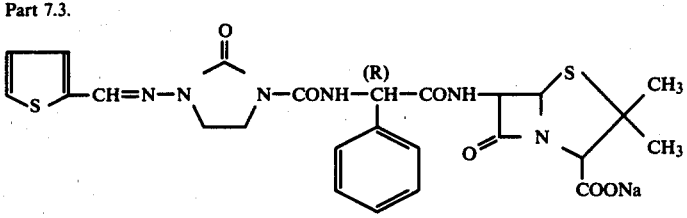

2.6 pts. by wt. of 1-chlorocarbonyl-2-oxo-3-(thiophen-2-aldimino)-imidazolidine and 4.1 pts. by wt. of ampicillin trihydrate in 40 pts. by vol. of 80% strength by volume aqueous THF are reacted as in Example 1.3. 0.4 pts. by wt. of sodium 6-{D-α-[(2-oxo-3-{thiophen-2-aldimino}-imidazolidin-1-yl)-carbonylamino]-phenylacetamido}-penicillanate of dec. pt. 210°–220° C. and of 89% β-lactam content are obtained.

IR(KBr): 1,760, 1,720, 1,660 and 1,600 cm¹.

NMR(CD₃OD): 7.90 (s,1H), 7.5–6.8 (aromatic and heteroaromatic protons, 8H), 5.51 (s, with superposed m around 5.4, of total 3H), 4.12 (s,1H), 3.79 (broad s, 4H), 1.57 (s,3H), 1.48 (s,3H)δ.

$C_{25}H_{25}N_6NaO_6S_2$·2.5 H₂O.0.25 ether; 656.1: calculated: C 47.60; H 5.00; N 12.81; S 9.79; found: 47.6; 5.5; 12.4; 10.0.

Part 7.4.

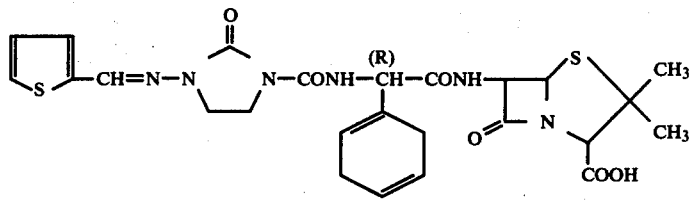

2.6 pts. by wt. of 1-chlorocarbonyl-2-oxo-3-(thiophen-2-aldimino)-imidazolidine and 2.0 pts. by wt. of sodium epicillin in 40 pts. by vol. of 80% strength by volume aqueous THF are reacted as in Example 1.5. 0.8 pts. by wt. of sodium 6-{D-α-[(2-oxo-3-{thiophen-2-aldimino}-imidazolidin-1-yl)-carbonylamino]-cyclohex-1,4-dienyl(1)-acetamido}-penicillanate of dec. pt. 205°–215° C., and of 89% β-lactam content, is obtained.

IR(KBr): 1,770, 1,730, 1,665 and 1,605 cm⁻¹.

NMR(CD₃OD): 8.00 (s,1H), 7.5–7.0 (hetero-aromatic protons, 3H), 5.95 (broad s, 1H), 5.70 (s,2H), 5.50 (s,2H), 5.00 (s,1H), 4.20 (s,1H), 3.86 (broad s, 4H), 2,73 (broad s, 4H), 1.64 (s, 3H), 1.57 (s,3H)δ.

$C_{25}H_{27}N_6NaO_6S_2$·2H₂O 530.6: calculated: C 47.61; H 4.95; N 13.32; S 10.16; found: 47.6; 5.1; 13.0; 10.2.

Part 7.5.

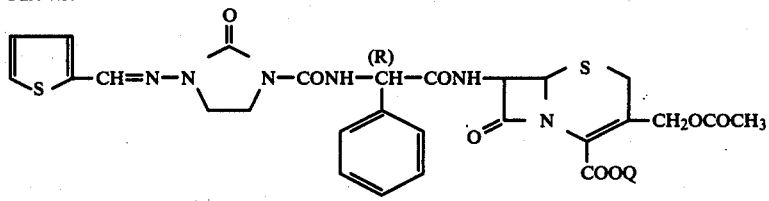

Q = H or Na 1.50 pts. by wt. of 1-chlorocarbonyl-2-oxo-3-(thiophen-2-aldimino)-imidazolidine and 2.25 pts. by wt. of cephaloglycine dihydrate in 40 pts. by vol. of 80% strength by volume THF are reacted as in Example 1.6. On acidification, 7-{D-α-[(2-oxo-3-{thiophen-2-aldimino}-imidazolidin-1-yl)-carbonylamino]-phenylacetamido}-3-acetoxymethyl-ceph-3-em-4-carboxylic acid (0.6 pts. by wt.) precipitates and this is reacted, as in Example 1.4. with 3 pts. by vol. of a 1 M sodium 2-ethyl-hexanoate solution to give sodium 7{D-α-[(2-oxo-3-{thiophen-2-aldimino}-imidazolidin-1-yl)- carbonylamino]-phenylacetamido}-acetoxymethyl-ceph-3-em-4-carboxylate.

The β-lactam content is 75–80%.

IR(KBR): 1,755, 1,720, 1,660 and 1,600 cm¹.

NMR(CD₃OD): 7.95 (s,1H), 7.5–6.8 (aromatic and heteroaromatic protons, 8H), 5.75–5.00 (m,3H), 4.8 (on which is superposed the signal of the exchangeable protons), 3.82 (broad s, 4H), 2.00 (s,3H)δ.

EXAMPLE 8

Part 8.1.

lin trihydrate in 200 pts. by vol. of 80% strength by volume aqueous THF are reacted as in Example 1.3. 2.3 pts.by wt. of sodium 6-{D-α-[(2-oxo-3-furylideneamino-imidazolidin-1-yl)-carbonylamino]-phenylacetamino]-phenylacetamido}-penicillanate of dec. pt. 200°–207° C., and of 81% β-lactam content, are obtained.

IR(KBr): 1,760, 1,715, 1,660 and 1,600 cm⁻¹.

NMR(CD₃OD): 7.60 (s,1H), 7.50–6.35 (aromatic and heteroaromatic protons, 8H), 5.55 (s,1H), 5.40 (q,2H), 4.12 (s,1H), m centred at 3.75 (4H), 1.55 (s,3H), 1.48 (s,3H)δ.

$C_{24}H_{25}N_6NaO_7S.1.5\ H_2O.0.25$ ether; calculated: C 49.22; H 5.04; N 13.76; S 5.26; found: 49.5; 4.8; 13.5; 5.2.

Part 8.4.

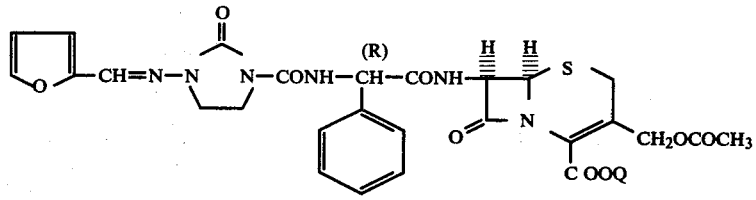

Q=H or Na

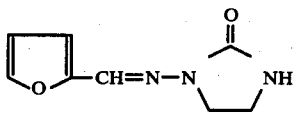

15.8 pts. by wt. of 2-oxo-imidazolidine, 12.6 pts. by wt. of sodium nitrite and 27.5 pts. by wt. of zinc dust, and 15.8 pts. by wt. of furan-2-aldehyde, are reacted as in Example 1.1. 17.5 pts. by wt. of 1-furylideneamino-2-oxo-imidazolidine of melting point 218°–220° C. are obtained.

IR(KBr): 3,200, 3,110, 1,715 and 1,585 cm⁻¹.

NMR(d₆-DMSO): 7.70 (m,1H), 7.50 (s,1H), 7.15 (broad s, 1H), 6.50–6.75 (m,2H), m centred at 3.55 (4H)δ.

calculated: C 53.63; H 5.06; N 23.45; found: 53.7; 5.0; 23.2.

Part 8.2.

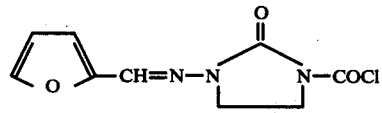

11.5 pts. by wt. of 1-furylideneamino-2-oxo-imidazolidine, 10.0 pts. by wt. of triethylamine, 13.2 pts. by wt. of trimethylchlorosilane and 6.2 pts. by wt. of phosgene are reacted as in Example 1.2. 3.8 pts. by wt. of 1-chlorocarbonyl-2-oxo-3-furylideneamino-imidazolidine of dec. pt. 188°–192° C. are obtained.

IR (paraffin oil): 1,800 and 1,700 cm⁻¹.

Part 8.3.

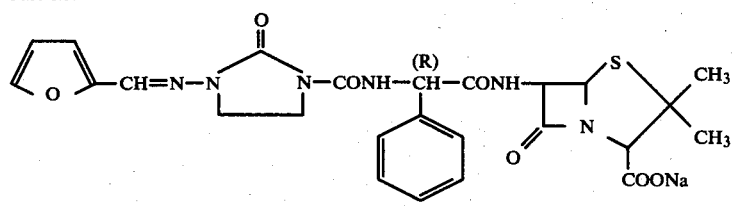

6.1 pts. by wt. of 1-chlorocarbonyl-2-oxo-3-(furan-2-aldimino)-imidazolidine and 20.4 pts. by wt. of ampicil- 10.0 pts. by wt. of cephaloglycine dihydrate in 100 pts. by vol. of 80 percent strength aqueous THF and 6.1 pts. by wt. of 1-chlorocarbonyl-2-oxo-3-furylideneamino-imidazolidine are reacted, and worked up, as in Example 1.6. On slowly acidifying with 0.1 N HCL at 5°–10° C., 13.1 pts. by wt. of crystalline acid (Q=H) precipitate. The acid is dissolved in 500 pts. by vol. of acetone, small amounts of insoluble matter are filtered off and the filtrate is concentrated. The residue is suspended in 120 pts. by vol. of water and 1.5 N sodium hydroxide solution is added until the material has dissolved, the pH being kept at between 7.5 and 8.0. The solution is filtered, lyophilized or 940 pts. by vol. of acetone followed by 190 pts. by vol. of ethyl acetate are added and the sodium salt is then precipitated by dropwise addition of 380 pts. by vol. of ether. 7.8 pts. by wt. of crystalline sodium 7-{D-α-[(2-oxo-3-furylideneamino-imidazolidin-1-yl)-carbonylamino]-phenylacetamido}-3-acetoxymethyl-ceph-3-em-4-carboxylate of dec. pt. 215°–220° C., and of 95% β-lactam content, are obtained.

IR(KBr): 1,765, 1,730, 1,670, 1,615, 1,530, 1,480, 1,390, 1,265, 1,230, 1,020, 740 and 695 cm⁻¹.

NMR (D₂O/CD₃OD): 7.50 (s,2H), 7.30 (s,5H), 6.65 (1H), 6.45 (1H), 5.56 (d,1H), 5.38 (s,1H), 4.91 (pseudo-d, on which is superposed the signal of the exchangeable protons), 3.76 (6H), 2.03 (s,3H)δ.

$C_{27}H_{25}N_6NaO_9S.H_2O$: calculated: C 49.84; H 4.18; N 12.91; S 4.92; found: 49.4; H 4.6; N 12.9; S 4.9.

Part 8.5.

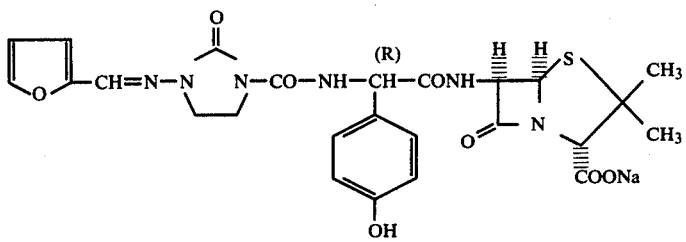

9.4 pts. by wt. of amoxicillin trihydrate in 100 pts. by vol. of 80 percent strength aqueous THF are reacted with 5.5 pts. by wt. of 1-chlorocarbonyl-2-oxo-3-(furan-2-aldimino)-imidazolidine as in Example 1.4. 0.1 pts. by wt. of sodium 6-{D-α-[(2-oxo-3-furylideneamino-imidazolidin-1-yl)-carbonylamino]-4-hydroxy-phenylacetamido}-penicillante are obtained.

IR (KBr): 1,775, 1,730, 1,670 and 1.615 cm$^{-1}$.

NMR (CD$_3$OD): 7.7–6.6 (8 H), 5.5 (3 H), 4.18 (s,1 H), 3.90 (s,4 H), 1.58 (s,3 H), 1.50 (s,3 H)δ.

Part 8.6

5.5 pts. by wt. of cephalexin-hydrate are suspended in 50 ml of 80 percent strength aqueous THF and reacted with 2.4 pts. by wt. of 1-chlorocarbonyl-2-oxo-3-furylidenamino-imidazolidine, and worked up, as in Example 1.3.

Yield: 4.2 pts. by wt. of sodium-7-{D-α-[(2-oxo-3-furylidenaminoimidazolidin-1-yl)-carbonylamino]-phenyl-acetamido}-3-methyl-ceph-3-em-4-carboxylate dec. pt. 218°–220° C.

IR(KBr): 1760, 1725, 1670, 1590 cm$^{-1}$

NMR(CD$_3$OD): 7,70(s,1H), 7,60(d,1H), 7,35(m,5H), 6,85 (d,1H), 6,50(dd,1H), 5,6(m,2H), 4,9 (on which is superposed the signal of the exchangeable protons), 3,85(s,4H), m 3,2 (superposed by the signal of the solvent), 1,95(s,3H)δ.

sive washing with water, ethanol and ether. Melting point 194°–197° C.

IR(KBr): 3,260, 1,700 (broad), 1,580 cm$^{-1}$.

NMR(d$_6$-DMSO): 7.92 and 7.78 (s, together 1H, syn- and anti-form), 7.16 and 7.10 (AB with superposed NH, 3H), m centred at 3.6 (4H)δ.

calculated: C 41.84; H 3.51; N 18.28; S 13.96; found: 41.9; 3.8; 18.0; 14.3.

Part 9.2.

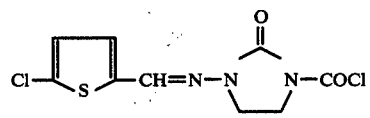

8.6 pts. by wt. of 1-(2-chlorothiophen-5-aldimino)-2-oxo-imidazolidine and 12.1 pts. by wt. of triethylamine in 60 pts. by vol. of abs. dioxane, and 12.0 pts. by wt. of trimethylchlorosilane in 25 pts. by vol. of abs. dioxane, and 3.9 pts. by wt. of phosgene, are reacted as in Example 2.2. The precipitate which has separated out after driving off the excess phosgene is filtered off and dried. 5.1 pts. by wt. of 1-chlorocarbonyl-2-oxo-3-(2-chlorothiophen-2-aldimino)-imidazolidine of dec. pt. 215°–220° C. are obtained.

IR (paraffin oil): 1,800 cm$^{-1}$.

Part 9.3.

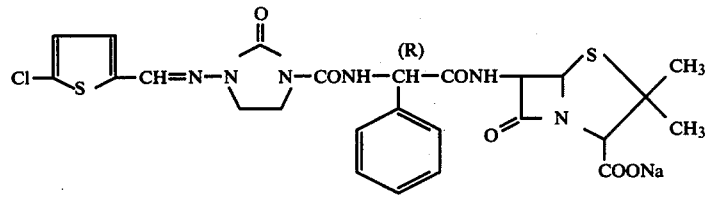

EXAMPLE 9

Part 9.1.

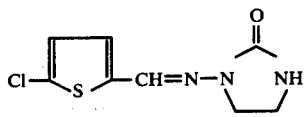

18.9 pts. by wt. of 2-oxo-imidazolidine, 15.2 pts. by wt. of sodium nitrite and 33.2 pts. by wt. of zinc dust are processed as in Example 2.1. and reacted with 29.1 pts. by wt. of 2-chlorothiophen-5-aldehyde. 36.0 pts. by wt. of 1-(2-chlorothiophen-5-aldimino)-2-oxo-imidazolidine are obtained, and the material was purified by succes- 13.9 pts. by wt. of ampicillin trihydrate in 140 pts. by vol. of 80% strength by volume aqueous THF are reacted with 5.0 pts. by wt. of 1-chlorocarbonyl-2-oxo-3-(2-chlorothiophen-5-aldimino)-imidazolidine as in Example 1.3. 7.5 pts. by wt. of sodium 6-{D-α-[(2-oxo-3-{2-chlorothiophen-5-aldimino}-imidazolidin-1-yl)-carbonylamino]-phenylacetamido}-penicillanate of dec. pt. 215°–225° C., and of 90% β-lactam content, are obtained.

IR(KBr): 1,765, 1,730, 1,670 and 1,605 cm$^{-1}$.

NMR(CD$_3$OD): 7.77 (s,1H), m centred at 7.32 (5H), 7.06 and 6.83 (AB,2H), 5.55 (s,1H), 5.42 (q,2H), 4.13 (s,1H), 3.77 (broad s,4H), 1.56 (s,3H), 1.48 (s,3H)δ.

$C_{25}H_{24}ClN_6NaO_6S_2 \cdot 1H_2O \cdot \frac{1}{4}$ ether: calculated: C 47.10; H 4.33; N 12.68; S 9.68; Cl 5.35; found: 47.0; 4.2; 12.5; 9.5; 4.9.

Part 9.4.

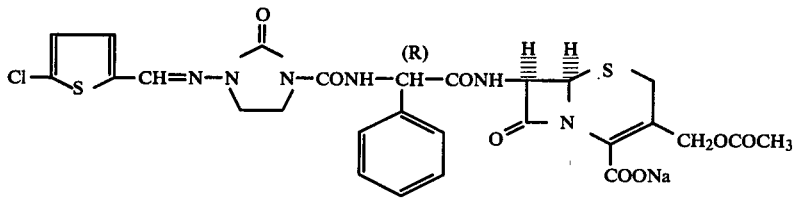

2.5 pts. by wt. of cephaloglycine dihydrate in 50 pts. by vol. of 80 percent strength THF are reacted with 1.7 pts. by wt. of 1-chlorocarbonyl-2-oxo-3-(2-chlorothiophen-5-aldimino)-imidazolidine as in Example 1.6. and the mixture is worked up. 2.5 pts. by wt. of sodium 7-{D-α-[(2-oxo-3-{2-chlorothiophen-5-aldimino}-imidazolidin-1-yl)-carbonylamino]-phenylacetamido}-3-acetoxymethyl-ceph-3-em-4-carboxylate are obtained.

IR(KBr): 1,760, 1,730, 1,670 and 1,600 cm$^{-1}$.

NMR(CD$_3$OD/D$_2$O): 7.87 (s, 1 H), 7.50 (s,5 H), 7.18 (d, 1 H), 6.93 (d,1 H), 5.65 (d,1 H), 5.53 (s,1 H), 5.05 (on which is superposed the signal of the exchangeable protons), 3.83 (6 H), 2.10 (s,3 H)δ.

C$_{27}$H$_{24}$ClN$_6$O$_8$S$_2$.H$_2$O calculated: C 46.26; H 3.74; N 11.99; S 9.14; Cl 5.07; found: C 46.3; H 3.9; N 11.9; S 9.5; Cl 5.0.

EXAMPLE 10

Part 10.1.

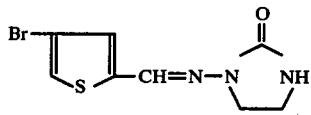

15.8 pts. by wt. of 2-oxo-imidazolidine, 12.6 pts. by wt. of sodium nitrite and 27.5 pts. by wt. of zinc dust are processed as in Example 2.1. and reacted with 31.5 pts. by wt. of 3-bromothiophen-5-aldehyde. 41.2 pts. by wt. of 1-(3-bromothiophen-5-aldimino)-2-oxo-imidazolidine are obtained and this material is purified by successive washing with water, ethanol and ether and is recrystallised from DMF.

Melting point 253°–255° C.
IR(KBr): 3,230 and 1,710 cm$^{-1}$.

NMR(d$_6$-DMSO): 7.77 (s,1H), 7.60 (s,1H), 7.28 (s,1H), 7.24 (s,1H), m centred at 3.6 (4H).

calculated: C 35.04; H 2.93; N 15.33; S 11.70; Br 29.15; found: 34.7; 2.9; 15.5; 11.8; 29.1.

Part 10.2.

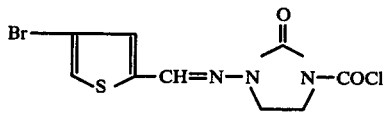

12.2 pts. by wt. of 1-(3-bromothiophen-5-aldimino)-2-oxo-imidazolidine and 14.1 pts. by wt. of triethylamine in 120 pts. by vol. of abs. dioxane, and 14.0 pts. by wt. of trimethylchlorosilane in 50 pts. by vol. of abs. dioxane and 4.6 pts. by wt. of phosgene, are reacted as in Example 2.2. The precipitate which has separated out after driving off the excess phosgene is filtered off, the filtrate is concentrated and the residue is triturated with abs, ether and filtered off. 7.5 pts. by wt. of 1-chlorocarbonyl-2-oxo-3-(3-bromothiophen-5-aldimino)-imidazolidine of melting point 165°–170° are obtained; this product still contains a proportion of starting material.

IR (paraffin oil): 1,780 and 1,690 cm$^{-1}$.

Part 10.3

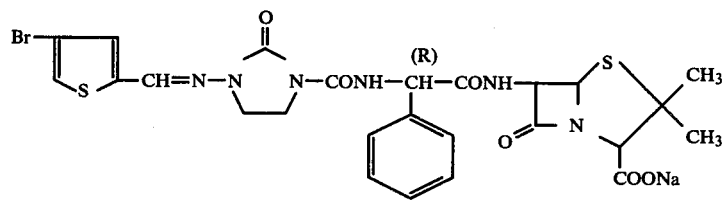

6.5 pts. by wt. of ampicillin trihydrate in 70 pts. by vol. of 80% strength by volume aqueous THF and 2.7 pts. by wt. of 1-chlorocarbonyl-2-oxo-3-(3-bromothiophen-5-aldimino)-imidazolidine are reacted as in Example 1.3. 2.2 pts. by wt. of sodium 6-{D-α-[(2-oxo-3-{3-bromothiophen-5-aldimino}-imidazolidin-1-yl)-carbonylamino]-phenylacetamido}-penicillanate of dec. pt. 210°–220° C., and of 85% β-lactam content, are obtained.

IR (KBr): 1,765, 1,730, 1,675 and 1,610 cm$^{-1}$.

NMR(CD$_3$OD): 7.83–7.20 (8H), 5.53 (s,1H), 5.42 (q,2H), 4.12 (s,1H), 3.78 (broad s,4H), 1.55 (s,3H), 1.48 (s,3H)δ.

Part 10.4.

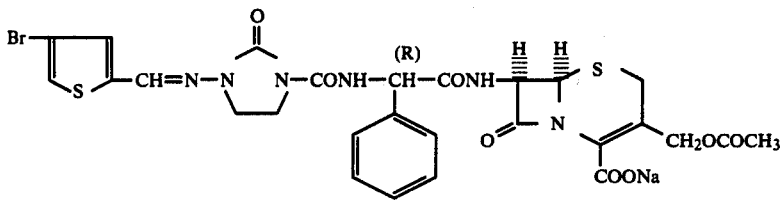

6.5 pts. by wt. of cephaloglycine dihydrate in 80 pts. by vol. of 80 per cent strength aqueous THF are reacted with 5.0 pts. by wt. of 1-chlorocarbonyl-2-oxo-3-(3-bromothiophen-5-aldimino)-imidazolidine and worked up, as in Example 1.6. 4.2 pts. by wt. of sodium 7-{D-α-[(2-oxo-3-{-bromothiophen-5-aldimino}-imidazolidin-1-yl)-carbonylamino]-phenylacetamido}-3-acetoxymethyl-ceph-3-em-4-carboxylate of dec. pt. 190°–5° C. are obtained.

IR (KBr): 1,760, 1,725, 1,670 and 1,605 cm$^{-1}$.

$C_{27}H_{24}BrN_6NaO_8S_2 \cdot H_2O$: calculated: C 43.50; H 3.52; N 11.28; S 8.59; found: C 43.8; H 3.8; N 10.8; S 8.1.

pts. by vol.) at 20° C., while stirring, and the mixture is then stirred for a further 90 minutes at the same temperature, after which it is left to stand for 16 hrs. The precipitate which has separated out is filtered off, well washed with water and dried over $P_4O_{10}$ in a desiccator.

Yield: 29.9 pts. by wt.

Melting point = 209°–210° C. (Kofler bench).

The substance still contains 0.28 mol equivalent of water. This is taken into account in the following calculated analytical data:

calculated: C 65.4; H 6.1; N 19.1; found: C 65.5; H 6.1; N 19.1.

Part 10.5.

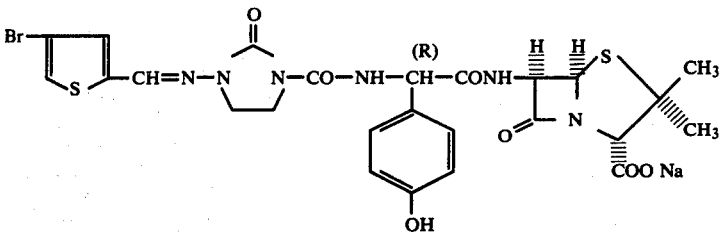

7.5 pts. by wt. of amoxicillin trihydrate in 100 pts. by vol. of 80 per cent strength aqueous THF are reacted with 6.0 pts. by wt. of 1-chlorocarbonyl-2-oxo-3-(3-bromothiophen-5-aldimino)-imidazolidine as in Example 1.4. 4.3 pts. by wt. of sodium 6-{D-α-[(2-oxo-3-{3-bromothiophen-5-aldimino}-imidazolidin-1-yl)-carbonylamino]-4-hydroxyphenylacetamido}-penicillanate are obtained.

IR (KBr): 1,760, 1,720, 1,670 and 1,605 cm$^{-1}$.

NMR (CD$_3$OD): 7.80 (s,1 H), 6.6–7.4 (6 H), 5.5 (m, 3H), 4.12 (s,1 H), 3.78 (s, broad, 4 H), 1.54 (s, 3 H), 1.48 (s,3 H)δ.

$C_{25}H_{24}BrN_6NaO_7S_2 \cdot H_2O$ calculated: C 41.50; H 3.91; S 8.84; found: C 41.7; H 4.3; S 8.3.

EXAMPLE 11

Part 11.1.

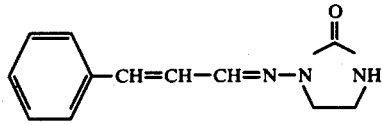

Cinnamaldehyde (18.5 pts. by wt.) are added to a solution of 1-amino-2-oxo-imidazolidine hydrochloride (21 pts. by wt.) in 1 N sodium hydroxide solution (150 pts. by vol.) at 20° C., while stirring, and the mixture is then stirred for a further 90 minutes at the same temperature, after which it is left to stand for 16 hrs. The precipitate which has separated out is filtered off, well washed with water and dried over $P_4O_{10}$ in a desiccator.

Yield: 29.9 pts. by wt.

Part 11.2.

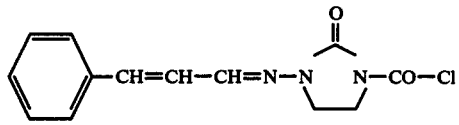

A solution of phosgene (4.3 pts. by vol.) in benzonitrile (15 pts. by vol.) is added dropwise to a mixture of 1-(cinnamylidene-amino)-2-oxo-imidazolidine (10 pts. by wt.), benzonitrile (50 pts. by vol.) and triethylamine (7.7 pts. by vol.), while stirring, and cooling with ice-/water. The mixture is then stirred for a further 4.5 hrs. whilst continuing the cooling. The precipitate formed is then filtered off, stirred in about 30 pts. by vol. of methylene chloride for 2 hrs. at 20° C., again filtered off and then dried over $P_4O_{10}$ in a desiccator.

Yield: 8.2 pts. by wt.

Melting point = 227°–230° C. (Kofler bench).

The substance still contains triethylamine hydrochloride, but this does not interfere with the further reaction.

IR spectrum (—CO—Cl): 1,800 cm$^{-1}$ (in paraffin oil).

Part 11.3.

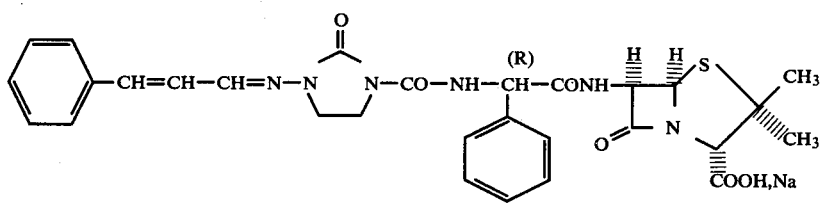

This penicillin is prepared in the manner described in Example 1.3. from ampicillin trihydrate (2.0 pts. by wt.) and 1-chlorocarbonyl-2-oxo-3-(cinnamylideneamino)-imidazolidine (2.06 pts. by wt.; an excess is used because of the triethylamine present in the substance).

Yield: 2.1 pts. by wt. of sodium D-α-[(2-oxo-3-cinnamylideneamino-imidazolidin-1-yl)-carbonylamino]-benzylpenicillin.

The penicillin contains 1.5 mol equivalents of $H_2O$ and 0.36 mol equivalent of sodium 2-ethylhexanoate (according to the NMR spectrum). This was taken into account in the following calculated analytical data:

Calculated: C 53.6; H 5.2; N 11.8; S 4.5; found: C 53.6; H 5.7; N 11.7; S 4.6.

IR spectrum (in paraffin oil) (carbonyl region): 1,770, 1,740, 1,670, 1,615 and 1,555–1,520 $cm^{-1}$.

Part 11.5.

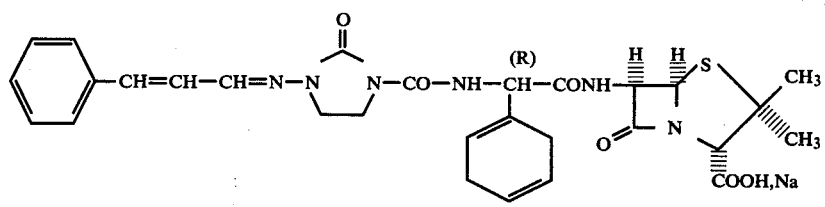

β-Lactam content: 82%.

According to the NMR spectrum, the substance contains about 2.6 mol equivalents of $H_2O$ and 0.56 mol equivalent of sodium 2-ethylhexanoate. This was taken into account in the following calculated analytical data:

calculated: C 53.6; H 5.6; N 11.2; S 4.3; found: C 53.6; H 5.6; N 10.8; S 4.3.

NMR signals at τ = 2.3–3.2 (13 H), 4.45 (1 H), 4.45–4.75 (AB, 2 H), 5.9 (1 H), 6.1–6.4 (4 H), 8.5 (3 H) and 8.55 ppm (3 H).

IR spectrum (in paraffin oil) (carbonyl region): 1,770, 1,730, 1,670, 1,610 and 1,525 $cm^{-1}$.

This penicillin is prepared in the manner described in Example 1.3. from epicillin (1.5 pts. by wt.) and 1-chlorocarbonyl-2-oxo-3-(cinnamylidene-amino)-imidazolidine (1.77 pts. by wt.; an excess is used, since the material still contained triethylamine hydrochloride).

Yield: 1.6 pts. by wt. of sodium D-α-[(2-oxo-3-cinnamylidene-amino-imidazolidin-1-yl)-carbonylamino]-α-(1,4-cyclohexadien-1-yl)-methylpenicillin.

β-Lactam content: 82%.

According to the NMR, the penicillin contained about 2 mol equivalents of water and 0.36 mol equiva- Part 11.4.

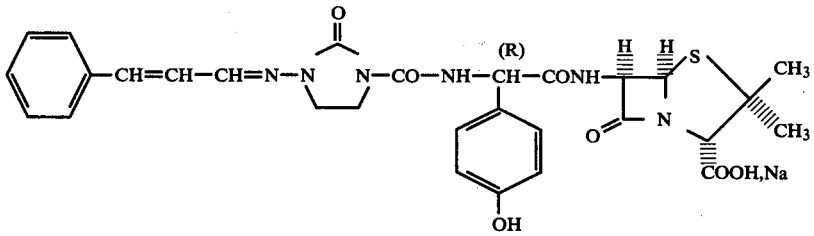

This penicillin is prepared in the manner described in Example 1.3. from amoxicillin trihydrate (1.5 pts. by wt.) and 1-chlorocarbonyl-2-oxo-3-(cinnamylidene-amino)-imidazolidine (1.49 pts. by wt.).

Yield: 1.3 pts. by wt. of sodium D-α-[(2-oxo-3-cinnamylidene-amino-imidazolidin-1-yl)-carbonylamino]-p-hydroxy-benzylpenicillin.

β-Lactam content: 88%.

lent of sodium 2-ethylhexanoate. This was taken into account in the calculated analytical data:

calculated: C 54.0; H 5.6; N 11.8; S 4.5; found: C 54.0; H 5.7; N 11.7; S 4.5.

IR spectrum (in paraffin oil) (carbonyl region): 1,772, 1,730, 1,650, 1,610 and 1,530 $cm^{-1}$.

NMR signals at τ = 2.25–3.15 (8 H), 4.05 (1 H), 4.3 (2 H), 4.5 (2 H), 5.0 (1 H), 5.8 (1 H), 6.05–6.4 (4 H), 7.15–7.45 (4 H), 8.4 (3 H) and 8.46 ppm (3 H).

Part 11.6.

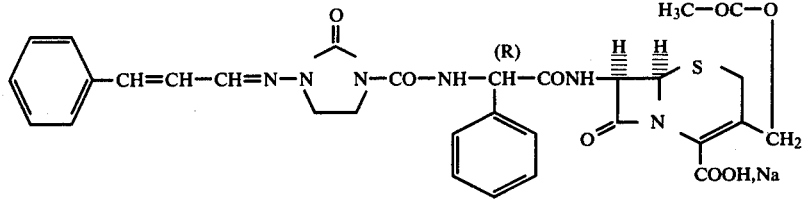

This cephalosporin is prepared analogously to the manner described for penicillins in Examples 1.3. and 1.6., from cephaloglycine dihydrate (1.5 pts. by wt.) and 1-chlorocarbonyl-2-oxo-3-(cinnamylidene-amino)-imidazolidine (1.08 pts. by wt.; an excess is used since the substance still contains triethylamine hydrochloride). After removing the tetrahydrofurane at pH 7.0, a precipitate which is insoluble in water and ethyl acetate is filtered off and is stirred with a mixture of ethyl acetate and water at pH 2.0. After filtering off, the product is stirred with 10 pts. by vol. of dimethylformamide, insoluble matter is filtered off, and after diluting the filtrate with 150 pts. by vol. of ether the sodium salt is precipitated.

Yield: 0.5 pts. by wt. of sodium 7-{D-α-[(2-oxo-3-cinnamylidene-amino-imidazolidin-1-yl)-carbonylamino]-phenylacetamido}-3-acetoxymethyl-ceph-3-em-4-carboxylate.

β-Lactam content: 80%.

According to the NMR, this cephalosporin contains about 3 mol equivalents of water and 0.65 mol equivalent of sodium 2-ethylhexanoate. This was taken into account in the following calculated analytical data:

Melting point = 195° C. (Kofler bench).

calculated: C 56.9; H 5.3; N 29.5; O 8.4; found: C 56.9; H 5.2; N 30.0; O 0.80.

Part 12.2.

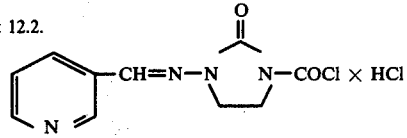

A solution of phosgene (1.35 pts. by vol.) in tetrahydrofurane (10 pts. by vol.) is added to a suspension of 1-(3-pyridyl-methylideneamino)-2-oxo-imidazolidine (3.0 pts. by wt.) in a mixture of benzonitrile (30 pts. by vol.) and triethylamine (2.6 pts. by vol.), while cooling with ice water. After 20 minutes, the mixture is allowed to come to 20° C. and is then stirred at this temperature overnight. The precipitate present is then filtered off, washed with ether and then with dichloromethane and dried.

Yield: 4.2 pts. by wt.

IR spectrum (CO.Cl): 1,800 cm⁻¹ (in paraffin oil)

Melting point = 252° C. (Kofler bench)

Part 12.3.

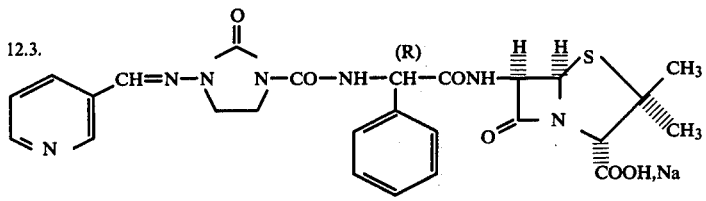

calculated: C 52.3; H 5.4; N 10.1; S 3.9; found: C 52.4; H 5.6; N 10.3; S 3.8.

IR spectrum (in paraffin oil) (carbonyl region): 1,770, 1,730, 1,668, 1,612 and 1,540 cm⁻¹.

NMR signals (in deuterated DMF) at τ=2.1–2.9 (13H), 3.9–4.3 (2H),4.75–5.1 (3 H), 4.0 (4 H), 6.6 (2 H) and 7.9 ppm (3 H).

EXAMPLE 12

Part 12.1.

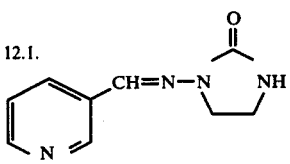

Pyridin-3-aldehyde (10.7 pts. by wt.) is added to a solution of 1-amino-2-oxo-imidazolidine (10.1 pts. by wt.) in a mixture of methanol and water (50 pts. by vol. each) and the mixture is then stirred for about 20 hrs. at 20° C. The precipitate formed is then filtered off, washed with water and a little methanol and dried over P₄O₁₀ in vacuo at 60° C.

Yield: 16.5 pts. by wt.

This penicillin is prepared in the manner described in Example 1.3. from ampicillin trihydrate (1.0 pts. by wt.) and 1-chlorocarbonyl-2-oxo-3-(3-pyridyl-methylideneamino)imidazolidine (0.63 pts. by wt.). On acidifying the reaction solution which has been freed from the tetrahydrofurane and covered with ethyl acetate, a part of the penicillin is obtained as free acid which is insoluble in ethyl acetate (0.20 pts. by wt.; IR spectrum [carbonyl region]: 1,775, 1,725, 1,670 and 1,520 cm⁻¹ in paraffin oil). The sodium salt is obtained from the organic phase by precipitation with sodium 2-ethylhexanoate solution.

Yield: 0.70 pts. by wt. of sodium D-α-{[(2-oxo-3-(3-pyridyl-methylideneamino)-imidazolidin-1-yl]-carbonylamino}-benzylpenicillin.

β-Lactam content: 90%

According to the NMR spectrum, the penicllin contains about 3.3 mol equivalents of water and 0.13 mol equivalent of sodium 2-ethylhexanoate. This was taken into account in the following calculated analytical data:

calculated: C 48.6; H 5.3; N 14.7; S 4.8; found: C 48.5; H 5.8; N 14.5; S 4.8.

IR spectrum (in paraffin oil) (carbonyl region): 1,768, 1,722, 1,667, 1,625, 1,600, 1,550 and 1,525 cm⁻¹.

NMR signals at τ=1.0–1.2 (1 H), 1.35–1.55 (1 H), 1.6–1.85 (1 H), 2.15 (1 H), 2.3–2.8 (6 H), 4.3 (1 H), 4.3–4.6 (AB;2H), 5.8 (1 H), 5.9–6.2 (4 H), 8.4 (3 H) and 8.45 ppm (3H).

EXAMPLE 13

Part 13.3.

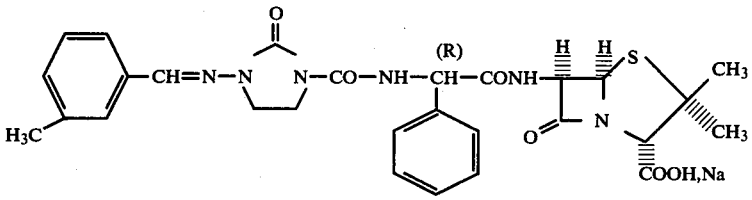

Part 13.1.

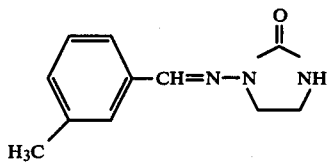

3-Methylbenzaldehyde is added to a mixture of 1-amino-2-oxo-imidazolidine hydrochloride (14.0 pts. by wt.) and 1 N sodium hydroxide solution (100 pts. by vol.) and the mixture is then stirred for a further 5 hrs. at 20° C. The precipitate formed is then filtered off, washed with water and dried.

Yield: 20.3 pts. by wt. Melting point=205°–207° C. (Kofler bench).

Part 13.2.

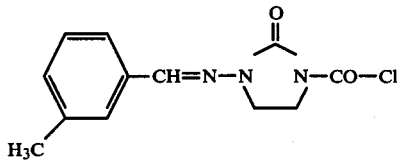

A solution of trimethylchlorosilane (9.65 pts. by wt.) in benzene (50 pts. by vol.) is added dropwise over the course of one hour to a gently boiling mixture of 1-(3-methylbenzylidene-amino)-2-oxo-imidazolidine (12.1 pts. by wt.), benzene (150 pts. by vol.) and triethylamine (13.4 pts. by vol.). The mixture is then boiled under reflux for 20 hrs. and the triethylamine hydrochloride is filtered off hot and rinsed with hot benzene. A solution of phosgene (4.7 pts. by vol.) in benzene (30 pts. by vol.) is added to the combined filtrates which have been cooled to 10° C. and the mixture is then left to stand for 48 hrs. at 20° C. Thereafter the precipitate formed is filtered off, washed with benzene, then triturated with methylene chloride (40 pts. by vol.), and then dried.

Yield: 3.2 pts. by wt. Melting point=209°–210° C. (Kofler bench).

calculated: C 54.3; H 4.5; Cl 13.4; N 15.8; found: C 54.5; H 4.6; Cl 13.5; N 15.4.

IR spectrum (CO.Cl): 1,810 cm$^{-1}$ (in paraffin oil).

This penicillin is obtained when ampicillin trihydrate (2.0 pts. by wt.) and 1-chlorocarbonyl-2-oxo-3-(3-methylbenzylidene-amino)-imidazolidine (1.6 pts. by wt.) are reacted in the manner described in Example 1.3.

Yield: 2.55 pts. by wt. of sodium D-α-{[2-oxo-3-(3-methylbenzylidene-amino)-imidiazolidin-1-yl]-carbonylamino}-benzylpenicillin.

β-Lactam content: 90%.

According to the NMR spectrum, the penicillin contains a little sodium 2-ethylhexanoate (about 0.06 mol equivalent) and water (3 mol equivalents). This was taken into account in the calculate analytical data:

calculated: C 52.1; H 5.4; N 12.6; S 4.8; found: C 51.9; H 6.3; N 12.4; S 4.9.

IR spectrum (in paraffin oil) (carbonyl region): 1,770, 1,730, 1,675, 1,612 and 1,530 cm$^{-1}$.

NMR signals (CD$_3$OD) at τ=2.25–2.9 (10 H), 4.35 (1 H), 4.35–4.65 (AB, 2 H), 5.85 (1 H), 6.1–6.4 (4 H), 7.7 (3 H), 8.4 (3 H) and 8.5 ppm (3 H).

Part 13.4.

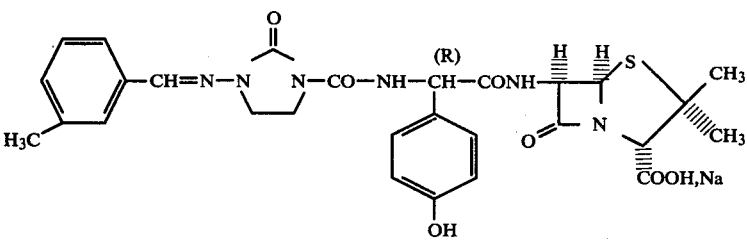

This penicillin is obtained when, analogously to Example 1.3., amoxicillin trihydrate (1.0 pts. by wt.) and 1-chlorocarbonyl-2-oxo-3-(3-methylbenzylidene-amino)-imidazolidine (0.73 pts. by wt.) are reacted with one another.

Yield: 1.1 pts. by wt. of crystalline sodium D-α-{[2-oxo-3-(3-methylbenzylidene-amino)-imidazolidin-1-yl]-carbonylamino}-p-hydroxybenzylpenicillin.

β-Lactam content: 90%.

According to the NMR spectrum, the penicillin contains a little sodium 2-ethylhexanoate (0.16 mol equivalent) and water (2.9 mol equivalents). This was taken into account in the following calculated analytical data:

calculated: C 50.5; H 5.3; N 12.1; S 4.6; found: C 50.5; H 5.4; N 11.9; S 4.6.

IR spectrum (in paraffin oil) (carbonyl region): 1,790, 1,765, 1,720, 1,690, 1,660, 1,612, 1,590, 1,550 and 1,510 cm$^{-1}$.

NMR signals (in CD$_3$OD) at $\tau=2.2$–3.3 (9 H), 4.4–4.65 (3 H), 5.85 (1 H), 6.0–6.3 (4 H), 7.65 (3 H), 8.4 (3 H) and 8.5 ppm (3 H).

Part 13.5.

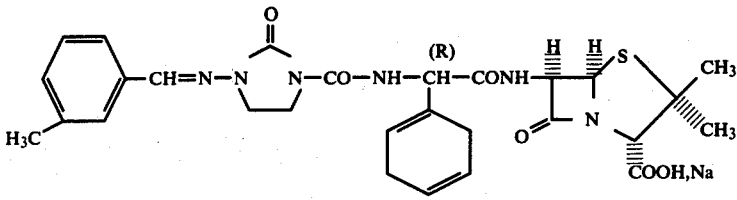

This penicillin is obtained when epicillin (1.0 pts. by wt.) is reacted with 1-chlorocarbonyl-2-oxo-3-(3-methylbenzylidene-amino)-imidazolidine (0.91 pts. by wt.) in the manner described in Example 1.3. On precipitating the sodium salt, 0.8 pt. by wt. of amorphous penicillin salt was first obtained, and on further precipitation from its mother liquor, 0.9 pt. by wt. of crystalline sodium D-α-{[2-oxo-3-(3-methylbenzylidene-amino)-imidazolidin-1-yl]-carbonylamino}-α-(1,4-cyclohexadien-1-yl)-methylpenicillin was obtained.

IR spectrum of the amorphous salt (in paraffin oil) (carbonyl region); 1,770, 1,730, 1,670, 1,610 and 1,525 cm$^{-1}$.

IR spectrum of the crystalline salt (in paraffin oil) (carbonyl region): 1,790, (1,775), 1,740, 1,712, 1,660, 1,600, 1,575 and 1,520 cm$^{-1}$.

NMR signals (in CD$_3$OD) at $\tau=2.1$–2.8 (5 H), 4.05 (1 H), 4.3 (2 H), 4.5 (2 H), 5.0 (1 H), 5.8 (1 H), 6.1 (4 H), 7.25 (4 H), 7.65 (3 H), 8.35 (3 H) and 8.45 ppm (3 H).

Part 13.6.

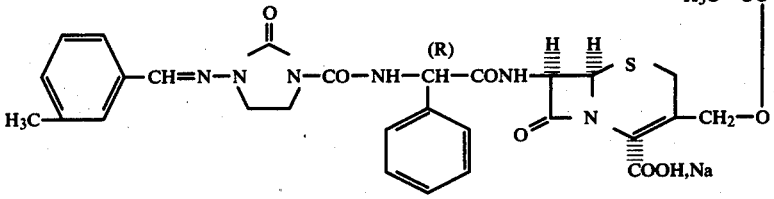

This cephalosporin is obtained when cephaloglycine dihydrate (1.0 pts. by wt.) is reacted with 1-chlorocarbonyl-2-oxo-3-(3-methylbenzylideneamino)-imidazolidine (0.69 pts. by wt.) in the manner described for penicillins in Examples 1.3. and 1.6. The sodium salt separated out as a gel-like precipitate which could not be filtered off. For this reason, all volatile matter was stripped off and the residue was treated with dry ether. This gave the cephalosporin salt as a loose white powder.

Yield: 1.2 pts. by wt. of sodium 7-{D-α-[(2-oxo-3-m-methyl-benzylideneamino-imidazolidin-1-yl)-carbonylamino]-phenylacetamido}-3-acetoxymethyl-ceph-3-em-4-carboxylate.

β-Lactam content: 90%.

The cephalosporin salt contains about 2.9 mol equivalents of water. This was taken into account in the calculated analytical data:

calculated: C 51.2; H 4.9; N 11.9; S 4.6; found: C 51.4; H 5.5; N 11.7; S 4.7.

IR spectrum (in paraffin oil) (carbonyl region): 1,765 (shoulder), 1,740, 1,660, 1,610 and 1,535 cm$^{-1}$.

NMR signals (in d$_7$-DMF) at $\tau=1.85$–2.8 (10 H), 3.9–4.3 (2 H), 4.7–5.0 (3 H), 5.8–6.1 (4 H), 6.4–6.7 (2 H), 7.5 (3 H) and 7.8 ppm, (3 H).

EXAMPLE 14

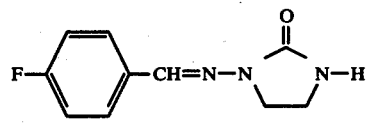

This substance is obtained in the manner described in Example 13.1. from 1-amino-2-oxo-imidazolidine hydrochloride (14.0 pts. by wt.) and 4-fluorobenzaldehyde (12.8 pts. by wt.).

Yield: 20.4 pts. by wt. Melting point=229°–230° C. (Kofler bench).

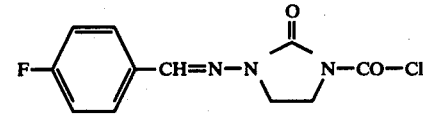

A solution of phosgene (4.2 pts. by vol.) in benzonitrile (10 pts. by vol.) is added dropwise to a mixture of 1-(4-fluorobenzylidene-amino)-2-oxo-imidazolidine (6.0 pts. by wt.), benzonitrile (50 pts. by vol.) and triethylamine (8 pts. by vol.) while cooling with ice/water, and stirring, and the mixture is then stirred for a further 3 hrs. at 20° C. The precipitate is then filtered off, suspended in methylene chloride (240 pts. by vol.) again filtered off and dried.

Yield: 0.9 pts. by wt. (the mother liquor contains some more of this substance).

The substance is not quite free from triethylamine hydrochloride, but this did not interfere with the further reaction.

IR spectrum (CO.Cl): 1,820/1,810 cm$^{-1}$ (in paraffin oil).

Melting point=240°–247° C., with decomposition (Kofler bench).

Part 14.3 -continued

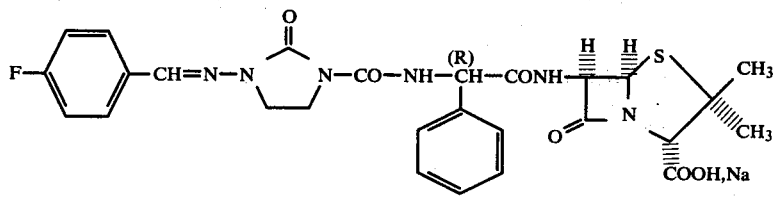

This penicillin is obtained when ampicillin trihydrate (1.0 pts. by wt.) and 1-chlorocarbonyl-2-oxo-3-(4-fluorobenzylidene-amino)-imidazolidine (0.8 pts. by wt.) are reacted with one another in the manner described in Example 1.3.

Yield: 1.2 pts. by wt. of crystalline sodium D-α-{[2-oxo-3-(4-fluorobenzylidene-amino)-imidazolidin-1-yl]carbonylamino}-benzylpenicillin.

β-Lactam content: 93%.

According to the NMR spectrum, the penicillin contains about 1.7 mol equivalents of water. This was taken into account in the calculated analytical data:

calculated: C 51.1; H 4.6; N 13.2; S 5.0; found: C 51.1; H 5.4; N 13.2; S 5.1.

IR spectrum (in paraffin oil) (carbonyl region): 1,790 (1,767), 1,730, 1,702, 1,670 (shoulder), 1,660 and 1,602 $cm^{-1}$.

NMR signals (in $CD_3OD$) at $\tau=2.1-3.1$ (10 H), 4.4 (1 H), 4.4–4.65 (AB, 2 H), 5.85 (1 H), 6.0–6.3 (4H), 8.45 (3 H) and 8.55 ppm (3 H).

Part 14.4.

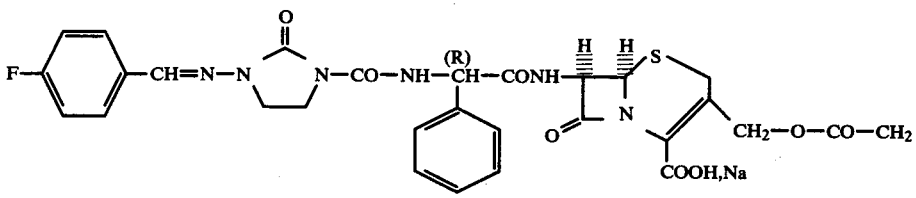

This cephalosporin is obtained when cephloglycine dihydrate (1.0 pts. by wt.) is reacted with 1-chlorocarbonyl-2-oxo-3-(4-fluorobenzylidene-amino)-imidazolidine (0.7 pts. by wt.) in the manner described for penicillins in Examples 1.3. and 1.6. Since the sodium salt separated out as a gel and was difficult to filter in this form, all volatile material was removed in vacuo and the residue was treated with a mixture of ether and methanol (10/1).

As a result of this treatment, the sodium salt was converted to a loose white powder.

Yield: 0.5 pts. by wt. of sodium 7-{D-α-[(2-oxo-3-p-fluorobenzylideneamino-imidazolidin-1-yl)-carbonylamino]-phenylacetamido}-3-acetoxymethyl-ceph-3-em-4-carboxylate.

β-Lactam content: 91%.

According to the NMR spectrum, the cephalosporin contains about 0.13 mol equivalent of sodium 2-ethylhexanoate and 1.7 mol equivalents of water. This was taken into account in the calculated analytical data:

calculated: C 50.7; H 4.4; N 11.8; S 4.5; found: C 50.7; H 4.4; N 11.8; S 4.6.

IR spectrum (in paraffin oil) (carbonyl region): 1,775 (shoulder), 1,760 (shoulder), 1,735, 1,680, 1,610 and 1,550–1,520 $cm^{-1}$.

NMR signals (in $CD_3OD$) at $\tau=2.1-2.9(10)$, 4.2–4.35 (1 H), 4.4(1 H), 5.0–5.2(3 H), 6.1(4 H), 6.5–6.7 (2 H) and 8.0 ppm (3 H).

EXAMPLE 15

Part 15.1.

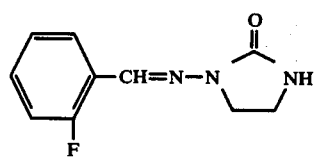

This substance is obtained as in Example 13.1. from 1-amino-2-oxo-imidazolidine hydrochloride (14.0 pts. by wt.) and 2-fluorobenzaldehyde (12.7 pts. by wt.) in a yield of 17.6 pts. by wt.

Melting point 214°–216° C. (Kofler bench).

Part 15.2.

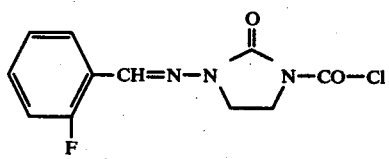

A solution of phosgene (4.2 pts. by vol.) in benzonitrile (10 pts. by vol.) is added dropwise to a mixture of 1-(2-fluorobenzylidene-amino)-2-oxo-imidazolidine (6.0 pts. by wt.), benzonitrile (50 pts. by vol.) and triethylamine (8 pts. by vol.), while stirring and cooling with ice/water. The mixture is then stirred for a further 3 hrs. at 20° C. The product is then filtered off and washed with ether and the precipitate is suspended in about 120 pts. by vol. of methylene chloride, again filtered off and dried.

Yield: 5.6 pts. by wt.

Melting point=230° C. (Kofler bench).

IR spectrum (CO.Cl): 1,800 (with a shoulder at about 1,815) $cm^{-1}$.

The substance contains a little triethylamine hydrochloride but this did not interfere with the further reaction.

Part 15.3.

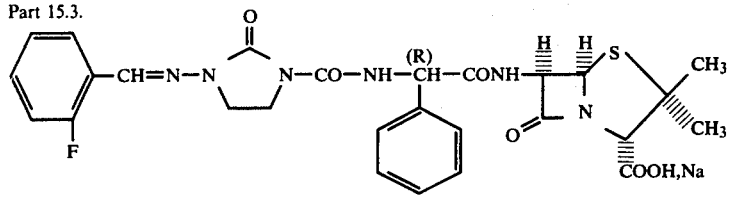

This penicillin is obtained from ampicillin trihydrate (1.0 pts. by wt.) and 1-chlorocarbonyl-2-oxo-3-(2-fluorobenzylidene-amino)-imidazolidine (0.8 pts. by wt.) when these are reacted with one another by the method described in Example 1.3.

Yield: 0.55 pts. by wt. of crystalline sodium D-α-{[2-oxo-3-(2-fluorobenzylidene-amino)-imidazolidin-1-yl]-carbonylamino}-benzylpenicillin.

β-Lactam content: 90%.

According to the NMR spectrum, the penicillin contains about 2.9 mol equivalents of water. This was taken into account in the following calculated analytical data:

calculated: C 49.4; H 4.9; N 12.8; S 4.9; found: C 49.4; H 4.9; N 12.6; S 5.3;

IR spectrum (in paraffin oil) (carbonyl region): 1,793 (1,775), 1,740 (1,700, 1,680 both a shoulder), 1,660, 1,610, 1,560 and 1,520 cm$^{-1}$.

NMR signals (in CD$_3$OD) at τ=1.8–3.1 (10), 4.4(1 H), 4.4–4.65(2 H), 5.8 (1 H), 6.0–6.3(4 H), 8.45 (3 H) and 8.55 ppm (3 H).

Part 15.4.

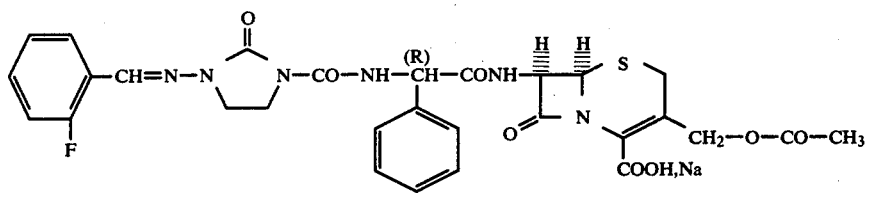

This cephalosporin is obtained from cephaloglycine dihydrate (1.5 pts. by wt.) and 1-chlorocarbonyl-2-oxo-3-(2-fluorobenzylidene-amino)-imidazolidine (1.07 pts. by wt.) in accordance with the process of preparation described for penicillins in Examples 1.3. and 1.6.

On working up, acidification to pH 2 gives a part of the cephalosporin as free acid which is insoluble in water and ethyl acetate (0.2 pts. by wt.; IR spectrum [carbonyl region]: 1,780, 1,745, 1,670 and 1,540 cm$^{-1}$ in paraffin oil). To the extent that the cephalosporin formed is dissolved in the organic phase, it is obtained therefrom in a yield of 0.8 pts. by wt. as sodium 7{-D-α-[(2-oxo-3-o-fluorobenzylidene-amino-imidazolidin-1-yl)-carbonylamino]-phenylacetamido}-3-acetoxymethyl-ceph-3-em-4-carboxylate.

The data which follow relate to the sodium salt.

β-Lactam content: 91%.

According to the NMR spectrum, the cephalosporin contains about 2.8 mol equivalents of water and 0.05 mol equivalent of sodium 2-ethylhexanoate. This was taken into account in the calculated analytical data:

calculated: C 49.2; H 4.5; N 11.7; S 4.5; found: C 49.1; H 4.3; N 11.7; S 4.9;

IR spectrum (in paraffin oil) (carbonyl region): 1,780, 1,730, 1,670, 1,610 and 1,530 cm$^{-1}$. NMR signals (in D$_7$-DMF) at τ=1.8–2.9(10 H), 4.0–4.4(2 H), 4.8–5.1 (3 H), 5.8–6.2(4 H), 6.5–6.75(2 H) and 7.95 ppm (3 H).

EXAMPLE 16

Part 16.1.

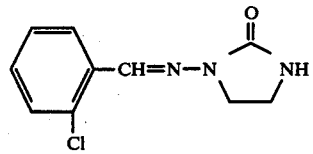

47.5 pts. by wt. of 2-oxo-imidazolidine, 38.0 pts. by wt. of sodium nitrite and 82.5 pts. by wt. of zinc dust are processed as in Example 2.1. and reacted with 64.0 pts. by wt. of 2-chlorobenzaldehyde. 65.0 pts. by wt. of 1-(2-chloro)-benzalimino-2-oxo-imidazolidine are obtained and are recrystallised from ethanol. Melting point 216°–17° C.

Part 16.2.

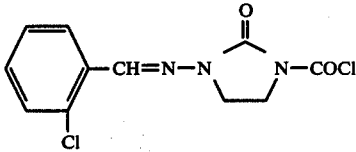

50.0 pts. by wt. of 1-(2-chloro)-benzalimino-2-oxo-imidazolidine and 73.0 pts. by wt. of triethylamine in 400 pts. by vol. of abs. dioxane, and 72.7 pts. by wt. of trimethylchlorosilane in 150 pts. by vol. of abs. dioxane, and 44.5 pts. by wt. of phosgene, are reacted as in Example 2.2. 37.2 pts. by wt. of 1-chlorocarbonyl-2-oxo-3-(2-chloro)-benzalimino-imidazolidine are obtained and are recrystallised from acetonitrile. Melting point 233°–7° C.

IR (Paraffin oil): 1,800 cm$^{-1}$.

Calculated: C 46.18; H 3.17; N 14.68; Cl 24.78; found: C 46.1; H 3.2; H 14.6; Cl 24.7.

Part 16.3.

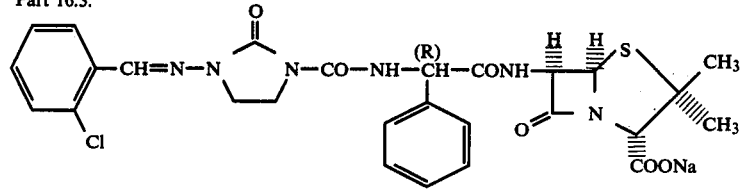

14.1 pts. by wt. of ammpicillin trihydrate in 150 pts. by vol. of 80 percent strength aqueous THF are reacted with 5.0 pts. by wt. of 1-chlorocarbonyl-2-oxo-3-(2-chloro)-benzalimino-imidazolidine as in Example 1.3. 11.3 pts. by wt. of sodium 6-{D-α-[(2-oxo-3-{2-chloro}-benzal-imino-imidazolidin-1yl)-carbonylamino]-phenylacetamido}-penicillanate of dec. pt. 215°–220° C. are obtained.

β-Lactam content: 83%.

IR(KBr): 1,765, 1,730, 1,675 and 1,605 cm$^{-1}$.

NMR-(CD$_3$OD): 7.92 (s with exchangeable m, 2 H), m centered at 7.3(8 H), 5.55(s,1 H), 5.42(AB system, 2 H), 4.12 (s,1 H), 3.83(s, broad,4 H), 1.58(s,3 H), 1.50(s,3 H)δ.

C$_{27}$H$_{26}$ClN$_6$NaO$_6$S.2H$_2$O: Calculated: C 49.36; H 4.60; N 12.79; found: C 49.4; H 4.6; N 12.7.

Part 16.4.

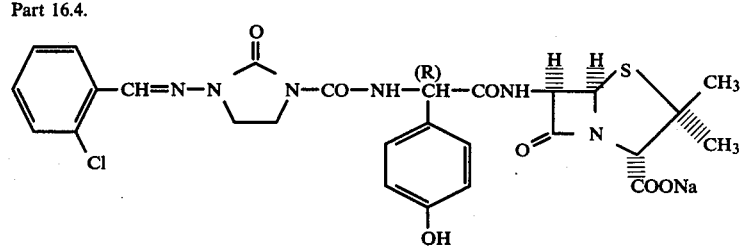

6.3 pts. by wt. of amoxicillin trihydrate in 80 pts. by vol. of 80 percent strength aqueous THF are reacted with 2.9 pts. by wt. of 1-chlorocarbonyl-2-oxo-3-(2-chloro)-benzalimino-imidazolidine as in Example 1.4.

8.5 pts. by wt. of sodium 6-{-α-[(2-oxo-3-{2-chloro}-benzalimino-imidazolidin-1-yl)carbonylamino]-4-hydroxy-phenylacetamido}-pencillanate are obtained.

IR (KBr): 1,760, 1,720, 1,655 and 1,600 cm$^{-1}$.

NMR (CD$_3$OD): 7.95 s(1 H), 7.5–6.8 (8 H), 5.5(m, 3 H), 4.20 (s,1 H), 3.92 (s,broad 4 H), 1.60 (s,3 H), 1.50(s,3 H)δ.

Part 16.5.

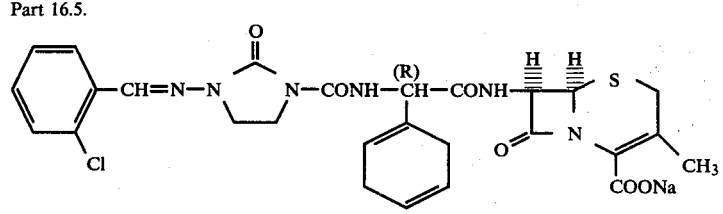

10.5 pts. by wt. of cephradin in 100 pts. by vol. of 80 percent strength aqueous THF are reacted with 7.5 pts. by wt. of 1-chlorocarbonyl-2-oxo-3-(2-chloro)-benzalimino-imidazolidine as in Example 1.3. 10.9 pts. by wt. of sodium 7-{D-α[(d2-oxo-3(2-chloro}-benzalimino-imidazolidin-1-yl)-carbonylamino]-cyclohex-1,4-dienyl(1)-acetamido}-3-methyl-ceph-3-em-4-carboxylate of dec. pt. 220° C. are obtained.

IR(KBr): 1,770, 1,735, 1,665 and 1,590 cm$^{-1}$.

C$_{27}$H$_{26}$C/N$_6$NaO$_6$S.2H$_2$O:

calculated: C 49.36; H 4.66; N 12.79; S 4.88; Cl 5.39; found: C 48.9; H 4.5; N 12.4; S 4.4; Cl 5.3.

Part 16.6.

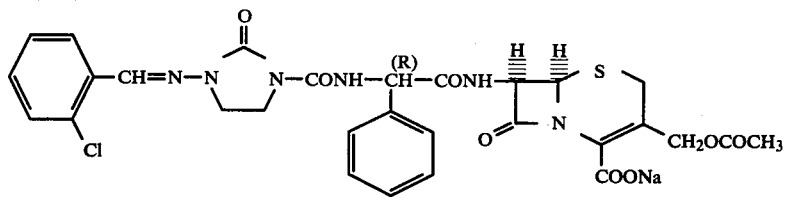

5.0 pts. by wt. of cephaloglycine dihydrate in 100 pts. by vol. of 80 percent strength aqueous THF are reacted with 3.3 pts. by wt. of 1-chlorocarbonyl-2-oxo-3-(2-chloro)-benzalimino-imidazolidine as in Example 1.6.

6.7 pts. by wt. of sodium 7-{D-α[(2-oxo-3-{2-chloro}-benzalimino-imidazolidin-1yl)-carborylamino]-phenylacetamido}-3-acetoxy-methyl-ceph-3-em-4-carboxylate of dec. pt. 195°–200° C. are obtained.

IR (KBr): 1,760, 1,725, 1,670 and 1,600 cm$^{-1}$.

NMR(CD$_3$OD/D$_2$O): 7.2–8.0(aromatic protons and —CH=N—), 5.65(d,1 H), 5.50(s,1 H), 5.05(d, on which is superposed the signal of the exchangeable protons), 3.8 (6 H), 2.10 (s,3H)δ.

C$_{29}$H$_{26}$ClN$_6$NaO$_8$S. S.H$_2$O :

calculated: C 50.11; H 4.21; N 12.09; S 4.63; found: C 50.1; H 4.1; N 12.1; S 4.8.

Part 17.4.

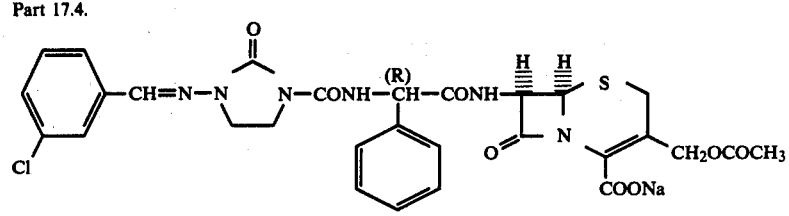

EXAMPLE 17

Part 17.1.

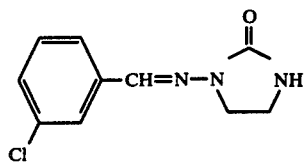

47.6 pts. by wt. of 2-oxo-imidazolidine, 34.5 pts. by wt. of sodium nitrite and 78.4 pts. by wt. of zinc dust are processed as in Example 1.1. and stirred with 77.0 pts. by wt. of 3-chlorobenzaldehyde overnight. 65.7 pts. by wt. of 1-(3-chloro)benzalimino-2-oxo-imidazolidine of melting point 210°-212° C. are obtained.

IR(KBr): 3,230, 3,120, 1,715, 1,475 and 1,405 cm$^{-1}$.
NMR(D$_6$-DMSO): m centred about 7.5 (aromatic protons, —CH=N— and NH; 6 H), 3.65 (m,4 H)$\delta$.
calculated: C 53.70; H 4.51; N 18.79; Cl 15.85; found: C 54.0; H 4.7; N 18.4; Cl 16.2.

Part 17.2.

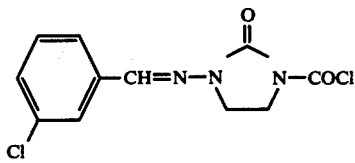

A solution of 43.3 pts. by wt. of trimethylchlorosilane in 80 pts. by vol. of abs. dioxane is added dropwise to a boiling solution of 30.0 pts. by wt. of 1-(3-chloro)-benezalimino-2-oxo-imidazolidine and 43.4 pts. by wt. of triethylamine in 250 pts. by vol. of abs. dioxane, and the mixture is reacted with 26.4 pts. by wt. of phosgene as in Example 2.2. 16.2 pts. by wt. of 1-chlorocarbonyl-2-oxo-3-(3-chlor)-benzalimino-imidazolidine of dec. pt. 190° C. are obtained; this product still contains a small quantity of starting material.

IR (paraffin oil): 1,800 cm$^{-1}$.

Part 17.3.

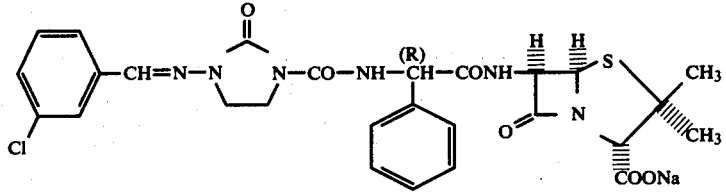

9.3 pts. by wt. of ammpicillin trihydrate in 100 pts. by vol. of 80 per cent strength aqueous THF are reacted with 8.7 pts. by wt. of 1-chlorocarbonyl-2-oxo-3-(3-chloro)-benzalimino-imidazolidine as in Example 1.3. 5.0 pts. by wt. of sodium 6-{D-α-[(2-oxo-3-{3-chloro}-benzalimino-imidazolidin-1-yl)-carbonylamino]-phenylacetamido}-penicillanate are obtained.

IR(KBr): 1,760, 1,720, 1,660 and 1,600 cm$^{-1}$.

3.3 pts. by wt. of cephaloglycine dihydrate in 100 pts. by vol. of 80 per cent strength aqueous THF are reacted with 2.5 pts. by wt. of 1-chlorocarbonyl-2-oxo-3-(3-chloro)-benzalimino-imidazolidine as in Example 1.6. 2.1 pts. by wt. of sodium 7-{D-α-[(2-oxo-3-{3-chloro}-benzalimino-imidazolidin-1-yl)-carbonylamino]-phenyacetamido}-3-acetoxy-methyl-ceph-3-em-4-carboxylate of melting point 212°-218° C. (with decomposition) are obtained.

IR (KBr): 1,765, 1,735, 1,665 and 1,610 cm$^{-1}$.
C$_{29}$H$_{26}$ClN$_6$NaO$_8$S.3H$_2$O; calculated: C 47.65; H 4.42; N 11.49; found: C 47.6; H 4.8; N 11.5.

EXAMPLE 18

Part 18.1.

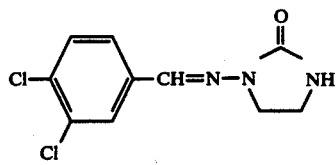

47.6 pts. by wt. of 2-oxo-imidazolidine, 34.5 pts. by wt. of sodium nitrite and 78.4 pts. by wt. of zinc dust, and 87.5 pts. by wt. of 3,4-dichlorobenzaldehyde are reacted as in Example 1.1. 50.4 pts. by wt. of 1-(3,4-dichlor)-benzalimino-2-oxo-imidazolidine of melting point 178°-181° C. are obtained.

IR(KBr); 3,240, 1,710 (broad), 1,470, 1,400 and 1,260 cm$^{-1}$.
NMR(d$_6$-DMSO): 7.95(s,1 H), 7.7(m,3 H), 7.37(s,broad,1 H), m centred at 3.7 (4 H).
calculated: C 46.46; H 3.52; N 16.28; Cl 27.47; found: C 46.4; H 3.6; N 16.1; Cl 27.4.

Part 18.2.

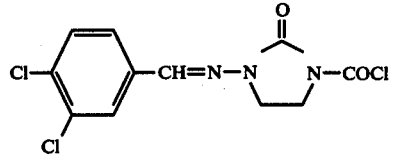

30.0 pts. by wt. of 1-(3,4-dichloro)-benzalimino-2-oxo-imidazolidine and 37.8 pts. by wt. of triethylamine in 250 pts. by vol. of abs. dioxane, and 37.7 pts. by wt. of trimethylchlorosilane in 80 pts. by vol. of abs. dioxane, and 23.1 pts. by wt. of phosgene are reacted as in Example 2.2. 11.2 pts. by wt. of 1-chlorocarbonyl-2-oxo-3-(3,4-dichloro)-benzalimino-imidazolidine of dec. pt. 224°–230° C. are obtained.

IR (paraffin oil): 1,800 cm$^{-1}$.

calculated: C 41.80; H 2.82; N 13.07; Cl 33.07; found: C 41.9; H 2.8; N 12.9; Cl 32.8.

Part 18.3.

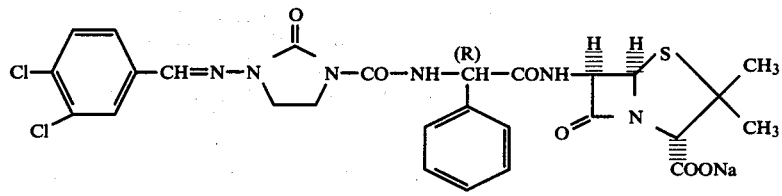

9.4 pts. by wt. of ampicillin trihydrate in 100 pts. by vol. of 80 per cent strength aqueous THF are reacted with 5.0 pts. by wt. of 1-chlorocarbonyl-2-oxo-3-(3,4-dichloro)-benzalimino-imidazolidine as in Example 1.3. 5.3 pts. by wt. of sodium 6-{D-α-[(2-oxo-3-{3,4-dichloro}-benzaliminoimidazolidin-1-yl)-carbonylamino]-phenylacetamido}-penicillanate are obtained.

IR(KBr): 1,765, 1,725, 1,660 and 1,605 cm$^{-1}$.

NMR(CD$_3$OD): 7.3–7.7(aromatic protons and —CH=N—), 5.61 (s,1 H), 5.50 (q,2 H), 4.18 (s,1 H), 3.85 (s,broad,4 H), 1.58 (s,3 H), 1.50 (s,3 H)δ.

Part 18.4.

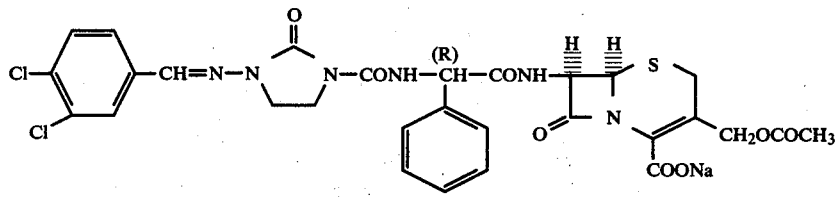

7.0 pts. by wt. of cephaloglycine dihydrate in 100 pts. by vol. of 80 per cent strength aqueous THF are reacted with 5.0 pts. by wt. of 1-chlorocarbonyl-2-oxo-3-(3,4-dichloro)-benzalimino-imidazolidine as in Example 1.6. 7.7 pts. by wt. of sodium 7-{D-α-[(2-oxo-3-{3,4-dichloro}-benzalimino-imidazolidin-1-yl)-carbonylamino]-phenylacetamido}-3-acetoxymethyl-ceph-3-em-4-carboxylate of dec. pt. 190°–5° C. are obtained.

IR(KBr): 1,765, 1,740, 1,665 and 1,615 cm$^{-1}$.

calculated: C 48.95; N 11.80; O 17.99; found: C 49.0; N 11.7; O 18.1.

EXAMPLE 19

Part 19.1.

-continued

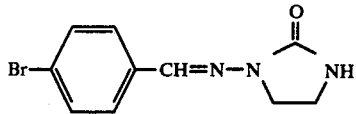

27.8 pts. by wt. of 2-oxo-imidazolidine, 20.0 pts. by wt. of sodium nitrite and 38.0 pts. by wt. of zinc dust, and 54.0 pts. by wt. of 4-bromobenzaldehyde are reacted as in Example 1.1. 22.4 pts. by wt. of 1-(4-bromo)-benzalimino-2-oxo-imidazolidine of melting point 250°–2° C. are obtained.

IR (KBr): 3,240, 3,120, 1,740, 1,705, 1,595, 1,475, 1,415 and 1,270 cm$^{-1}$.

NMR(d$_6$-DMSO): 7.67(aromatic protons and —CH=N—), 7.30 (s, broad,1 H), m centred at 3.6 (4 H)δ.

calculated: C 44.80; H 3.76; N 15.67; found: C 44.9; H 3.7; N 15.3.

Part 19.2.

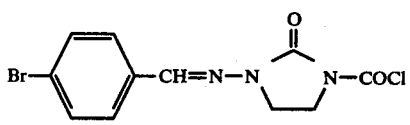

21.7 pts. by wt. of 1-(4-bromo-(benzalimino-2-oxo-imidazolidine and 26.3 pts. by wt. of triethylamine in 250 pts. by vol. of abs. dioxane, and 26.2 pts. by wt. of chlorotrimethylsilane in 80 pts. by vol. of abs. dioxane, and 16.0 pts. by wt. of phosgene are reacted as in Example 2.2.

4.2 pts. by wt. of 1-chlorocarbonyl-2-oxo-3-(4-bromo)-benzalimino-imidazolidine of melting point 177°–180° C. are obtained.

IR (paraffin oil): 1,800 cm$^{-1}$.

Part 19.3.

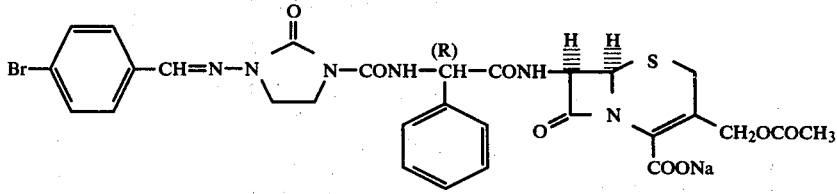

5.7 pts. by wt. of cephaloglycine dihydrate and 4.2 pts. by wt. of 1-chlorocarbonyl-2-oxo-3-(4-bromo)-benzalimino-imidazolidine are reacted as in Example 18.3. 3.5 pts. by wt. of sodium 7-{D-α-[(2-oxo-3-{4-bromo}-benzalimino-imidazolidin-1-yl)-carbonylamino]-phenylacetamido}-3-acetoxymethyl-ceph-3-em-4-carboxylate of dec. pt. 190°-3° C. are obtained.

IR (KBr): 1,760, 1,725, 1,655 and 1,600 cm$^{-1}$.

wt. of 1-chlorocarbonyl-2-oxo-3-(4-methyl)-benzalimino-imidazolidine of melting point 265°-8° C. are obtained.

IR(paraffin oil): 1,800 cm$^{-1}$.

calculted: C 54.24; H 4.55; N 15.82; Cl 13.34; found: C 54.2; H 4.5; N 15.8; Cl 13.6.

Part 20.3.

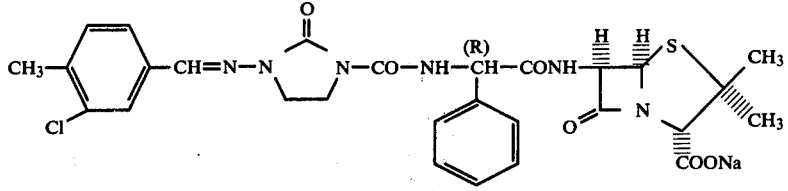

EXAMPLE 20

Part 20.1.

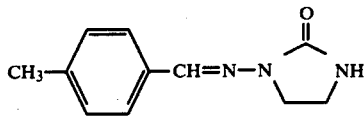

47.6 pts. by wt. of 2-oxo-imidazolidine, 34.5 pts. by wt. of sodium nitrite and 78.4 pts. by wt. of zinc dust, and 60.1 pts. by wt. of 4-methylbenzaldehyde are reacted as in Example 1.1. 52.2 pts. by wt. of 1-(4-methyl)-benzalimino-2-oxo-imidazolidine of melting point 235°-6° C. are obtained.

IR(KBr): 3,230, 3,110, 1,710 (broad), 1,475, 1,410, 1,270 (broad) cm$^{-1}$.

NMR(d$_6$-DMSO): 7.2-7.8(aromatic protons,—CH=N—,NH;6 H), m centred at 3.7(4 H), 2.40 (s,3 H)δ.

calculated: C 65.00; H 6.45; N 20.68; found: C 65.0; H 6.3; N 20.8.

Part 20.2.

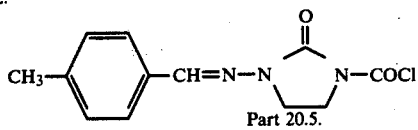

8.1 pts. by wt. of ampicillin trihydrate and 2.7 pts. by wt. of 1-chlorocarbonyl-2-oxo-3-(4-methyl)-benzalimino-imidazolidine are reacted as in Example 2.3. 5.0 pts. by wt. of sodium 6-{D-α-[(2-oxo-3-{4-chloro}-benzalimino-imidazolidin-1-yl)-carbonylamino]-phenylacetamido}-penicillanate of dec. pt. 220°-225° C. are obtained.

IR(KBr): 1,760, 1,725, 1,660 and 1,600 cm$^{-1}$.

NMR(CD$_3$OD): 7.1-7.8(aromatic protons and —CH=N—), 5.60 (s,1 H), 5.45(q,2 H), 4.17(s,1 H), 3.60(s,broad,4 H), 2.18 (s,3 H), 1.58(s,3 H), 1.50 (s,3 H)δ.

C$_{28}$H$_{29}$N$_6$NaO$_6$S.2H$_2$O: calculated: C 52.82; H 5.22; N 13.20; S 5.03; found: C 52.6; H 5.3; N 12.8; S 5.2.

Part 20.4

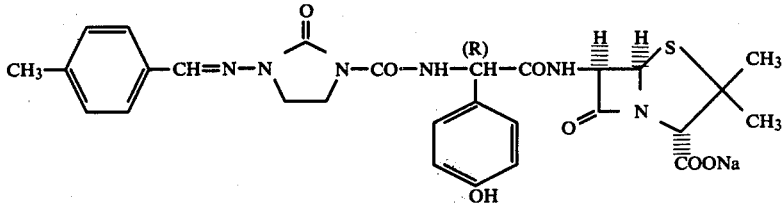

5.0 pts. by wt. of amoxicillin trihydrate and 3.2 pts. by wt. of 1-chlorocarbonyl-2-oxo-3-(4-methyl)-benzalimino-imidazolidine are reacted as in Example 10.5. 6.8 pts. by wt. of sodium 6-{D-α-[(2-oxo-3-{4-methyl}-benzalimino-imidazolidin-1-yl)-carbonylamino]-4-hydroxyphenyl-acetamido}-penicillanate of dec. pt. 230°-5° C. are obtained.

IR(KBr): 1,765, 1,730, 1,665 and 1,610 cm$^{-1}$.

NMR(CD$_3$OD): 7.6-6.7(aromatic protons and —CH=N—), 5.5 (m,3 H), 4.18(s,1 H), 3.6(m,4H), 3.25 (s,3 H), 1.55(s,3 H), 1.50 (s,3 H)δ.

C$_{28}$H$_{29}$N$_6$NaO$_7$S.2H$_2$O: calculated: C 51.53; H 5.09; N 12.87; S 4.91; found: C 51.2; H 5.2; N 12.7; S 5.1.

Part 20.5.

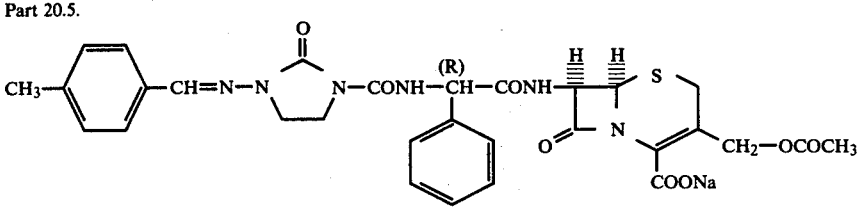

20.3 pts. by wt. of 1-(4-methyl)-benzalimino-2-oxo-imidazolidine, 33.3 pts. by wt. of triethylamine, 32.1 pts. by wt. of chlorotrimethylsilane and 19.8 pts. by wt. of phosgene are reacted as in Example 19.2. 19.6 pts. by 5.0 pts. by wt. of cephaloglycine dihydrate in 50 pts. by vol. of 80 per cent strength aqueous THF are reacted with 3.0 pts. by wt. of 1-chlorocarbonyl-2-oxo-3-(4-methyl)-benzalimino-imidazolidine as in Example 1.6.

5.5 pts. by wt. of sodium 7-{D-α-[(2-oxo-3-{4-methyl}-benzalimino-imidazolidin-1-yl)-carbonylamino]-phenylacetamido}-3-acetoxymethyl-ceph-3-em-4-carboxylate of dec. pt. 178°-80° C. are obtained.

IR(KBr) 1,760, 1,725, 1,660 and 1,615 cm$^{-1}$.

$C_{30}H_{29}N_6NaO_8S \cdot H_2O$: calculated: C 53.41; N 12.47; found: C 53.4; N 12.5.

EXAMPLE 21

Part 21.1.

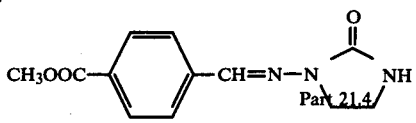

47.6 pts. by wt. of 2-oxo-imidazolidone, 34.5 pts. by wt. of sodium nitrite and 78.4 pts. by wt. of zinc dust, and 77.1 pts. by wt. of 4-carboxy-benzaldehyde, are reacted as in Example 1.1. 82.8 pts. by wt. of 1-(4-carboxy)-benzalimino-oxo-imidazolidine-2-oxo-imidazline are obtained; this is suspended in 200 pts. by vol. of methanol and a solution of diazomethane in ether is added until a yellow coloration persists. A short time after a clear solution has formed, 1-(4-methoxycarbonyl)-benzalimino-2-oxo-imidazolidine of melting point 245°-6° C. crystallises out.

IR(KBr): 2,240, 1,700 with shoulder at 1,720 cm$^{-1}$.

NMR(d$_6$-DMSO): 7.6-8.1(AB system and s at 7.63;5 H), 7.20(s,broad,1 H), 3.88(s,3 H), m centred at 3.7(4 H)δ.

calculated: C 58.29; H 5.30; N 17.00; O 19.41; found: C 58.7; H 5.2; N 17.3; O 19.6.

Part 21.2.

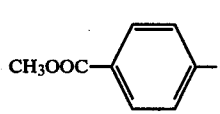

17.4 pts. by wt. of 1-(4-methoxycarbonyl)-benzalimino-2-oxo-imidazolidine, 22.8 pts. by wt. of triethylamine, 22.7 pts. by wt. of chlorotrimethylsilane and 13.9 pts. by wt. of phosgene are reacted as in Example 19.2. 21.0 pts. by wt. of 1-chlorocarbonyl-2-oxo-3-(4-methoxycarbonyl)-benzalimino-imidazolidine of dec. pt. 210°-15° C. are obtained.

IR (paraffin oil): 1,800 cm$^{-1}$.

Part 21.3.

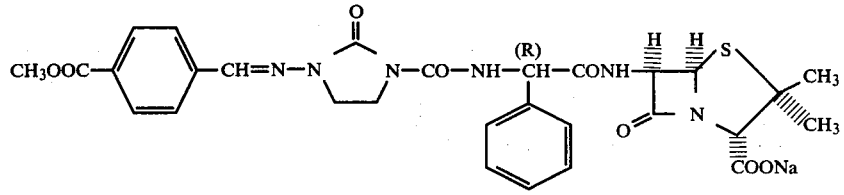

6.2 pts. by wt. of ampicillin trihydrate and 4.6 pts. by wt. of 1-chlorocarbonyl-2-oxo-3-(4-methoxycarbonyl)-benzalimino-imidazolidine are reacted as in Example 2.3. 5.4 pts. by wt. of sodium 6-}D-α-[(2-oxo-3-{4-methoxycarbonyl}-benzalimino-imidazolidin-1-yl)-carbonylamino]-phenylacetamido}-penicillanate of dec. pt. 215°-20° C. are obtained.

IR(KBr): 1,760, 1,720, 1,665 and 1,595 cm$^{-1}$.

NMR(Cd$_3$OD): 8.0-7.1(aromatic protons and —CH=N—, 10 H), 5.58(s,1 H), 5.45(q,2 H), 4.15(s,1 H), m about 3.8(4 H), 2.30(s,3 H), 1.57(s,3 H), 1.50 (s,3 H)δ.

$C_{29}H_{29}N_6NaO_8S \cdot 3 H_2O$: calculated: C 49.86; H 5.05; N 12.02; S 4.58; found: C 49.7; H 5.2; N 11.9; S 4.4.

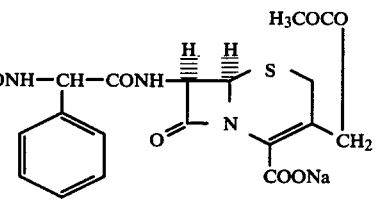

2.3 pts. by wt. of cephaloglycine dihydrate in 40 pts. by vol. of 80 per cent strength aqueous THF are reacted with 2.2 pts. by wt. of 1-chlorocarbonyl-2-oxo-3-(4-methoxycarbonyl)-benzalimino-imidazolidine as in Example 1.6. 1.0 pts. by wt. of sodium 7-{D-α-[(2-oxo-3-{4-methoxycarbonyl}-benzalimino-imidazolidin-1-yl)-carbonylamino]-phenylacetamido}-3-acetoxymethyl-ceph-3-em-carboxylate is obtained. IR (KBr): 1,755, 1,725, 1,665 and 1,600 cm$^{-1}$.

$C_{31}H_{29}N_6NaO_{10}S \cdot 3 H_2O$: calculated: C S.49.34; H 4.67; N 11.14; S 4.25; found: C 49.1; H 4.5; N 11.1; S 4.4.

EXAMPLE 22

Part 22.1.

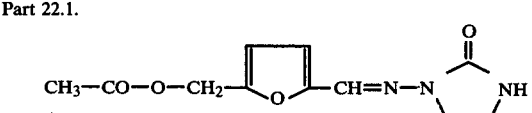

A solution of 1-amino-2-oxo-imidazolidine (3.0 pts. by wt.) in water (30 pts. by vol.) is added to a suspension of 5-acetoxymethyl-furan-2-aldehyde (5.0 pts. by wt.) in water (50 pts. by vol.) over the course of 30 minutes, while stirring and cooling with ice/water. The mixture is then stirred for a further 20 hrs. at 20° C., and thereafter the precipitate is filtered off and washed with isopropanol.

The substance was dried at 70° C. over P$_4$O$_{10}$ in vacuo.

Yield: 6.6 pts. by wt.

Melting point=146° C.

calculated: C 52.6; H 5.2; N 16.7; O 25.5 found: C 52.6; H 5.3; N 16.8; O 25.8.

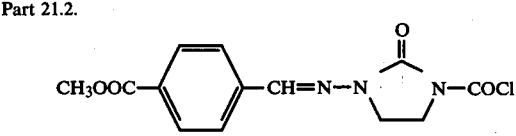

Part 22.2.

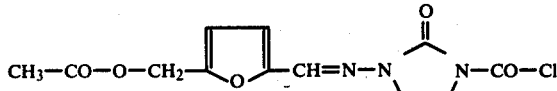

A solution of trimethylchlorosilane (3.2 pts. by wt.) in benzene is added dropwise to a mixture, boiling under reflux, of 1-(5-acetoxymethyl-furfurylideneamino)-2-oxo-imidazolidine (6.6 pts. by wt.), benzene (60 pts. by vol.) and triethylamine (4.1 pts. by vol.) and the mixture is then boiled for a further 20 hrs. The triethylamine hydrochloride is then filtered off while the mixture is still hot, and is rinsed with benzene, and a solution of phosgene (1.6 pts. by vol.) in benzene (10 pts. by vol.) is added to the combined filtrates, whilst cooling. The mixture is left to stand for 20 hrs. at 20° C. and the product is then fltered off.

Yield: 4.3 pts. by wt.

Melting point=184°–85° C.

IR spectrum (in paraffin oil) (carbonyl region): 1,810 and 1,745 cm$^{-1}$.

Calculated: C 45.9; H 3.8; Cl 11.3; N 13.4; O 25.5; found: C 46.4; H 3.9; Cl 11.1; N 13.4; O 25.3.

Part 22.3.

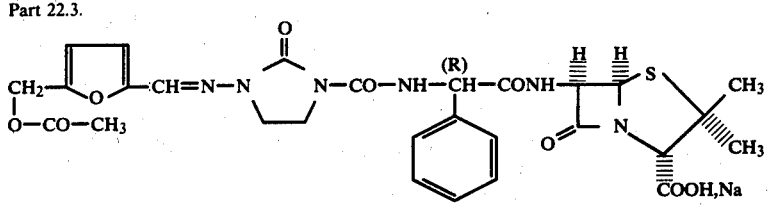

This penicillin is formed when ampicillin trihydrate (2.0 pts. by wt.) and 1-chlorocarbonyl-2-oxo-3-(5-acetoxy methyl-furfurylidene-amino)imidazolidine (1.75 pts. by wt.) are reacted with one another in the manner described in Example 1.3.

Yield:2.8 pts. by wt. of sodium D-α-{[2-oxo-3-(5-acetoxymethylfurfurylideneamino)-imidazolidin-1-yl]-carbonylamino}-benzylpenicillin.

Melting point=material sticks together from about 190° C. (Yield: then progressively decomposes. point=region:

NMR signals at τ=2.37 (1 H), 2.5–2.85 (5 H), 3.15–3.30 (d,1 H), 3.40–3.55 (d,1 H), 4.43 (1 H), 4.43–4.70 (AB,2 H), 4.93 (2 H), 5.87 (1 H), 5.98–6.30 (4 H), 7.94 (3 H), 8.45 (3 H) and 8.52 ppm (3 H).

IR spectrum (in paraffin oil) (carbonyl region): 1,767 (shoulder), 1,734, 1,660, 1,600 and 1,530–1,510 cm$^{-1}$.

β-lactam content: 92%.

Part 22.4.

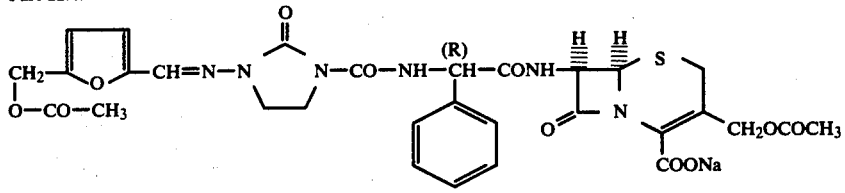

This cephalosporin is obtained when cephaloglycine dihydrate (2.0 pts. by wt.) and 1-chlorocarbonyl-2-oxo-3-(5-acetoxymethyl-furylidene-amino)-imidazolidine (1.5 pts. by wt.) are reacted with one another in the manner described for penicillins in Examples 1.3. and 1.6. On acidification, a part of the cephalosporin is obtained as a precipitate which is insoluble in water and in the organic phase (ethyl acetate):

(Yield:0.1 pts. by wt.; melting point = sticky at 205° C., progressive decomposition up to 260° C., but no clear melt; IR spectrum in the carbonyl region:1,770, 1,726, 1,678, 1,600 and 1,528 cm$^{-1}$ in paraffin oil). The cephalosporin can then be precipitated from the organic phase as described.

Yield: 2.7 pts. by wt. of sodium 7-D-α-|{[2-oxo-3-(5-acetoxymethyl-furylidine-amino)-imidazolidin-1-yl]-carbonylamino}-phenylacetamido|-3-acetoxymethyl-ceph-3-em-4-carboxylate.

β-Lactam content: 86%

IR spectrum (carbonyl region): 1,770 (shoulder), 1,760 (shoulder), 1,730, 1,668, 1,610, 1,550 (shoulder) and 1,530 cm$^{-1}$.

NMR signals at τ=2.33(1 H), 2.45–2.85(5 H), 3.15–3.25 (1 H), 3.4–3.52(1 H), 4.24–4.48(2 H), 4.92(2 H), 5.0–5.22 (3 H), 6.0–6.27(4 H), 6.55–6.75 (2 H), 7.96(3 H) and 8.02 ppm (3 H).

Melting point=from 220° C., dropping and with decomposition.

EXAMPLE 23

Part 23.1.

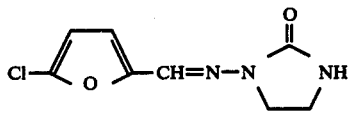

2-Chlorofuran-5-aldehyde is reacted with 1-amino-2-oxo-imidazolidine as in Example 1.1. 1-(5-Chlorofurylideneamino)-2-oxo-imidazolidine of melting point 173°–175° C. is obtained.

NMR (d$_6$-DMSO): 7.45(s,1H), 7.26(s,broad,1H), 6.77(d,1H), 6.60(d,1H), 3.55(m,4H)δ.

Calculated: C 45.0; H 3.7; N 19.7; Cl 16.6; found: C 45.5; H 3.8; N 20.0; Cl 16.2.

Part 23.2.

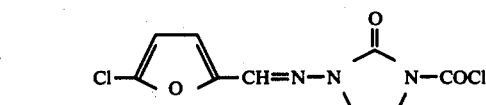

20.0 pts. by wt. of 1-(5-chlorofurylideneamino)-2-oxo-imidazolidine, 31.8 pts. by wt. of triethylamine, 31.8 pts. by wt. of chlorotrimethylsilane and 18.6 pts. by wt. of phosgene are reacted as in Example 1.2.

After recrystallisation from acetonitrile, 16.5 pts. by wt. of 1-chlorocarbonyl-2-oxo-3-(5-chlorofurylideneamino)imidazolidine of dec. pt. 193°-196° C. are obtained.

calculated: Cl 25.68; found: Cl 25.7.

Part 23.3

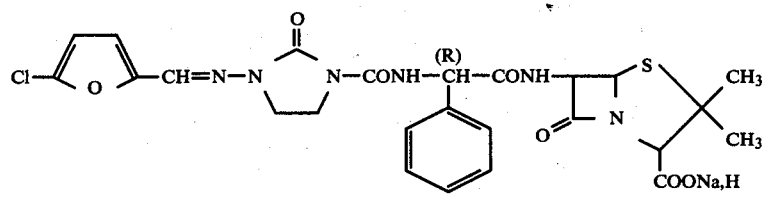

3.9 pts. by wt. of 1-chlorocarbonyl-2-oxo-3-(5-chlorofurylideneamino)-imidazolidine and 5.0 pts. by wt. of ampicillin trihydrate in 100 pts. by vol. of 80 percent strength aqueous THF are reacted as in Example 1.3. 4.7 pts. by wt. of sodium 6-{D-α-[(2-oxo-3-{5-chlorofurylideneamino}-imidazolidin-1-yl)-carbonylamino]-phenylacetamido}-penicillanate of dec. pt. 210°-220° C. are obtained.

IR (KBr) :1,760, 1,720, 1,660, 1,600, 1,525, 1,470, 1,405, 1,270 and 1,225 cm$^{-1}$.

NMR(CD$_3$OD):7.55(s, 1H), 7.3(m, 5H), 6.82(d, 1H), 6.35(d, 1H), 5.56(s, 1H), 5.43(pseudo-q, 2H), 4.12 (s, 1H), 3.82(s,broad, 4H), 1.55(s, 3H), 1.48(s, 3H)δ.

C$_{25}$H$_{24}$ClN$_6$NaO$_7$S.1½ H$_2$O: calculated: C 47.06; H 4.27; N 13.18; S 5.04; found: C 47.1; H 4.7; N 13.2; S 5.2.

Part 23.4.

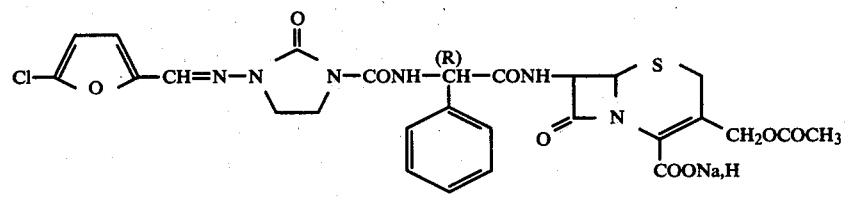

5.0 pts. by wt. of cephaloglycine dihydrate in 100 pts. by vol. of 80 percent strength aqueous THF and 3.5 pts. by wt. of 1-chlorocarbonyl-2-oxo-3-(5-chlorofurylideneamino)imidazolidine are reacted as in Example 1.6. 4.3 pts. by wt. of sodium 7-{D-α-[(2-oxo-3-{5-chlorofurylideneamino}-imidazolidin-1-yl)-carbonylamino]-phenylacetamido=-3-acetoxymethyl-ceph-3-em-4-carboxylate of dec. pt. 185°-190° C. are obtained.

IR (KBr):1.765, 1,720, 1,660, 1,595, 1,520, 1,405 and 1,225 cm$^{-1}$.

NMR (CD$_3$OD/D$_2$O):7.48(s) and 7.37(m, total 6H), 6.78(1H), 6.34(1H), 5.65(1H), 5.43(1H), 4.95(on which is superposed the signal of the exchangeble protons), 3.8(s,broad,4H), 3.6 (on which is superposed the solvent peak), 2.06(s,3H)δ.

EXAMPLE 24

Part 24.1.

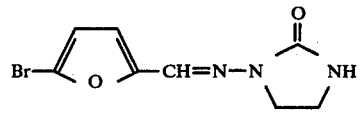

33.5 pts. by wt. of 2-bromofuran-5-aldehyde, dissolved in 100 pts. by vol. of THF, are added to a solution of 1-amino-2-oxo-imidazolidine hydrochloride in 350 pts. by vol. of water, which has been adjusted to pH 5 with sodium hydroxide solution, and the mixture is stirred overnight. The precipitate is filtered off, washed with water and recrystallised from methanol. 30.0 pts. by wt. of 1-(5-bromofurylideneamino)-2-oxo-imidazolidine of dec. pt. 153°-158° C. are obtained.

IR (KBr):1,720, 1,580, 1,410, 1,265 and 1,245 cm$^{-1}$.

NMR (d$_6$-DMSO):7.55(s, 1H), 7.31(s, 1H), 6.80(AB, 2H), m about 3.6 (4H)δ.

Part 24.2.

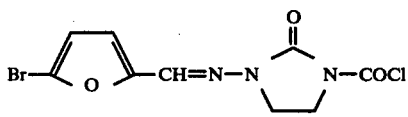

30.0 pts. by wt. of 1-(5-bromofurylideneamimo)-2-oxo-imidazolidine, 37.8 pts. by wt. of triethylamine, 36.8 pts. by wt. of chlorotrimethylsilane and 23.0 pts. by wt. of phosgene are reacted as in Example 1.2.

After recrystallisation from acetonitrile, 21.6 pts. by wt. of 1-chlorocarbonyl-2-oxo-3-(5-bromofurylideneamino)imidazolidine of dec. pt. 190°-194° C. are obtained.

IR (paraffin oil):1,815 cm$^{-1}$.

Part 24.3.

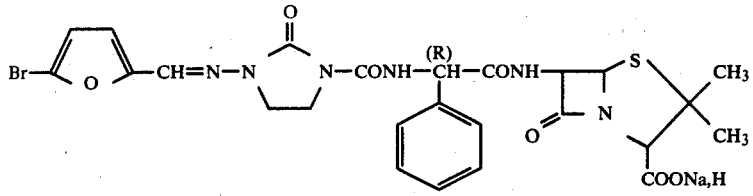

6.1 pts. by wt. of ampicillin trihydrate and 3.2 pts. by wt. of 1-chlorocarbonyl-2-oxo-3-(5-bromofurylideneamino)imidazolidine in 80 pts. by vol. of 80 percent strength aqueous THF are reacted as in Example 1.3. 3.7 pts. by wt. of sodium 6-{D-α-[(2-oxo-3-{5-bromofurylideneamino}-imidazolidin-1-yl)-carbonylamino]-phenylacetamido}-penicillanate of dec. pt. 220°–228° C. are obtained.

IR(KBr):1,760, 1,725, 1,660, 1,600, 1,400 and 1,225 cm$^{-1}$.

NMR (CD$_3$OD):7.60(s, 1H), 7.46(s, 5H), 6.83(d, 1H), 6.52(d, 1H), 5.58(s,1H), 5.50(AB,2H), 4.18 (s, 1H), 3.85(s,broad, 4H), 1,57(s, 3H), 1.50(s, 3H)δ.

Part 24.4.

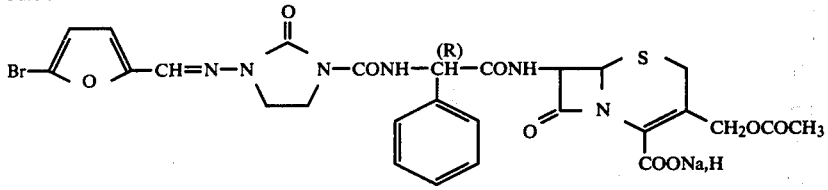

4.5 pts. by wt. of cephaloglycine dihydrate and 3.3 pts. by wt. of 1-chlorocarbonyl-2-oxo-3-(5-bromofurylideneamino)-imidazolidine in 100 pts. by vol. of 80 percent strength aqueous THF are reacted as in Example 1.6. 3.3 pts. by wt. of sodium 7-{D-α-[(2-oxo-3-{5-bromofurylideneamino}-imidazolidin-1-yl)-carbonylamino]-phenylacetamido}-3-acetoxymethyl-ceph-3-em-4-carboxylate of dec. pt. 187°–196° C.

IR(KBr):1,775, 1,715, 1,655, 1,450, 1,450 and 1,275 cm$^{-1}$.

NMR (CD$_3$OD/D$_2$O):7.55(s, 1H), 7.4(m, 5H), 6.80(d, 1H), 6.50 (d, 1H), 5.68(d, 1H), 5.50(s, 1H), 4.96(d, 1H), 4.92(on which is superposed the signal of the exchangeable protons), 3.80(s,broad,4H), 3.4(on which is superposed the solvent peak), 2.08(s, 3H)δ.

EXAMPLE 25

Part 25.1.

CH$_3$—furan—CH=N—N⟨imidazolidinone⟩NH 98.3 pts. by wt. of 2-methylfuran-5-aldehyde ar added to a solution of 1-amino-2-oxo-imidazolidine hydrochloride in 1,000 pts. by vol. of water which has been brought to pH 4.5 with sodium hydroxide solution and the mixture is stirred overnight. The precipitae is filtered off, washed with water and recrystallised from ethanol. 126 pts. by wt. of 1-(5-methylfurylideneamino)-2-oxo-imidazolidine of melting point 194°–6° C. are obtained.

IR (KBr). 3,320, 1,735, 1,710, 1,480, 1,420, 1,395 and 1,245 cm$^{-1}$.

NMR (d$_6$-DMSO):7.57(s, 1H), 7.22(s,broad,1H), 6.67 and 6.25 (AB system, 2H), 3.65(m, 4H), 2.38 (s, 3H)δ.

calculated: C 55.95; H 5.74; N 21.75; found: C 56.0; H 5.8; N 21.3.

Part 25.2.

CH$_3$—furan—CH=N—N⟨imidazolidinone⟩N—COCl 50.0 pts. by wt. of 1-(5-methylfurylideneamino)-2-oxo-imidazolidine, 84.3 pts. by wt. of triethylamine, 84.0 pts. by wt. of chlorotrimethylsilane and 51.4 pts. by wt. of phosgene are reacted as in Example 1.2. After recrystallisation from acetonitrile, 50.7 pts. by wt. of 1-chlorocarbonyl-2-oxo-3-(5-methylfurylideneamino)-imidazolidine of dec. pt. 180°–186° C. are obtained.

IR(paraffin oil): 1,815 cm$^{-1}$.

Part 25.3.

CH$_3$—furan—CH=N—N⟨imidazolidinone⟩N—CONH—CH(R)(Ph)—CONH—penicillin(COONa,H)

6.1 pts. by wt. of ampicillin trihydrate and 2.6 pts. by wt. of 1-chlorocarbonyl-2-oxo-3-(5-methylfurylideneamino)-imidazolidine in 80 pts. by vol. of 80 percent strength aqueous THF are reacted as in Example 1.3. 4.2 pts. by wt. of sodium 6-{D-α-[(2-oxo-3-{5-methylfurylideneamino}- imidazolidin-1-yl)-carbonylamino]-phenylacetamido}-penicillanate of dec. pt. 210°–220° C. are obtained.

IR (KBr): 1,760, 1,720, 1,660, 1,600, 1,525 and 1,410 cm$^{-1}$.

NMR (CD₃OD): 762(s,1H), 7.35(m,5H), 6.75(d,1H), 6.13(d,1H), 5.60(s,1H), 5.45(AB,2H), 4.18(s,1H), 3.83(s,broad,4H), 2.35(s,3H), 1.56(s,3H), 1.49(s,3H).

Part 25.4.

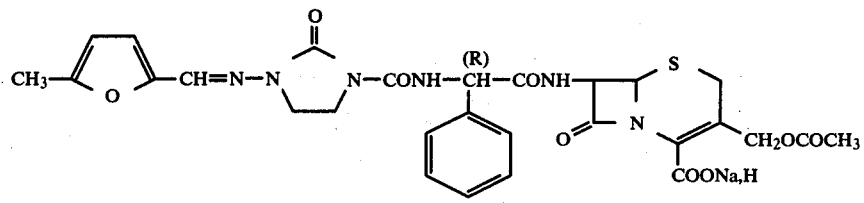

4.4 pts. by wt. of cephaloglycine dihydrate and 2.6 pts. by wt. of 1-chlorocarbonyl-2-oxo-3-(5-methylfurylideneamino)-imidazolidine in 80 pts. by vol. of 80 percent strength aqueous THF are reacted as in Example 1.6. 4.4 pts. by wt. of sodium 7-{D-α-[(2-oxo-3-{5-methylfurylideneamino}-imidazolidin-1-yl)-carbonylamino]-phenylacetamido}-3-acetoxymethyl-ceph-3-em-4-carboxylate are obtained.

IR (KBr): 1,760, 1,725, 1,660, 1,600, 1,525, 1,405 and 1,225 cm⁻¹.

NMR (CD₃OD): 7.70(s,1H), 7.40(m,5H), 6.80(d,1H), 6.20(d,1H), 5.75(d,1H), 5.68(s,1H), 4.95(m,on which is superposed the signal of the exchangeable protons), 3.88(s,broad,4H), 3.45 (on which is superposed the solvent peak), 2.35 (s,3H), 2.04(s,3H)δ.

EXAMPLE 26

Part 26.1.

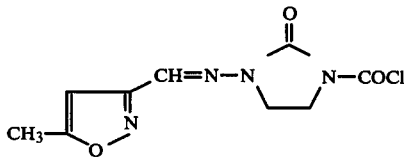

14.0 pts. by wt. of 5-methyl-3-formyl-isoxazole are reacted with 25.6 pts. by wt. of 1-amino-2-oxo-imidazolidine hydrochloride in 100 pts. by vol. of water as in Example 25.1. After 90 minutes, the precipitate is filtered off, washed with water, dried and recrystallised from absolute acetonitrile. 12.5 pts. by wt. of 1-(5-methyl-isoxazol-3-yl-methyleneamino)-2-oxo-imidazolidine of melting point 195°-7° C. are obtained.

IR (paraffin oil): 3,220, 1,695 and 1,610 cm⁻¹.

NMR (CD₃OD): 7.65(s,1H), 7.47(s,broad,1H), 6.53(s,1H), 3.7(m,4H), 2.50(s,3H)δ.

calculated: C 49.48; H 5.19; N 28.85; found: C 49.6; H 5.2; N 29.2.

Part 26.2.

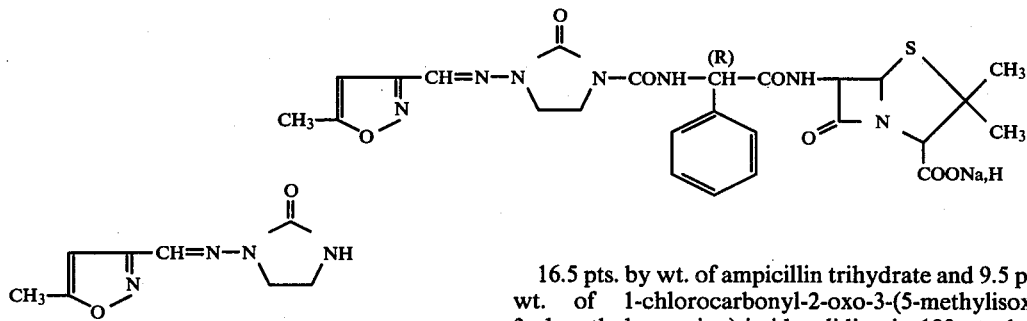

12.0 pts. by wt. of 1-(5-methyl-isoxazol-3-yl-methyleneamino)-2-oxo-imidazolidine, 21.0 pts. by wt. of triethylamine, 20.8 pts. by wt. of chlorotrimethylsilane and 12.3 pts. by wt. of phosgene are reacted as in Example 1.2.

19.8 pts. by wt. of 1-chlorocarbonyl-2-oxo-3-(5-methyl-isoxazol-3-yl-methyleneamino)-imidazolidine of melting point 199°-203° C. are obtained. The compound still contains small amounts of triethylamine hydrochloride which do not have to be removed since they do not interfere with the subsequent reaction.

IR (paraffin oil): 1,790 cm⁻¹.

Part 26.3.

16.5 pts. by wt. of ampicillin trihydrate and 9.5 pts. by wt. of 1-chlorocarbonyl-2-oxo-3-(5-methylisoxazol-3-yl-methyleneamino)-imidazolidine in 100 pts. by vol. of 80 percent strength aqueous THF are reacted as in Example 1.6. 1.0 pt. by wt. of sodium 6-{D-α-[(2-oxo-3-{5-methylisoxazol-3-yl-methyleneamino}-imidazolidin-3-yl)-carbonylamino]-phenylacetamido}penicillanate is obtained.

IR(KBr): 1,760, 1,730, 1,660, 1,600, 1,525, 1,395, and 1,225 cm⁻¹.

NMR(CD₃OD/D₂O): 7.72(s,1H), 7.38(s,5H), 6.62(s,1H), 5.53(s,1H), 5.43(m,2H), 4.13(s,1H), 3.90(m,4H), 2.45(s,3H), 1.53(s,3H), 1.48(s,3H)δ.

Part 26.4.
-continued

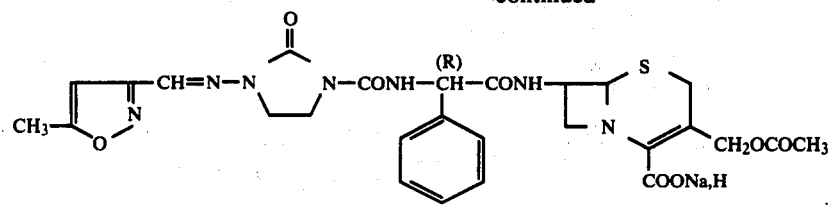

18.1 pts. by wt. of cephaloglycine dihydrate and 9.5 pts. by wt. of 1-chlorocarbonyl-2-oxo-3-(methylisoxazol-3-yl-methyleneamino)-imidazolidine in 150 pts. by vol. of 80 percent strength aqueous THF are reacted as in Example 1.6.

2.2 pts. by wt. of sodium 7-{D-α-[(2-oxo-3-{5-methylisoxazol-3-yl-methyleneamino}-imidazolidin-1-yl)-carbonylamino]phenylacetamido}-3-acetoxymethyl-ceph-3-em-4-carboxylate are obtained. Dec. pt. 215°-220° C.

IR(KBr): 1,760, 1,730(shoulder), 1,670, 1,595 and 1,395 cm$^{-1}$.

NMR(CD$_3$OD/D$_2$O): 7.74(s,1H), 7.38(s,5H), 6.63(s,1H), 5.65(d,1H), 5.50(s,1H), 4.95 (on which is superposed the signal of the exchangeable protons), 3.90(s,broad,4H), 3.4(on which is superposed the solvent peak), 2.45(s,3H), 2.05(s,3H)δ.

EXAMPLE 27

Part 27.1

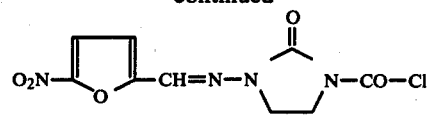

1-(Diacetoxymethyl)-5-nitro-furane (48.6 pts. by wt.) in a mixture of water (216 pts. by vol.) and concentrated H$_2$SO$_4$ (108 pts. by wt.) is boiled for 15 minutes under N$_2$, the mixture is then cooled, the 5-nitro-furfuraldehyde formed is taken up in ether and, after removing the ether, is dissolved in 100 pts. by vol. of methanol. A solution of 1-amino-2-oxo-imidazolidine hydrochloride (27.5 pts. by wt.) in water (100 pts. by vol.) is added to this solution. After 4.5 hrs. the product which has separated out is filtered off, washed with water and dried.

Yield: 42.1 pts. by wt.

Melting point — 259°-260° C. (Kofler heating bench).

calculated: C 42.9; H 3.6; N 25.0; O 28.6; found: C 42.8; H 3.7; N 25.2; O 29.1.

Part 27.2.

-continued

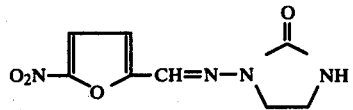

8.0 pts. by wt. of the product described above (27.1.) are silylated in the manner described in Example 1.2. and then reacted with phosgene (2.6 pts. by vol.).

Yield: 5.2 pts. by wt.

Melting point = 188°-190° C. (Kofler bench)

The substance still contains a little triethylamine hydrochloride — the bulk of the triethylamine hydrochloride is removed by washing with methylene chloride — but this does not interfere with the subsequent reaction.

Part 27.3.

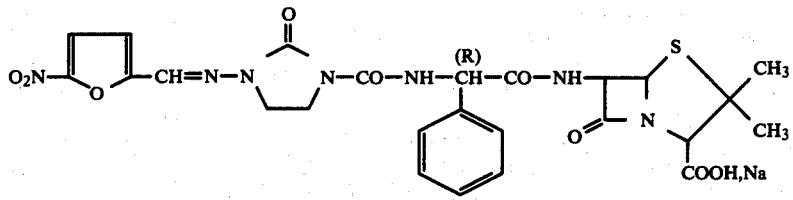

This penicillin is obtained when ampicillin trihydrate (1.5 pts. by wt.) is reacted with 1-chlorocarbonyl-2-oxo-3-(5-nitro-furylideneamido)-imidazolidine (1.1 pts. by wt.) in the manner described in Example 1.3. After working up, 0.7 pt. by wt. of crude sodium salt are obtained. To purify this, it is suspended in a little water and the undissolved matter is filtered off and dried (1st yield: 0.3 pt. by wt.). The aqueous filtrate is covered with ethyl acetate and acidified to pH 1.5, and the sodium salt is then precipitated therefrom in the manner already described (2nd yield: 0.2 pt. by wt.).

Total yield: 0.5 pt. by wt. of sodium D-α-{[2-oxo-3-(5-nitro-furylidene-amino)-imidazolidin-1-yl]-carbonylamino}-benzylpenicillin.

β-Lacta content (according to the NMR spectrum and elementary analysis): 44%. The substance furthermore contains 44% of the product in which the β-lactam ring is open (the reaction mixture had stood for some time at 20° C. after acidification).

According to the NMR spectrum and the analysis, the substance contains 4.8 mol equivalents of water (including the water consumed in opening the β-lactam ring). This was taken into account in the following calculated analytical data:

calculated: C 42.4; H 4.8; N 13.8; S 4.5; found: C 42.1; H 4.8; N 13.8; S 4.3.

Melting point=decomposition from about 260° C. onwards.

IR spectrum (carbonyl region): 1,775(shoulder), 1,745, 1,665, 1,590 and 1,515 cm$^{-1}$ (in Nujol).

Part 27.4

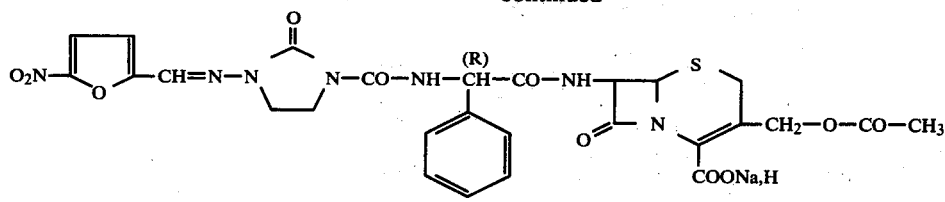

This cephalosporin is obtained when cephaloglycine dihydrate (4.0 pts. by wt.) and 1-chlorocarbonyl-2-oxo-3-(5-nitro-furylidene-amino)-imidazolidine (2.5 pts. by wt.) are reacted with one another in the manner described in Example 1.3. and 1.6. On acidifying the reaction mixture which has been freed from tetrahydrofurane, only a part of the cephalosporanic acid dissolves in the ethyl acetate. The other patt precipitates. The sodium salt is then obtained from both fractions in the manner already described.

Yield: 2.8 pts. by wt. of sodium 7-{D-α-[(2-oxo-3-/5-nitro-furylideneamino/-imidazolidin-1-yl)-carbonylamino]-phenylacetamido}-3-acetoxymethyl-ceph-3-em-4-carboxylate. Melting point=decomposition from about 230° C. to 260° C., but no clear melt (Kofler heating bench).

β-Lactam content (determined iodometrically): 84%. NMR signals (in $d_6$-DMF) at τ=1.95–2.9(8H), 4.1–4.5(2H), 4.9–5.2(3H), 6.0(4H), 6.6–6.85(2H and 8.0 ppm/3H).

IR spectrum (carbonyl region): 1,765 (shoulder), 1,725, 1,670, 1,600 and 1,510 cm$^{-1}$ (in Nujol).

EXAMPLE 28

Part 28.1.

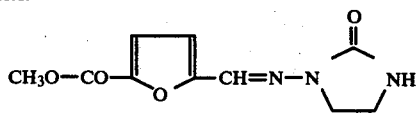

This substance is obtained from 1-amino-2-oxo-imidazolidine (1.2 pts. by wt.) and 5-methoxycarbonyl-furfural (1.8 pts. by wt.) in aqueous methanol (1:1; 12 pts. by vol.) in 60 minutes at 20° C.

Yield: 2,7 pts. by wt.

Melting point = sticks firmly from 88° C. (Kofler bench).

Part 28.2.

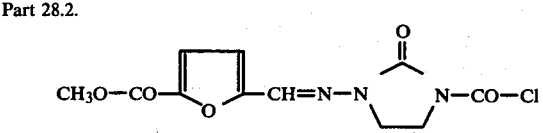

2.6 pts. by wt. of the product described aboe (29.1.) are silylated in the manner described in Example 1.2. and then reacted with phosgene (0.8 pt. by vol.).

Yield: 1.5 pts. by wt.

Melting point = (crude product — still contains some triethylamine hydrochloride) = decomposition at about 220° C. (Kofler bench).

Part 28.3.

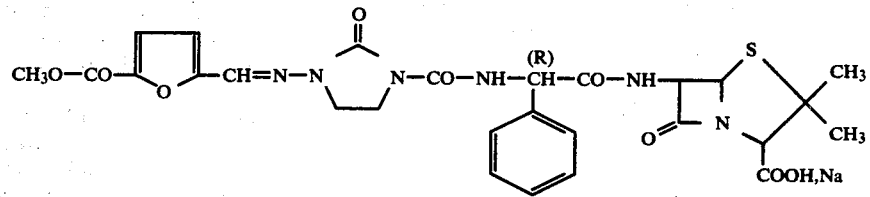

This penicillin is obtained from 0.87 pt. by wt. of ampicillin trihydrate if the latter is reacted with 0.65 pt, by wt. of 1-chlorocarbonyl-2-oxo-3-(5-methoxycarbonyl-furylideneamino)-imidazolidine in the manner described in Example 1.3.

Yield: 0.5 pt. by wt. of sodium D-α-{[2-oxo-3-(5-methoxycarbonyl-forylideneamino)-imidazolidin-1-yl]-carbonylamino}-benzylpenicillin.

β-Lactam content (determined iodometrically): 80%.

Melting point = 185°–210° C., with decomposition (Kofler bench).

IR spectrum (carbonyl region): 1,770, 1,730, 1,670, 1,605 and 1,530 cm$^{-1}$ (in Nujol).

EXAMPLE 29

Part 29.1.

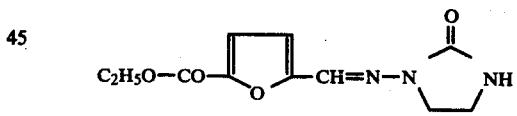

This substance is obtained from 1-amino-2-oxo-imidazolidine (1.3 pts. by wt.) and 5-ethoxycarbonyl-furfural (2.6 pts. by wt.) in aqueous methanol.

Yield: 3.1 pts. by wt.

Melting point (crude product=135°–138° C. (Kofler bench).

Part 29.2.

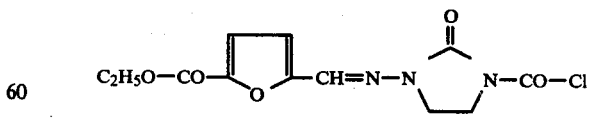

2.85 pts. by wt. of the product described above (30.1.) are silylated in the manner described in Example 1.2. (but using dioxane as the solvent) and then reacted with phosgene (0.9 pt. by vol.).

Yield: 1.1 pts. by wt.

Melting point=230–33° C. (Kofler bench) (crude product).

Part 29.3.

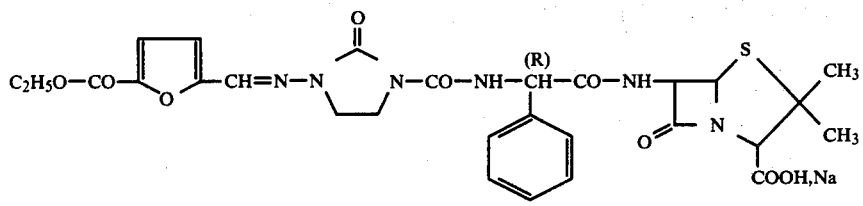

This pencillin is obtained when ampicillin trihydrate (1.3 pts. by wt.) is reacted with 1-chlorocarbonyl-2-oxo-3-(5-ethoxycarbonyl-furylideneamino)-imidazoline (1.0 pt. by wt.) in the manner described in Example 1.3.

Yield: 0.8 pt. by wt. of sodium D-α-{[2-oxo-3-(5-ethoxycarbonyl-furylideneamino)-imidazolidin-1-yl]-carbonylamino}-benzylpencillin.

β-lactam content (determined iodometrically): 92% (the substance contains about 6% of the product in which the β-lactam ring has been opened).

Melting point = about 220° C., with decomposition (Kofler bench).

IR spectrum (carbonyl region): 1,775–1,790, 1740, 1,675, 1,610 and 1,520–1,540 cm$^{-1}$ (in Nujol).

According to analysis and NMR data, the pencillin contains about 4.3 mol equivalents of water and 0.16 mol equivalent of sodium 2-ethylhexanoate.

this was taken into account in the following calculated analytical data:

calculated: C 46.7; H 5.3; N 11.2; S 4.3; found: C 46.7; H 5.6; N 11.2; S 4.5.

EXAMPLE 30

Part 30.1.

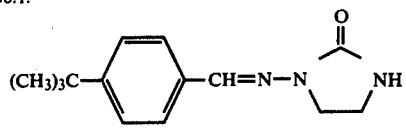

This intermediate product is obtained when 1-amino-2-oxo-imidazolidine hydrochloride (6.9 pts. by wt.) is dissolved in 1 N sodium hydroxide solution (50 pts. by vol.), 4-tertiary butyl-benzaldehyde (8.0 pts. by wt.) is added and the mixture is stirred for 24 hrs. at 20° C. The product which has precipitated is recrystallised from acetonitrile.

Yield: 5.9 pts. by wt.
Melting point = 28° C. (Kofler bench).

Part 30.2.

-continued

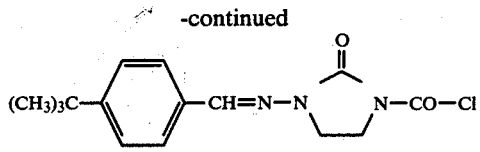

This substance is obtained by the procedure described in Example 1.2 from the product described above (31.1.) (5.5 pts. by wt.), after silylation with triethylchlorosilane (4.4 pts. by wt.) and subsequent reaction with phosgene (2.1 pts. by vol.), using dioxane as the solvent.

The substance still contained some triethylamine hydrochloride.

IR spectrum (COCl): 1,808 cm$^{-1}$ (Nujol).

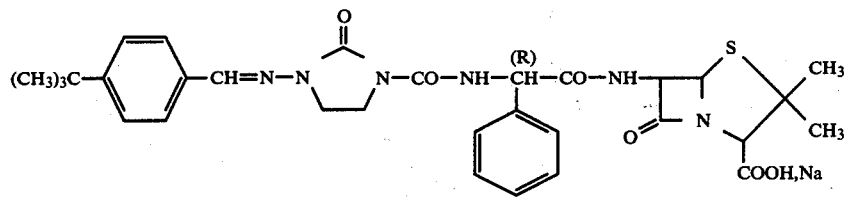

This pencillin is obtained when ampicillin trihydrate (2.2 pts. by wt.) is reacted with 1-chlorocarbonyl-2-oxo-3-(4-tertiary butyl-benzalimino)-imidazolidine (see above: 2.0 pts. by wt.) by the procedure described in Example 1.3.

Yield: 2.7 pts. by wt. of sodium 6-{D-α-[(2-oxo-3-/4-tertiary butyl-benzalimino/-imidazolidin-1-yl)-carbonylamino -phenylacetamido}-penicillanate.

β-Lactam content (determined iodometrically): 83% (the pencillin contained about 10% of the product in which the β-lactam ring has been opened).

Melting point = sticky from about 240° C., a dark melt at about 259° C., which rapidly solidifies again as a result of decomposition.

NMR signals (in CD$_3$OD) at τ=2.15–2.8(10H), 4.4(1H), 4.4–4.65(2H), 5.85(1H), 6.3(broad,4H), 8.45(3H), 8.52(3H) and 8.75ppm(9H).

It follows from the NMR spectrum that the substance contains about 1.8 mol equivalents of water. This was taken into account in the calculated analytical data:

calculated: C 55.1; H 5.8; N 12.4; S 4.7;
found: C 55.1; H 5.9; N 12.4; S 4.8.

IR spectrum (carbonyl region): 1,772, 1,730, 1,672, 1,610 and 1,515–1,530 cm$^{-1}$ (in Nujol).

EXAMPLE 31

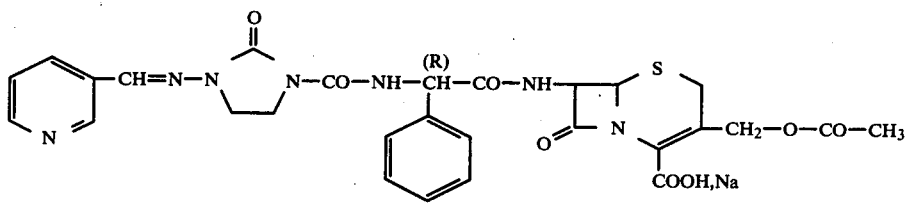

To prepare this cephalosporin, cephaloglycinedihydrate (1.5 pts. by wt.) and 1-chlorocarbonyl-2-oxo-3-(3-pyridyl-methylideneamino)-imidazolidine (0.8 pt. by wt.) are reacted in the manner described in Examples 1.3. and 1.6. After removing the tetrahydrofurane and acidifying the mixture to pH 1.5, the free cephalogsporanic acid separates out as a precipitate which is insoluble in water and in ethyl acetate (0.8 pt. by wt.); melting point: decomposition from about 200° C. onwards—no clear melt up to 260° C. [Kofler heating bench]; IR bands at 1,770, 1,745, 1,675 and 1,520–1,550 cm$^{-1}$ [Nujol]). This acid is dissolved in a little dimethylformamide, 1.3 pts. by vol. of an approximately 1 molar sodium 2-ethylhexanoate solution in ether containing methanol are added and the sodium salt of the cephalosporin is precipitated with ether.

11.0 pts. by wt. of 7-(D-α-amino-phenylacetamido)-3-hydroxymethyl-ceph-3-em-4-carboxylic acid in 100 pts. by vol. of 80 percent strength aqueous THF and 6.1 pts. by wt. of 1-chlorocarbonyl-2-oxo-3-furylideneamino-imidazolidine are reacted, and worked up, as in Example 1.6. 6.9 pts. by wt. of sodium 7-{-α-[(2-oxo-3-furylideneamino-imidazolidin-1-yl)-carbonylamino]-phenylacetamido}-3-hydroxymethyl-ceph-3-em-4-carboxylate of dec. pt. 215–220° C. are obtained.

NMR(CD$_3$OD): 7.80(s,1H), 7.70(s,1H), 6.97(q,1H), 5.75(d,1H), 5.63(s,1H), 5.37(on which are superposed the exchangeable protons). 4.40(s,2H), 3.95(s,broad,4H), the solvent peak (in δ) is superposed on the C-2-protons.

EXAMPLE 33

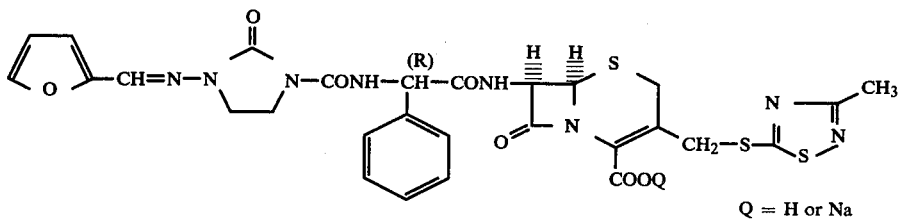

Q = H or Na

Yield: 0.6 pt. by wt. of sodium 7-{D-α-[(2-oxo-3-/3-pyridyl-methylideneamino/-imidazolidin-1-yl)-carbonylamino]-phenylacetamido}-3-acetoxymethyl-ceph-3-em-4-carboxylate.

Melting point=on sprinkling the finely powdered substance on the Kofler heating bench, from 242° C. onwards, the material briefly forms a clear melt, and then immediately decomposes and solidifies and does not melt again below 260° C.

IR spectrum (carbonyl region): 1,770(shoulder), 1,760, 1,730, 1,670, 1605 and 1,530–50 cm$^{-1}$ (in Nujol).

According to the NMR spectrum the substance contains about 5.5 mol equivalents of water and 0.26 mol equivalent of sodium 2-ethyhexanoate. This was taken into account in the following calculated analytical data:

calculated: C 45.9; H 5.2; N 12.5; found: C 45.9; H 5.3; N 12.4.

β-Lactam content: (determined iodometrically) 82%.

EXAMPLE 32

7.5 pts. by wt. of 7-(D-α-amino-phenylacetamido)-3-[(3-methyl-thiadiazol-5-yl)-thiomethyl]-ceph-3-em-4-carboxylic acid in 100 pts. by vol. of 80 percent strength aqueous THF and 6.1 pts. by wt. of 1-chlorocarbonyl-2-oxo-3-furylideneamino-imidazolidine are reacted, and worked up, as in Example 1.6.

5.2 pts. by wt. of sodium 7-{D-α-[(2-oxo-3-furylideneamino-imidazolidin-1-yl)-carbonylamino]-phenylacetamido}-3-[(3-methyl-thiadiazol-5-yl)-thiomethyl]-ceph-3-em-4-carboxylate of dec. pt. 210–215° C. are obtained.

IR(KBr): 1,760, 1,720, 1,660, 1,595, 1,525, 1,475, 1,410, 1,275 and 1,230 cm$^{-1}$.

NMR(CD$_3$OD): 7.70(s,1H). 7.64(d,1H), 7.33(m,5H), 6.86 (d,1H), 6.50(dd,1H), 5.65(d,1H), 5.55(s,1H), 4.90(d,1H), 4.02(pseudo-q,2H), 3.85(s,broad,4H), 3.4(on which is superposed the solvent peak), 2.52(s,3H)δ.

EXAMPLE 34

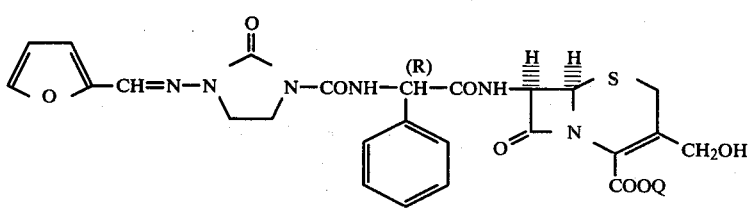

Q = H or Na

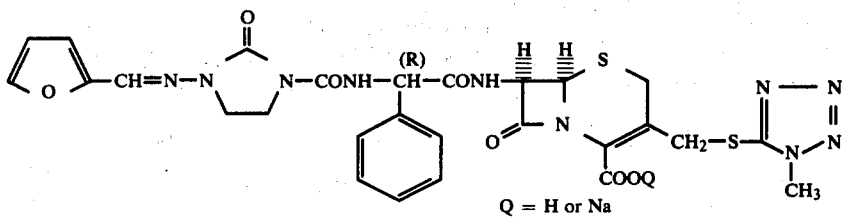

5.0 pts. by wt. of 7-(D-α-amino-phenlacetamido)-3-[(1-methyl-tetrazol-5-yl)-thiomethyl]-ceph-3-em-4-carboxylic acid in 100 pts. by vol. of 80 percent strength aqueous THF and 6.1 pts. by wt. of 1-chlorocarbonyl-2-oxo-3-furylidene-amino-imidazolidine are reacted, and worked up, as in Example 1.6. 3.2 pts. by wt. of sodium 7-{D-α-[(2-oxo-3-furylidene-amino-imidazolidin-1-yl)-carbonylamino]-phenylacetamido}-3-[(1-methyl-tetrazol-5-yl)-thiomethyl]-ceph-3-em-4carboxylate of dec. pt. 210–220° C. are obtained.

IR(KBr): 1,760, 1,720, 1,660, 1,610, 1,520, 1,475, 1,410 and 1,230 cm$^{-1}$.

NMR (CD$_3$OD): 7.73(s,1H), 7.63(d,1H), 7.38(m,5H), 6.88(d,1H), 6.54(q,1H), 5.67(d,1H), 5.56(s,1H), 4.9(on which are superposed the exchangeable protons), 4.32(s,2H), 3.95(s,3H), 3.85(s,broad,4H), 3.45(on which is superposed the solvent peak)δ.

EXAMPLE 35

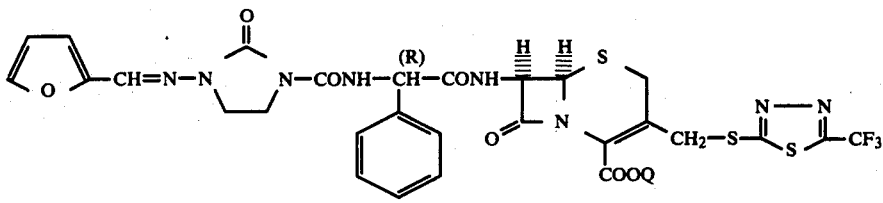

Q = H or Na 8.0 pts. by wt. of 7-(D-α-amino-phenylacetamido)-3-[(5-trifluoromethyl-1.3.4-thiadiazol-2-yl)-thiomethyl]-ceph-3-em-4-carboxylic acid in 100 pts. by vol. of 80 percent strength aqueous THF and 6.1 pts. by wt. of 1-chlorocarbonyl-2-oxo-3-furylideneamino-imidazolidine are reacted, and worked up, as in Example 1.6.

7.8 pts. by wt. of sodium 7-{D-α-[(2-oxo-3-furylideneamino-imidazolidin-1-yl)-carbonylamino]-phenylacetamido]-3-[(5-trifluoromethyl-1.3.4-thiadiazol-2-yl)-thiomethyl]-ceph-3-em-4-carboxylate of dec. pt. 220° C., and of 76% β-lactam content, are obtained.

IR (paraffin oil): carbonyl region: 1,765, 1,720, 1,660, 1,600 and 1,530 cm$^{-1}$.

EXAMPLE 36

Obtained by reacting 2-pyrone-6-aldehyde with 1-amino-imidazolidin-2-on in aqueous methylalcohol at room temperature mp.=(1) 203° (2) 210°

This compound is obtained in the manner described in Example 1.2 from 3.7 pts. by wt. of 1-(2-pyrone-6-aldimino)2-oxo-imidazolidine and 2.5 pts. by wt. of trimethylchlorosilane in dioxane (80 pts. by vol.)

Yield: 3.1 pts. by wt.

mp: 260° C. (decomposition)

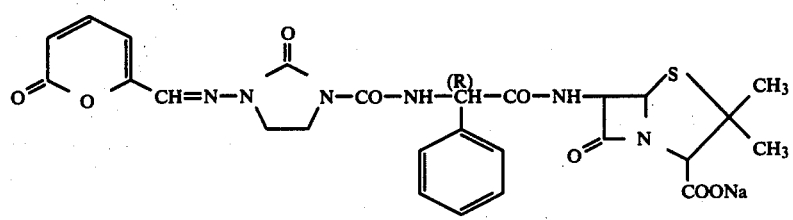

This pencillin is obtained when ampicillin trihydrate (1.5 pts. by wt.) and 1-chlorocarbonyl-2-oxo-3-(2-pyrone-6-aldimino)-imidazolidine (1.0 pts. by wt.) suspended in 80% strength aqueous tetrahydrofurane (30 pts. by vol). are reacted in the manner described in Example 1.3.

Yield: 1.5 pts. by wt. of sodium-6-D-α-{[(2-oxo-3-(2-pyrone-6-yl-methylenamino)-imidazolidin-1-yl]-carbonylamino}-benzylpencillinate NMR signals at τ=2,1–2,8(7H), 3,05–3,25(1H), 3,4–3,7(1H), 4,35(1H), 4,35–4,65(2H;AB), 5,8(1H), 6,0(4H) and 8,3–8,55 ppm (6H).

This penicillin contains about 3.2 mol equivalents of water. This was taken into account in the calculated analytical data:
calculated: C 47,5; H 5,0; N 12,3; S 4,7; found: C 47,7; H 4,8; N 12,6; S 4,8;

Z is $R^1$—CH=N— in which $R^1$ is cycloalkyl of 3 to 10 carbon atoms; cycloalkenyl of 3 to 10 carbon atoms; a pyridyl, styryl or phenyl group unsubstituted or substituted by one or two

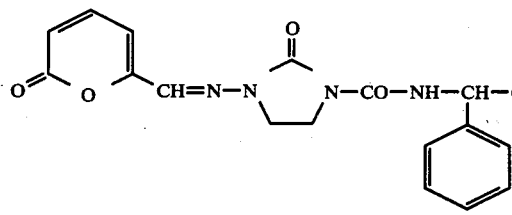
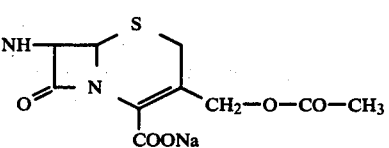

3.5 pts. by wt. of cephaloglycine dihydrate and 2.0 pts. by wt. of 1-chlorocarbonyl-2-oxo-3-(2-pyrone-6-aldimino)-imidazolidine (according to 36.3) in 80 percent strength aqueous THF are reacted as in Example 1.6.

Yield: 3.7 pts. by wt. of sodium-7-{D-α-[(2-oxo-3-(2-pyrone-6-yl-methyleneamino)-imidazolidine-1-yl)-carbonylamino]-phenylacetamido}-3-acetoxymethyl-ceph-3-em-4-carboxylate.

This compound contained 3.2 mol equivalents of water, which was taken into account in the calculated analytical data:
calculated: C 46,8; H 4,4; N 11,7; S 4,5; found: C 46,9; H 4,2; N 11,4; S 4,6.

What is claimed is:

1. A compound selected from the group consisting of a β-lactam of the formula

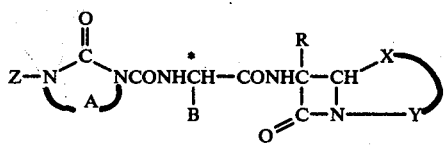

and the pharmaceutically acceptable salts thereof wherein the carbon atom designated C constitutes a center of chirality and R is hydrogen or methoxy
A is ethylene, trimethylene or benzo;
B is phenyl, hydroxyphenyl, halophenyl, lower alkylphenyl, cyanophenyl, methylsulfonylphenyl, cyclohexenyl or cyclohexadienyl;
X is S, O, SO, $SO_2$ or $CH_2$;

Y is

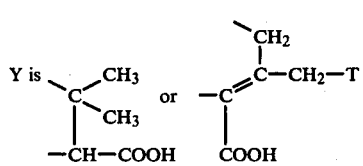

in which T is hydrogen, hydroxy, lower alkanoyloxy, pyridinium, carbamoyloxy, azido, cyano, phenylthio or Het-S- in which Het is a 5- to 6-membered heterocyclic ring containing 1 to 4 hetero-atoms selected from the group consisting of oxygen, sulfur and nitrogen, and containing up to two substituents selected from the group consisting of halo, amino, lower alkylamino, di-lower alkylamino, lower alkyl, cycloalkyl, lower alkoxy, trifluoromethyl, phenyl, benzyl and lower alkanoylamido; and substituents selected from the group consisting of fluoro, chloro, bromo, lower alkyl, lower alkoxy, nitro, cyano, lower alkylsulfonyl or carbo(lower alkoxy); a thienyl or furyl group unsubstituted or substituted by one or two substituents selected from the group consisting of fluoro, chloro, bromo, lower alkyl, carbo(lower alkoxy), lower alkanoyloxy and lower alkanoyloxymethyl; or isoxazolyl unsubstituted or substituted by methyl.

2. A compound according to claim 1 wherein in said lactam
R is hydrogen;
A is ethylene;
B is phenyl, hydroxyphenyl, chlorophenyl, fluorophenyl, methylphenyl, cyanophenyl, methylsulfonylphenyl, or cyclohexa-1,4-dien-1-yl;
X is S; and
Y is

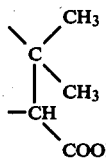

3. A compound according to claim 2 wherein in said lactam

Z is $R^1$—CH=N— in which $R^1$ is a pyridyl, pyronyl, styryl or phenyl group unsubstituted or substituted by one or two substituents selected from the group consisting of fluoro, chloro, bromo, lower alkyl, lower alkoxy, nitro, cyano, lower alkylsulfonyl or carbo(lower alkoxy).

4. A compound according to claim 3 wherein $R^1$ is pyridyl unsubstituted or substituted as therein defined.

5. A compound according to claim 3 wherein $R^1$ is pyronyl unsubstituted or substituted as therein defined.

6. A compound according to claim 3 wherein $R^1$ is phenyl unsubstituted or substituted as therein defined.

7. A compound according to claim 6 wherein $R^1$ is phenyl, chlorophenyl, bromophenyl, fluorophenyl, dichlorophenyl, methylphenyl, t-butylphenyl, methoxyphenyl, nitrophenyl, cyanophenyl, methylsulfonylphenyl, or methoxycarbonylphenyl.

8. A compound according to claim 2 wherein in said lactam
$R^1$ is a thienyl or furyl group unsubstituted or substituted by one or two substituents selected from the group consisting of fluoro, chloro, bromo, lower alkyl, carbo(lower alkoxy), lower alkanoyloxy and lower alkanoyloxymethyl, lower alkoxycarbonyl, lower alkylsulfonyl, lower alkylthio.

9. A compound according to claim 8 wherein R¹ is thienyl unsubstituted or substituted as therein defined.

10. A compound according to claim 9 wherein R¹ is

15. A compound according to claim 1 which is the sodium or potassium salt of said lactam.

16. A compound according to claim 1 wherein the configuration about the carbon atom designated * is R.

17. The compound according to claim 1 which is the lactam of the formula:

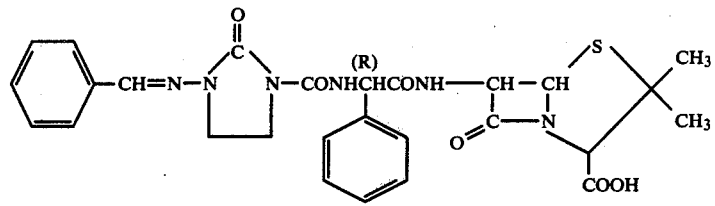

thienyl, chlorothienyl or bromothienyl.

11. A compound according to claim 8 wherein R¹ is furyl unsubstituted or substituted as therein defined.

or the sodium salt thereof.

18. The compound according to claim 1 which is the lactam of the formula:

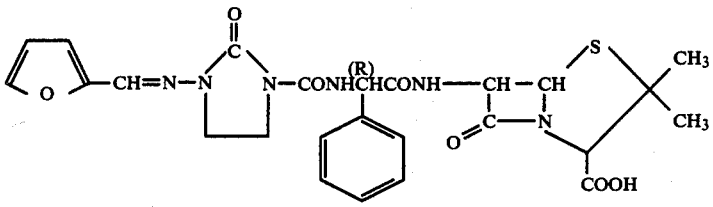

12. A compound according to claim 11 wherein R¹ is furyl, chlorofuryl, bromofuryl, methylfuryl, carbomethoxyfuryl, carbethoxyfuryl or acetoxymethylfuryl, methylsulfonylfuryl, methylthiofuryl.

13. A compound according to claim 2 wherein in said lactam or the sodium salt thereof.

19. The compound according to claim 1 which is the lactam of the formula:

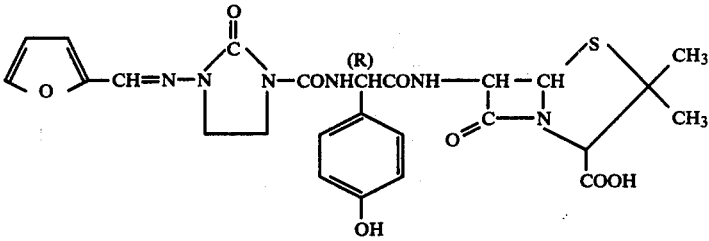

or the sodium salt thereof.

20. The compound according to claim 1 which is the lactam of the formula:

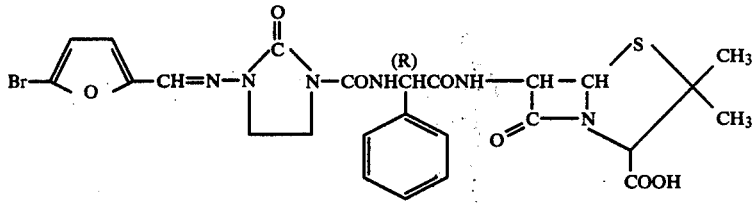

R¹ is methylisoxazolyl.

14. A compound according to claim 1 wherein B is phenyl, p-hydroxyphenyl or cyclohexa-1,4-dien-1-yl.

or the sodium salt thereof.

21. The compound according to claim 1 which is the lactam of the formula:

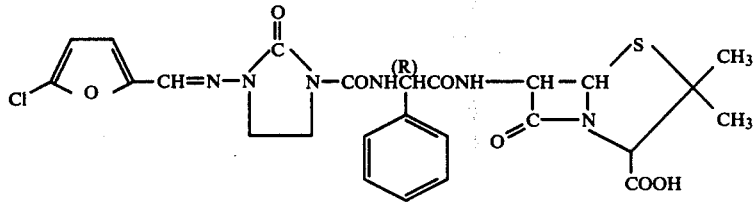

or the sodium salt thereof.

22. The compound according to claim 1 which is the lactam of the formula

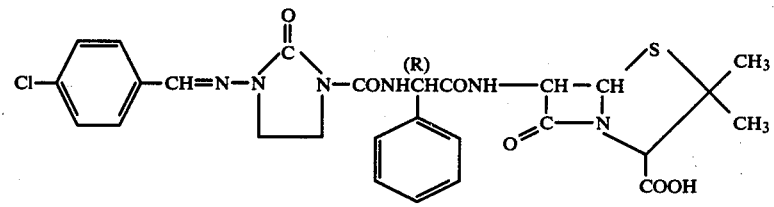

or the sodium salt thereof.

23. The compound according to claim 1 which is the lactam of the formula:

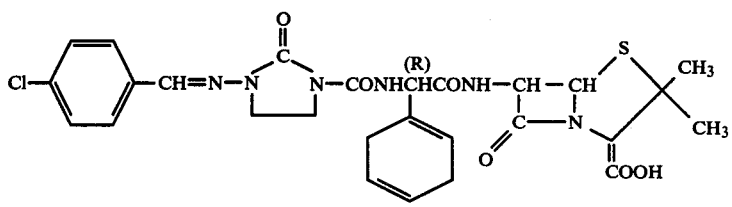

or the sodium salt thereof.

24. The compound accrding to claim 1 which is the lactam of the formula:

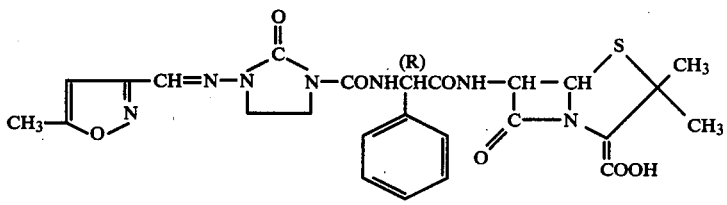

or the sodium salt thereof.

25. The method of combatting bacterial infections in animals and humans which comprises administering thereto an antibacterially effective amount of a compound according to claim 1.

26. A pharmaceutical composition comprising an antibacterially effective amount of a compound according to claim 1 in combination with a pharmaceutical carrier.

27. A compound selected from the group consisting of β-lactams of the formula

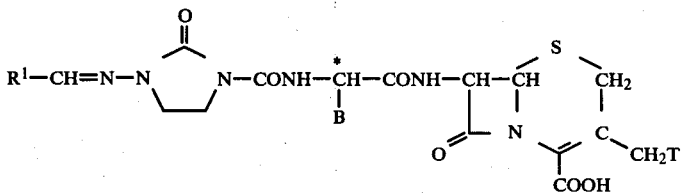

in which

T is hydrogen, hydroxy, lower alkanoyloxy, pyridinium or a tetrazolylthio or thiadiazolylthio group unsubstituted or substituted by methyl, ethyl or trifluoromethyl, $R^1$ is cycloalkyl of 3 to 10 carbon atoms; cycloalkenyl of 3 to 10 carbon atoms; a pyridyl, pyronyl, styryl or phenyl group unsubstituted or substituted by one or two substituents selected from the group consisting of fluoro, chloro, bromo, lower alkyl, lower alkoxy, nitro, cyano, lower alkylsulfonyl or carbo (lower alkoxy), a thienyl or furyl group unsubstituted or substituted by one or two substituents selected from the group consisting of fluoro, chloro, bromo, lower alkyl and lower alkanoyloxymethyl, or isoxazolyl unsubstituted or substituted by methyl, and B is phenyl, hydroxphenyl, chlorophenyl, fluorophenyl, methylphenyl, cyanophenyl, methylsulfonylphenyl or cyclohexa-1,4-dien-1-yl.

28. The compound according to claim 27 which is the lactam of the formula:

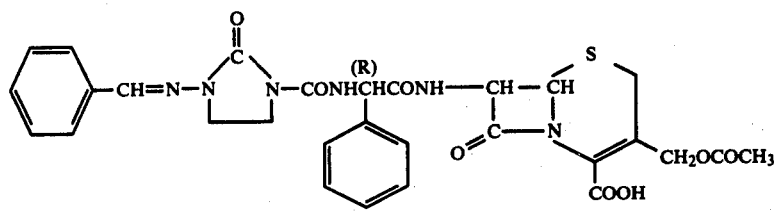

or the sodium salt thereof.

29. The compound according to claim 27 which is the lactam of the formula:

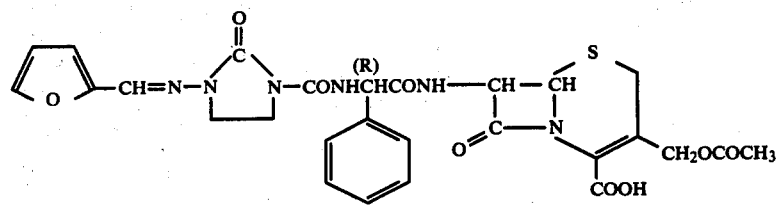

or the sodium salt thereof.

30. The compound according to claim 27 which is the lactam of the formula:

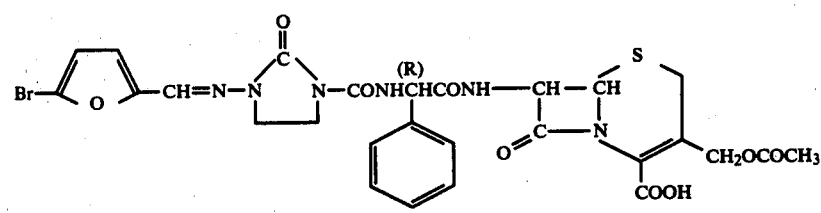

or the sodium salt thereof.

31. The compound according to claim 27 which is the lactam of the formula:

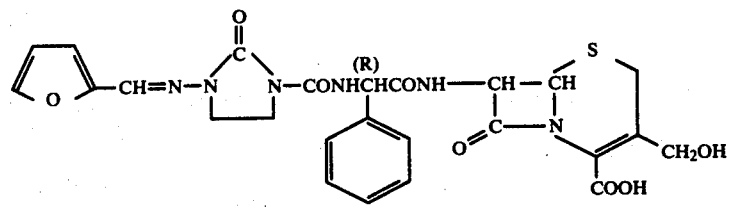

or the sodium salt thereof.

32. The compound according to claim 27 which is the lactam of the formula:

or the sodium salt thereof.

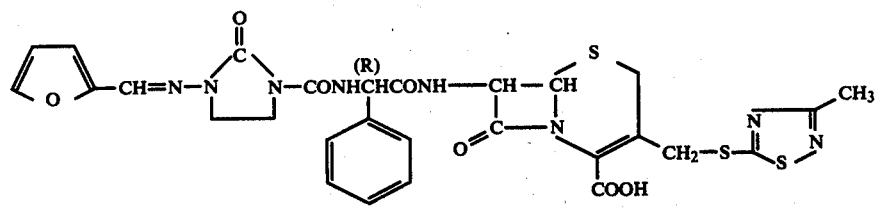

or the sodium salt thereof.

33. The compound according to claim 27 which is the lactam of the formula:

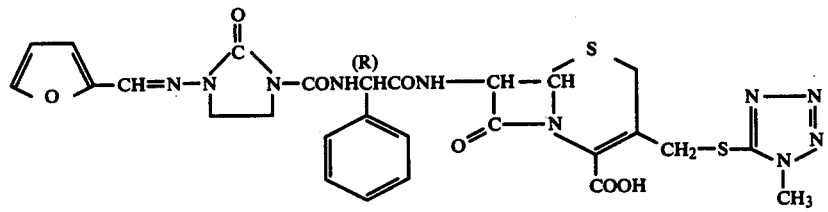

or the sodium salt thereof.

34. The compound according to claim 27 which is the lactam of the formula:

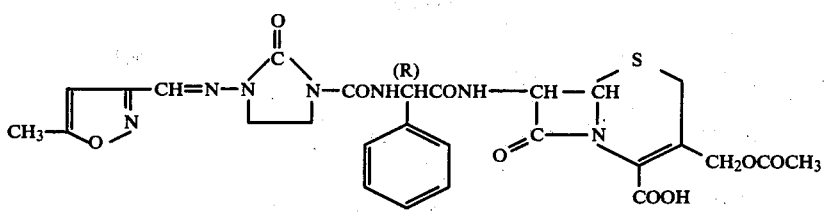

or the sodium salt thereof.

35. A compound according to claim 27 wherein T is hydrogen, hydroxy, acetoxy, 3-methyl-1,2,4-thiadiazol-5-ylthio, 1-methyltetrazol-5-ylthio or 5-trifluoromethyl-1,3,4-thiadiazol-2-ylthio.

36. A compound according to claim 35 wherein in said lactam
$R^1$ is a pyridyl, pyronyl, styryl or phenyl group unsubstituted or substituted by one or two substituents selected from the group consisting of fluoro, chloro, bromo, lower alkyl, lower alkoxy, nitro, cyano, lower alkylsulfonyl or carbo(lower alkoxy).

37. A compound according to claim 36 wherein $R^1$ is pyridyl unsubstituted or substituted as therein defined.

38. A compound according to claim 36 wherein $R^1$ is pyronyl unsubstituted or substituted as therein defined.

39. A compound according to claim 36 wherein $R^1$ is phenyl unsubstituted or substituted as therein defined.

40. A compound according to claim 39 wherein $R^1$ is phenyl, chlorophenyl, bromophenyl, fluorophenyl, dichlorophenyl, methylphenyl, t-butylphenyl, methoxyphenyl, nitrophenyl, cyanophenyl, methylsulfonylphenyl, or carbomethoxyphenyl.

41. A compound according to claim 35 wherein in said lactam
$R^1$ is a thienyl or furyl group unsubstituted or substituted by one or two substituents selected from the group consisting of fluoro, chloro, bromo, lower alkyl, carbo(lower alkoxy), lower alkanoyloxy and lower alkanoyloxymethyl, lower alkoxycarbonyl, lower alkylsulfonyl, lower alkylthio.

42. A compound according to claim 41 wherein $R^1$ is thienyl unsubstituted or substituted as therein defined.

43. A compound according to claim 42 wherein $R^1$ is thienyl, chlorothienyl or bromothienyl.

44. A compound according to claim 41 wherein $R^1$ is furyl unsubstituted or substituted as therein defined.

45. A compound according to claim 44 wherein $R^1$ is furyl, chlorofuryl, bromofuryl, methylfuryl, carbomethoxyfuryl, carbethoxyfuryl, acetoxymethylfuryl, ethoxycarbonylfuryl, methylsulfonylfuryl or methylthiofuryl.

46. A compound according to claim 35 wherein in said lactam
$R^1$ is methylisoxazolyl.

* * * * *